US012558260B2

(12) United States Patent
Schuele et al.

(10) Patent No.: US 12,558,260 B2
(45) **Date of Patent: \*Feb. 24, 2026**

(54) METHODS AND SYSTEMS FOR LASER OPHTHALMIC SURGERY THAT PROVIDE FOR IRIS EXPOSURES BELOW A PREDETERMINED EXPOSURE LIMIT

(71) Applicant: AMO Development, LLC, Irvine, CA (US)

(72) Inventors: Georg Schuele, Portola Valley, CA (US); David A. Dewey, Sunnyvale, CA (US); Javier G. Gonzalez, Palo Alto, CA (US); Alexander Vankov, Mountain View, CA (US)

(73) Assignee: AMO DEVELOPMENT, LLC, Irvine, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/393,287

(22) Filed: Dec. 21, 2023

(65) Prior Publication Data

US 2024/0122756 A1 Apr. 18, 2024

Related U.S. Application Data

(60) Continuation of application No. 17/220,877, filed on Apr. 1, 2021, now Pat. No. 11,865,042, which is a
(Continued)

(51) Int. Cl.
*A61F 9/008* (2006.01)
*A61B 3/14* (2006.01)
(Continued)

(52) U.S. Cl.
CPC ............... *A61F 9/008* (2013.01); *A61B 3/14* (2013.01); *A61B 34/25* (2016.02);
(Continued)

(58) Field of Classification Search
None
See application file for complete search history.

(56) References Cited

U.S. PATENT DOCUMENTS 5,049,147 A 9/1991 Danon
5,720,894 A 2/1998 Neev et al.
(Continued)

FOREIGN PATENT DOCUMENTS

EP 1810646 A1 7/2007
EP 1810647 A1 7/2007
EP 2236109 A1 10/2010

OTHER PUBLICATIONS

21 CFR, Part 1040—Performance Standards for Light-Emitting Products, in effect on Jan. 1, 2017 (see line 3 on p. 1), pp. 1-21. The document can be accessed using the link https://www.ecfr.gov/on/2017-01-01/title-21/chapter-I/subchapter-J/part-1040/section-1040.10.

(Continued)

*Primary Examiner* — Carl H Layno
*Assistant Examiner* — Manolis Pahakis

(57) ABSTRACT

A laser surgical method for performing a corneal incision while maintaining iris exposure below a predetermined exposure limit includes: determining an initial iris exposure based on an initial treatment scan, determining whether the initial iris exposure is less than the predetermined exposure limit, generating a revised treatment scan comprising one or more treatment scan modifying elements when the initial iris exposure is greater than the predetermined exposure limit, and scanning the focal zone of a pulsed laser beam according to the revised treatment scan, thereby performing the corneal incision, wherein the one or more treatment scan modifying elements causes the iris exposure to be smaller than the predetermined exposure limit.

10 Claims, 30 Drawing Sheets

Related U.S. Application Data division of application No. 15/885,616, filed on Jan. 31, 2018, now Pat. No. 10,973,683.

(60) Provisional application No. 62/452,911, filed on Jan. 31, 2017.

(51) Int. Cl.

| | |
|---|---|
| *A61B 17/00* | (2006.01) |
| *A61B 18/00* | (2006.01) |
| *A61B 34/00* | (2016.01) |
| *A61B 34/10* | (2016.01) |
| *A61B 90/00* | (2016.01) |

(52) U.S. Cl.
CPC .............................. *A61F 9/00825* (2013.01); *A61B 2017/00154* (2013.01); *A61B 2018/00601* (2013.01); *A61B 2034/104* (2016.02); *A61B 2090/0409* (2016.02); *A61B 2090/049* (2016.02); *A61F 2009/00853* (2013.01); *A61F 2009/00872* (2013.01); *A61F 2009/00878* (2013.01); *A61F 2009/00887* (2013.01); *A61F 2009/00897* (2013.01)

(56) References Cited

U.S. PATENT DOCUMENTS

| | | | |
|---|---|---|---|
| 5,843,070 A | 12/1998 | Cambier et al. | |
| 5,957,915 A | 9/1999 | Trost | |
| 5,984,916 A | 11/1999 | Lai | |
| 6,019,472 A | 2/2000 | Koester et al. | |
| 6,210,169 B1 | 4/2001 | Yavitz | |
| 6,454,761 B1 | 9/2002 | Freedman | |
| 7,121,665 B2 * | 10/2006 | Su ........................ | A61B 3/0008 |
| | | | 351/205 |
| 7,655,002 B2 | 2/2010 | Myers et al. | |
| 7,717,907 B2 | 5/2010 | Ruiz et al. | |
| 7,801,271 B2 | 9/2010 | Gertner et al. | |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,414,564 B2 | 4/2013 | Goldshleger et al. | |
| 8,728,061 B2 * | 5/2014 | Donitzky ................ | A61F 9/008 |
| | | | 606/4 |
| 9,037,217 B1 | 5/2015 | Peyman | |
| 9,411,938 B2 | 8/2016 | Rathjen | |
| 9,445,946 B2 | 9/2016 | Angeley et al. | |
| 10,485,705 B2 | 11/2019 | Vankov | |
| 10,973,683 B2 | 4/2021 | Schuele et al. | |
| 2004/0243112 A1 | 12/2004 | Bendett et al. | |
| 2005/0049584 A1 | 3/2005 | Homer | |
| 2007/0091264 A1 | 4/2007 | Kahlen | |
| 2007/0173793 A1 * | 7/2007 | Rathjen ................ | A61F 9/00825 |
| | | | 606/4 |
| 2008/0033408 A1 | 2/2008 | Bueler et al. | |
| 2008/0051773 A1 | 2/2008 | Ivanov et al. | |
| 2008/0228176 A1 * | 9/2008 | Triebel .................... | A61F 9/009 |
| | | | 606/4 |
| 2008/0319430 A1 * | 12/2008 | Zenzie ................ | A61B 18/203 |
| | | | 606/9 |
| 2010/0256965 A1 | 10/2010 | Rathjen et al. | |
| 2010/0305553 A1 | 12/2010 | Kittelmann et al. | |
| 2010/0331830 A1 | 12/2010 | Bischoff et al. | |
| 2011/0172649 A1 | 7/2011 | Schuele et al. | |
| 2011/0196350 A1 | 8/2011 | Friedman et al. | |
| 2011/0202114 A1 * | 8/2011 | Kessel .................... | G01N 21/49 |
| | | | 607/88 |
| 2011/0301524 A1 | 12/2011 | Bueler et al. | |
| 2011/0319873 A1 | 12/2011 | Raksi et al. | |
| 2011/0319875 A1 | 12/2011 | Loesel et al. | |
| 2012/0016351 A1 | 1/2012 | Stobrawa et al. | |
| 2012/0095349 A1 | 4/2012 | Peyman | |
| 2012/0130357 A1 | 5/2012 | Triebel et al. | |
| 2012/0150156 A1 | 6/2012 | Wolfel et al. | |

| | | | |
|---|---|---|---|
| 2012/0172852 A1 * | 7/2012 | Lubatschowski et al. | |
| 2013/0085482 A1 * | 4/2013 | Van Valen .......... | A61F 9/00814 |
| | | | 606/5 |
| 2013/0144277 A1 | 6/2013 | Rathjen et al. | |
| 2013/0237972 A1 | 9/2013 | Raksi | |
| 2013/0289544 A1 | 10/2013 | Triebel et al. | |
| 2014/0111766 A1 | 4/2014 | Umekawa et al. | |
| 2014/0114296 A1 | 4/2014 | Woodley et al. | |
| 2014/0114297 A1 * | 4/2014 | Woodley ............... | A61B 3/102 |
| | | | 606/4 |
| 2014/0276680 A1 * | 9/2014 | Dennison ............ | A61F 9/00825 |
| | | | 606/6 |
| 2014/0316389 A1 * | 10/2014 | Schuele .............. | A61F 9/00825 |
| | | | 606/5 |
| 2014/0364840 A1 | 12/2014 | Donitzky et al. | |
| 2015/0335477 A1 * | 11/2015 | Schuele .............. | A61F 9/00825 |
| | | | 606/6 |
| 2016/0106588 A1 * | 4/2016 | Srinivasan ............ | A61B 3/102 |
| | | | 606/5 |
| 2016/0143775 A1 | 5/2016 | Rathjen | |
| 2016/0166431 A1 | 6/2016 | Vogler et al. | |
| 2016/0235588 A1 * | 8/2016 | Hart ................... | A61F 9/00838 |
| 2017/0000647 A1 * | 1/2017 | Schuele ............. | A61F 9/00825 |
| 2017/0000649 A1 * | 1/2017 | Vankov ................. | A61F 9/009 |
| 2017/0007112 A1 * | 1/2017 | Gonzalez ............. | A61F 9/0084 |
| 2017/0011501 A1 * | 1/2017 | Gonzalez ........... | A61F 9/00825 |
| 2017/0035608 A1 * | 2/2017 | Boxer Wachler ...... | A61B 3/135 |
| 2017/0326003 A1 * | 11/2017 | Schuele .............. | A61F 9/00825 |
| 2018/0103837 A1 * | 4/2018 | Kurtz ..................... | A61F 9/008 |
| 2018/0104099 A1 | 4/2018 | Kurtz et al. | |
| 2018/0214305 A1 * | 8/2018 | Schuele .................. | A61B 3/14 |
| 2020/0054489 A1 * | 2/2020 | Thyzel ............... | A61F 9/00802 |

OTHER PUBLICATIONS

"American National Standardfor Safe Use of Lasers," Laser Institute of America, 2014, pp. 1-284.

Fankhauser F., et al., "Lasers in Ophthalmology. Basic, Diagnostic and Surgical Aspects, A Review", Extract from the textbook, published in 2003 (see second page of D13); pp. 79-89.

"Group Safety Publication: Safety of Laser Products, Part 1: Equipment Classification and Requirements," International Standard 60825-1, Second Edition, Mar. 2007, pp. 1-114.

Jean M., et al., "Image Analysis and Modeling in Ophthalmology," CPC Press, Taylor Francis Group, 2014, pp. 265-291.

Konig K., "High-resolution Multiphoton Imaging and Nanosurgery of the Cornea using Femtosecond Laser Pulses," In: Fankhauser F. and Kwasniewska S. (Editors), Lasers in Ophthalmology, Basic, Diagnostic and Surgical Aspects, A Review, 2003, pp. 79-89.

Krueger R.R., et al., "Textbook of Refractive Laser Assisted Cataract Surgery (ReLACS)," 2012.

"Laser safety," Wikipedia, Jan. 2017, pp. 1-16.

Le Harzic R., et al., "Laser Safety Aspects for Refractive Eye Surgery with Femtosecond Laser Pulses," Elsevier GmbH: Medical Laser Application, 2005, vol. 20, pp. 233-238.

Matthes R., "Guidelines on Limits of Exposure to Laser Radiation of Wavelengths between 180 nm and 1,000 μm," Health Physics, 2013, vol. 105(3), pp. 271-295.

Ophthalmic Instruments—Fundamental Requirements and Test Methods, 2006, pp. 1-16.

Priority Application U.S. Appl. No. 62/452,911, filed Jan. 31, 2017.

Probst L.E., et al., "Femtosecond Cataract Surgery A Primer," Chapter 2 ("LensAR Laser System") and Chapter 3 ("LenSx Laser System"), Slack Incorporated, 2012, pp. S002-S037.

Rademacher S.E., et al., "Base-Level Management of Laser Radiation Protection Program," Occupational and Environmental Health Directorate, Feb. 1992.

Roach W.P., et al., "Ultrashort Laser Pulse Bioeffects," SPIE Milestone Series, 2003, pp. 639-647.

Sun H., et al., "Finite Element Model of the Temperature Increase in Excised Porcine Cadaver Iris during Direct Illumination by Femtosecond Laser Pulses," Journal of Biomedical Optics, Jul. 2012, vol. 17(7), pp. 078001-1-078001-6.

(56)　　　　　References Cited

OTHER PUBLICATIONS

Wang J., et al., "Safety of cornea and iris in ocular surgery with 355-nm lasers"; Journal of Biomedical Optics, Sep. 2015, vol. 20(9).

WIPO priority claim, received at WIPO on Feb. 15, 2018, pp. 1-108.

Zuclich J.A., et al., "Ocular Damage Induced by Ultrashort Laser Pulses," Occupational and Environmental Health Directorate, Sep. 1993.

Zuclich J.A., et al., "Wavelength Dependence of Ocular Damage Thresholds in the near-IR to far-IR Transition Region: Proposed Revisions to MPEs," Health Physics Society, 2007, vol. 92(1), pp. 58-66.

Fermann, M.E., et al., "Ultrafast Lasers Technology and Applications," CRC Press, pp. 354-355, 2003.

Fermann, M.E., et al., "Ultrafast Lasers Technology and Applications," CRC Press, pp. 699-765, 2003.

International Commission on Non-Ionizing Radiation Protection:, ICNIPR Guidelines—Revision of Guidelines on Limits of Exposure to Laser Radiation of Wavelengths Between 400 nm and 1.4 pm; published in Health Physics, vol. 79(4), p. 431-440, 2000.

Laser Institute of America: American National Standard for Safe Use of Lasers, published 2014.

South Dakota School of Mines Technology: "Laser safety manual", created 15. Jun. 2007.

Wikipedia: Laser safety, revision Dec. 30, 2006.

Fachverband fur Strahlenschutz e.V.: Leitfaden "Laserstrahlung", Publication date: Dec. 3, 2011 (see second page of D31 and also document D36).

Sliney, David H., "Ophthalmic Laser Safety", Lasers in Ophthalmology Basic, Diagnostic and Surgical Aspects A Review, 14 pages, 2003.

* cited by examiner

FIG. 7A

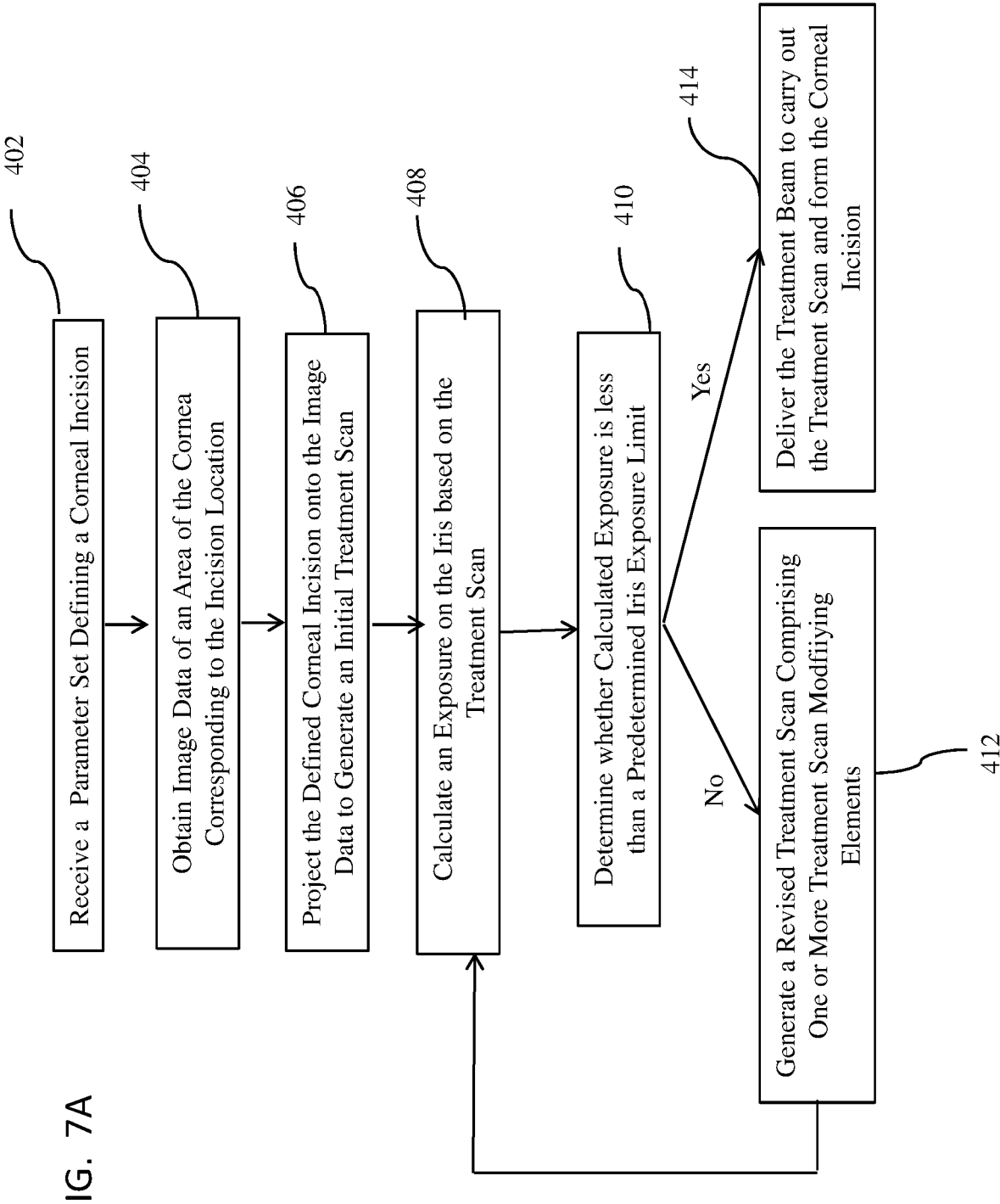

402 Receive a Parameter Set Defining a Corneal Incision

404 Obtain Image Data of an Area of the Cornea Corresponding to the Incision Location 406 Project the Defined Corneal Incision onto the Image Data to Generate an Initial Treatment Scan 408 Calculate an Exposure on the Iris based on the Treatment Scan 410 Determine whether Calculated Exposure is less than a Predetermined Iris Exposure Limit No 412 Generate a Revised Treatment Scan Comprising One or More Treatment Scan Modfiiying Elements Yes 414 Deliver the Treatment Beam to carry out the Treatment Scan and form the Corneal Incision

FIG. 14B

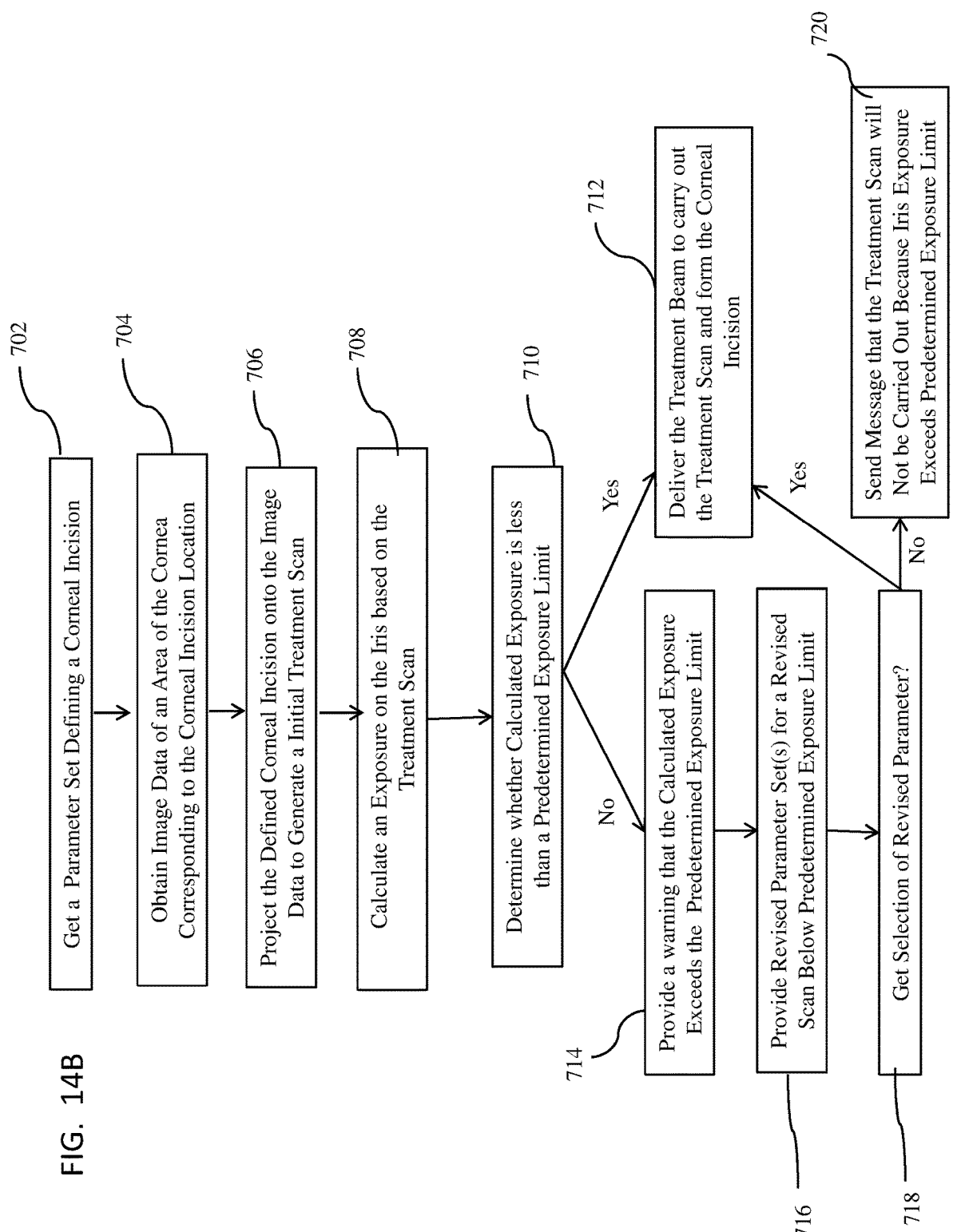

702 — Get a Parameter Set Defining a Corneal Incision

704 — Obtain Image Data of an Area of the Cornea Corresponding to the Corneal Incision Location 706 — Project the Defined Corneal Incision onto the Image Data to Generate a Initial Treatment Scan 708 — Calculate an Exposure on the Iris based on the Treatment Scan 710 — Determine whether Calculated Exposure is less than a Predetermined Exposure Limit Yes 712 — Deliver the Treatment Beam to carry out the Treatment Scan and form the Corneal Incision No 714 — Provide a warning that the Calculated Exposure Exceeds the Predetermined Exposure Limit 716 — Provide Revised Parameter Set(s) for a Revised Scan Below Predetermined Exposure Limit 718 — Get Selection of Revised Parameter?

Yes

No

720 — Send Message that the Treatment Scan will Not be Carried Out Because Iris Exposure Exceeds Predetermined Exposure Limit

METHODS AND SYSTEMS FOR LASER OPHTHALMIC SURGERY THAT PROVIDE FOR IRIS EXPOSURES BELOW A PREDETERMINED EXPOSURE LIMIT

CROSS-REFERENCES TO RELATED APPLICATIONS

This application is a continuation of and claims priority to U.S. patent application Ser. No. 17/220,877, filed Apr. 1, 2021, now U.S. Pat. No. 11,865,042, issued Jan. 9, 2024, which is a divisional of and claims priority to U.S. patent application Ser. No. 15/885,616, filed Jan. 31, 2018, now U.S. Pat. No. 10,973,683, issued Apr. 13, 2021, which claims the benefit under 35 U.S.C. § 119 (e) of U.S. Provisional patent Application No. 62/452,911, filed Jan. 31, 2017, all of which are incorporated herein by reference in their entireties.

BACKGROUND

Laser ophthalmic surgery systems are well known and can be used to make incisions in various ocular tissues, including the cornea. In laser surgical systems, the energy that can be used to make cuts is limited by the amount of light that can be safely exposure to non-target tissues. Melanin in the iris is also much more absorptive of ultraviolet radiation. As a result, use of shorter wavelength for laser surgery can result in higher absorption, which can give rise to localized heating in the iris while incising the cornea. Excessive exposure can lead to photokeratitus, or drug laser interaction damage.

Scanning a laser over the cornea for the purpose of making corneal incisions can result in incident light reaching the iris as illustrated in FIG. 22, thus exposing iris tissue to the emission the from the light source. While retinal safety limits are well established and useful for application to scanning laser systems, the threshold for iris damage from these systems is not well described or understood. As such, there is a need for laser ophthalmic surgical systems which provide for safe iris exposures even when the focal spot of surgical light source is focused on non-iris tissue.

SUMMARY OF THE INVENTION

According to many embodiments, a system for cataract surgery on an eye of a patient comprises: a laser assembly for generating a pulsed laser treatment beam; an imaging system configured for imaging an ocular tissue of the patient, the ocular tissue comprising corneal tissue; an optical scanning system configured for positioning the focal zone of the treatment beam to targeted locations of the ocular tissue, the targeting locations including a location in the corneal tissue; and a computer control system operatively coupled to the laser assembly, the imaging system, and the optical scanning system. The computer control system is programmed to: a) generate an initial treatment scan and an initial iris exposure corresponding to the initial treatment scan; b) determine whether the initial iris exposure is less than a predetermined exposure limit; c) generate a revised treatment scan comprising one or more treatment scan modifying elements when the initial iris exposure is greater than the predetermined exposure limit, wherein the one or more treatment scan modifying elements cause the iris exposure to be smaller than the predetermined exposure limit; and d) operate the optical scanning system and laser assembly to direct a treatment beam in a pattern corresponding to the revised treatment scan so as to create a corneal incision while keeping the iris exposure less than the predetermined limit.

According to many embodiments, a system for cataract surgery on an eye of a patient, comprises: a laser assembly for generating a pulsed laser treatment beam; an imaging system configured for imaging an ocular tissue of the patient, the ocular tissue comprising corneal tissue; an optical scanning system configured for positioning the focal zone of the treatment beam to targeted locations of the ocular tissue, targeting locations including a location in the corneal tissue; and a computer control system operatively coupled to the laser assembly, the imaging system, and the optical scanning system. The controller is programmed to: a) generate an initial treatment scan and an initial iris exposure and an initial scan time corresponding to the initial treatment scan; b) determine a minimum scan time required for the initial iris exposure to be below a predetermined exposure limit; c) determine whether the initial scan time is less than the minimum scan time; d) generate a revised treatment scan comprising one or more treatment scan modifying elements when the initial scan time is less than the minimum scan, wherein the one or more treatment scan modifying elements cause a revised scan time to be longer than the minimum scan time; and e) operate the optical scanning system and laser assembly to direct a treatment beam in a pattern corresponding to the revised treatment scan so as to create a corneal incision while keeping the scan time longer than the minimum scan time.

In many embodiments, including the above embodiments, the one or more treatment scan modifying elements is selected from the group consisting of: an extension of scan paths so that at least a portion of the respective turnarounds occur beyond an incision boundary, wherein the portion of the turnaround extending beyond the boundary is not incisionable materials; a reoriented scan axis; an extension of the scan paths so that at least a portion of the respective turnarounds are gated and extend beyond the incision boundary; and, an insertion of a gated rows with respective active rows in a fixed proportion.

In many embodiments, the one or more treatment scan modifying elements comprises an extension of scan paths so that at least a portion of the respective turnarounds occur beyond an incision boundary, and a region corresponding to the portion of the scan paths extending beyond the incision boundary is not incisionable by the treatment laser beam. In many embodiments, the region beyond incision boundary comprises air, an aqueous medium, or an ophthalmic humor. In many embodiments, this scan modifying element is applied to paracentesis incisions.

In many embodiments, the extension of the scan paths is substantially equal or less than a turnaround distance.

In many embodiments, the extension of the scan paths is greater than 50% of the turnaround distance and less than the turnaround distance, or the extension of the scan paths is greater than 70% of the turnaround distance and less than the turn the turnaround distance, or the extension of the scan paths is greater than 90% of the turnaround distance and less than the turnaround distance.

In many embodiments, the extension of the scan paths is greater than the turnaround distance.

In many embodiments, the one or more treatment scan modifying elements comprises an extension of the scan paths so that at least a portion of the respective turnarounds are gated and extend beyond the incision boundary. In many embodiments, the extension of the scan paths is substantially equal or less than a turnaround distance. In many embodiments, the extension of the scan paths beyond the incision boundary is gated at the turnaround and the extension distance is greater than 50% of the turnaround distance and less than the turnaround distance, or the extension of the scan paths beyond the incision boundary is gated at the turnaround and the extension distance is greater than 70% of the turnaround distance and less than the turn the turnaround distance, or the extension of the scan paths beyond the boundary is gated at the turnaround and the extension distance is greater than 90% of the turnaround distance and less than the turnaround distance.

In many embodiments, the extension of the scan paths beyond the incision boundary is gated and the extension distance is greater than the turnaround distance.

In many embodiments, the one or more treatment scan modifying elements comprises a reoriented of a scan axis. In many incisions, the reoriented axis is reoriented along an axis corresponding to a largest distance between opposing incision boundaries. In many embodiments, this treatment scan modifying element is applied to paracentesis incisions.

In many embodiments, the one or more treatment scan modifying elements comprises an insertion of gated rows with respective active rows in a fixed proportion. In many embodiments, the proportion of gated rows to active rows is substantially one or greater, or the proportion of gated rows to active rows is greater than or equal to substantially one and less or equal to substantially 10:1. In many embodiments, the proportion of gated rows to active rows is substantially 1:1, or substantially 2:1, or substantially 3:1.

In many embodiments, a laser surgical method for performing a corneal incision while maintaining iris exposure below a predetermined exposure limit comprises: determining an initial iris exposure based on an initial treatment scan, the treatment scan corresponding to a predetermined corneal incision, determining whether the initial iris exposure is less than the predetermined exposure limit; generating a revised treatment scan comprising one or more treatment scan modifying elements when the initial iris exposure is greater than the predetermined exposure limit, and scanning the focal zone of a pulsed laser beam according to the revised treatment scan, thereby performing the corneal incision, wherein the one or more treatment scan modifying elements causes the iris exposure to be smaller than the predetermined exposure limit.

In many embodiments, a laser surgical method for performing a corneal incision while maintaining an iris exposure below a predetermined exposure limit, the method comprising: determining an initial iris exposure and an initial scan time based on an initial treatment scan, the treatment scan corresponding to a predetermined corneal incision, determining a minimum scan time required for the initial iris exposure to be below a predetermined exposure limit; determining whether the initial scan time is less than the minimum scan time; generating a revised treatment comprising one or more treatment scan modifying elements, wherein the one or more treatment scan modifying elements causes a revised scan time to be longer than the minimum scan time, and scanning the focal zone of a pulsed laser beam according to the revised treatment scan, thereby performing the corneal incision.

In many embodiments, including the above embodiments, the one or more treatment scan modifying elements is selected from the group consisting of: an extension of scan paths so that at least a portion of the respective turnarounds occur beyond an incision boundary; a reoriented scan axis; an extension of the scan paths so that at least a portion of the respective turnarounds are gated and extend beyond the incision boundary; and, an insertion of a gated rows with respective active rows in a fixed proportion.

In many embodiments, the one or more treatment scan modifying elements comprises an extension of scan paths so that at least a portion of the respective turnarounds occur beyond an incision boundary, and a region corresponding to the portion of the scan paths extending beyond the incision boundary is not incisionable by the treatment laser beam. In many embodiments, the region beyond incision boundary comprises air, an aqueous medium, or an ophthalmic humor. In many embodiments, this scan modifying element is applied to paracentesis incisions.

In many embodiments, the extension of the scan paths is substantially equal or less than a turnaround distance.

In many embodiment, the extension of the scan paths is greater than 50% of the turnaround distance and less than the turnaround distance, or the extension of the scan paths is greater than 70% of the turnaround distance and less than the turn the turnaround distance, or the extension of the scan paths is greater than 90% of the turnaround distance and less than the turnaround distance.

In many embodiments, the extension of the scan paths is greater than the turnaround distance.

In many embodiments, the one or more treatment scan modifying elements comprises an extension of the scan paths so that at least a portion of the respective turnarounds are gated and extend beyond the incision boundary. In many embodiments, the extension of the scan paths is substantially equal or less than a turnaround distance. In many embodiments, the extension of the scan paths beyond the incision boundary is gated at the turnaround and the extension distance is greater than 50% of the turnaround distance and less than the turnaround distance, or the extension of the scan paths beyond the incision boundary is gated at the turnaround and the extension distance is greater than 70% of the turnaround distance and less than the turn the turnaround distance, or the extension of the scan paths beyond the boundary is gated at the turnaround and the extension distance is greater than 90% of the turnaround distance and less than the turnaround distance.

In many embodiments, the extension of the scan paths beyond the incision boundary is gated and the extension distance is greater than the turnaround distance.

In many embodiments, the one or more treatment scan modifying elements comprises a reoriented of a scan axis. In many incisions, the reoriented axis is reoriented along an axis corresponding to a largest distance between opposing incision boundaries. In many embodiments, this treatment scan modifying element is applied to paracentesis incisions.

In many embodiments, the one or more treatment scan modifying elements comprises an insertion of gated rows with respective active rows in a fixed proportion. In many embodiments, the proportion of gated rows to active rows is substantially one or greater, or the proportion of gated rows to active rows is greater than or equal to substantially one and less or equal to substantially 10. In many embodiments, the proportion of gated rows to active rows is substantially one, substantially two, or substantially three.

In many embodiments, a system for cataract surgery on an eye of a patient comprises: a laser assembly for generating a pulsed laser treatment beam; an imaging system configured for imaging an ocular tissue of the patient, the ocular tissue comprising corneal tissue; an optical scanning system configured for positioning the focal zone of the treatment beam to targeted locations of the ocular tissue, the targeting locations including a location in the corneal tissue; a user interface for receiving input from a user, a graphical user interface for providing information to the user; and a computer control system operatively coupled to the laser assembly, the imaging system, the optical scanning system, the user interface and the graphical user interface. The computer control system is programmed to: a) generate an initial treatment scan based on a parameter set received via the user interface, and also generate an initial iris exposure corresponding to the initial treatment scan; b) determine whether the initial iris exposure is less than a predetermined exposure limit; c) generate a revised treatment scan based on a revised parameter set received from the user via the user interface, the revised parameter set having at least one different parameter value than the initial parameter set, d) generate a revised exposure corresponding to the revised treatment scan; and e) operate the optical scanning system and laser assembly to direct a treatment beam in a pattern corresponding to the revised treatment scan so as to create a corneal incision if the revised iris exposure is smaller than the predetermined exposure limit. The act of operating the optical scanning system and laser assembly to direct the treatment beam in a pattern corresponding to the revised treatment scan may proceed automatically after acts (a)-(d). Alternatively, one or more additional acts may be required of a user of the system prior to operating the optical scanning system as in (d). For instance, the system may preferably be configured to provide a message or warning through, for instance, a graphical user interface, to a user that a revised treatment scan has been determined and may be delivered to the patient. The system may require that a user manually command delivery of the treatment scan once an acceptable scan has been determined. The system may require that the user press a button, peddle lever or other device to initiate scan. In some embodiments, it may be preferable that a user be required to continually depress a button, lever, peddle or other device throughout to maintain delivery of the treatment scan from initiation to completion. In some embodiments, a user may be required to enter a command via a graphical user interface in order to initiate a treatment scan.

In many embodiments, a system for cataract surgery on an eye of a patient comprises: a laser assembly for generating a pulsed laser treatment beam; an imaging system configured for imaging an ocular tissue of the patient, the ocular tissue comprising corneal tissue; an optical scanning system configured for positioning the focal zone of the treatment beam to targeted locations of the ocular tissue, the targeting locations including a location in the corneal tissue; a user interface for receiving input from a user, a graphical user interface for providing information to the user; and a computer control system operatively coupled to the laser assembly, the imaging system, the optical scanning system, the user interface and the graphical user interface. The computer controls system is programmed to: a) generate an initial treatment scan based on a parameter set received via the user interface, and also generate an initial iris exposure corresponding to the initial treatment scan; b) determine whether the initial iris exposure is less than a predetermined exposure limit; c) generate one or more revised parameter sets, each of the one or more parameter sets having at least one different parameter value, and generate a revised treatment scan corresponding to each revised parameter set, wherein a revised iris exposure corresponding to each respective revised treatment scan is smaller than the predetermined exposure limit; d) cause the one or more revised parameter sets to be provided to a user via the graphical user interface, e) receive a selected one of the one or more revised parameter sets; and f) operate the optical scanning system and laser assembly to direct a treatment beam in a pattern corresponding to the revised treatment scan generated from the selected parameter set so as to create a corneal incision. The act of operating the optical scanning system and laser assembly to direct the treatment beam in a pattern corresponding to the revised treatment scan may proceed automatically after acts (a)-(e). Alternatively, one or more additional acts may be required of a user of the system prior to operating the optical scanning system as in (f). For instance, the system may preferably be configured to provide a message or warning through, for instance, a graphical user interface, to a user that a revised treatment scan has been determined and may be delivered to the patient. The system may require that a user manually command delivery of the treatment scan once an acceptable scan has been determined. The system may require that the user press a button, peddle lever or other device to initiate scan. In some embodiments, it may be preferable that a user be required to continually depress a button, lever, peddle or other device throughout to maintain delivery of the treatment scan from initiation to completion. In some embodiments, a user may be required to enter a command via a graphical user interface in order to initiate a treatment scan.

In many embodiments, the parameter set includes a plurality of user adjustable parameters. In many embodiments, the plurality of useable adjustable parameters comprises a horizontal spot spacing, a vertical spot spacing and a pulse energy. In many embodiments, the at least one different parameter value comprises one or more of the horizontal spot spacing, the vertical spot spacing and the pulse energy.

In many embodiments, the corneal incision is one or more selected from the group consisting of an arcuate incision, a primary cataract incision and a sideport incision.

In many embodiments, the corneal incision is an arcuate incision and the parameter set defining the arcuate incision comprises a plurality of parameters selected from the groups consisting of incision type, axis, optical zone, arc length, centering method, penetration type, depth units, uncut anterior, uncut posterior and side cut angle, a horizontal spot spacing, a vertical spot spacing and a pulse energy.

In many embodiments, the corneal incision is a primary cataract incision, and the parameter set defining the primary cataract incision comprises a plurality of parameters selected from the groups consisting of axis, limbus offset, width, length, uncut region, depth units, uncut anterior, uncut posterior, uncut central, length, plane depth, side cut angle, horizontal spot spacing, vertical spot spacing and pulse energy.

BRIEF DESCRIPTION OF THE FIGURES

FIG. 7A is a diagram illustrating certain steps and acts in connection with an embodiment of a laser surgical method for performing a corneal incision while maintaining iris exposure below a predetermined exposure limit according to one embodiment.

FIG. 14B is a diagram illustrating certain steps and acts in connection with an embodiment of a laser surgical method for performing a corneal incision while maintaining iris exposure below a predetermined exposure limit according to one embodiment.

DETAILED DESCRIPTION

In the following description, various embodiments of the present invention will be described. For purposes of expla-nation, specific configurations and details are set forth in order to provide a thorough understanding of the embodi-ments. It will also, however, be apparent to one skilled in the art that the present invention can be practiced without the specific details. Furthermore, well-known features may be omitted or simplified in order not to obscure the embodiment being described.

System Overview

Figure 1:
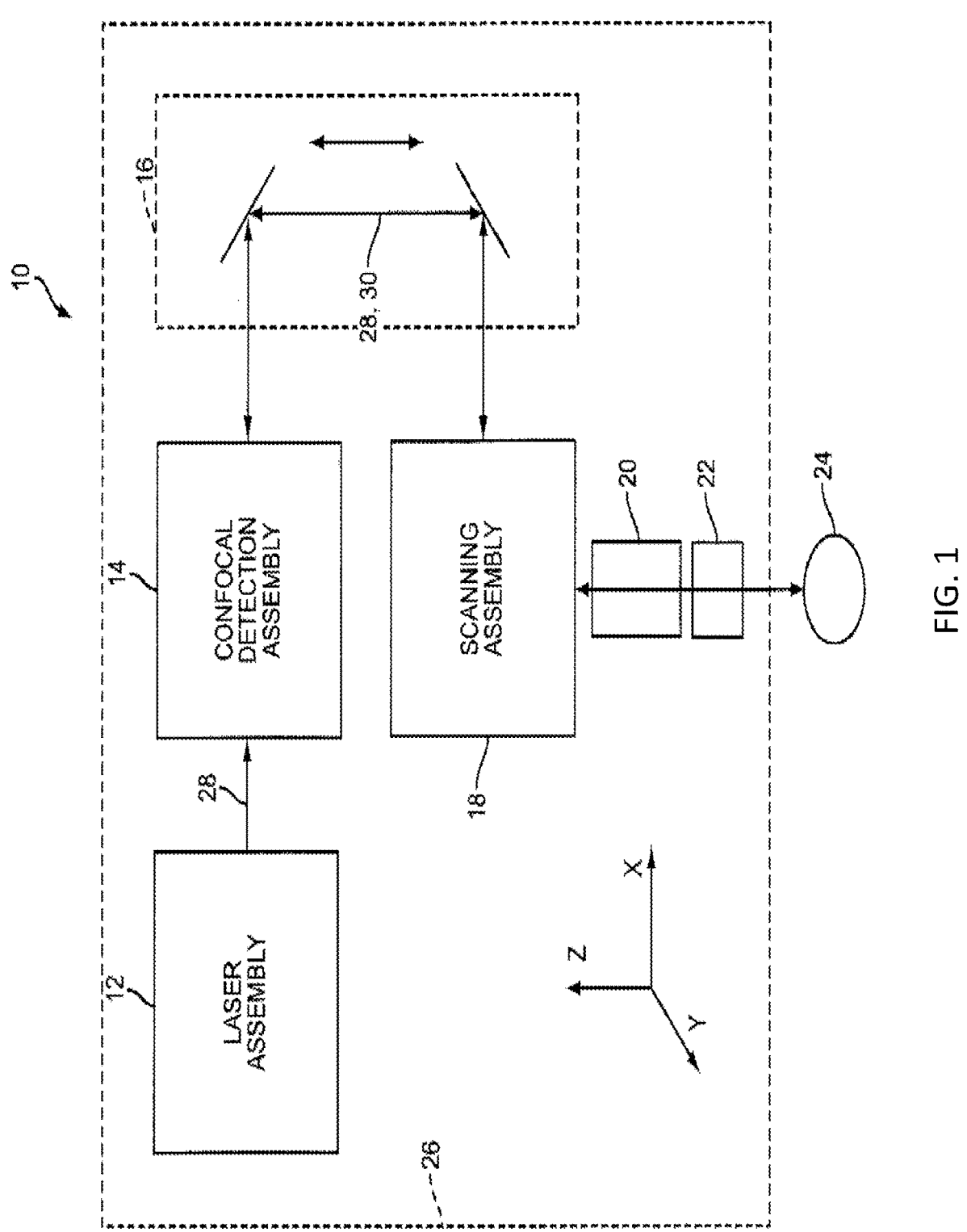
FIG. 1 is a schematic diagram of a laser surgery system, in accordance with many embodiments, in which a patient interface device is coupled to a laser assembly and a detection assembly by way of a scanning assembly and shared optics that supports the scanning assembly.

Referring now to the drawings in which like numbers reference similar elements, FIG. 1 schematically illustrates a laser surgery system 10, in accordance with many embodi-ments. The laser surgery system 10 includes a laser assembly 12, a confocal detection assembly 14, a shared optics 16, a scanning assembly 18, an objective lens assembly 20, and a patient interface device 22. The patient interface device 22 is configured to interface with a patient 24. The patient interface device 22 is supported by the objective lens assembly 20. The objective lens assembly 20 is supported by the scanning assembly 18. The scanning assembly 18 is supported by the shared optics 16. The shared optics 16 has a portion having a fixed position and orientation relative to the laser assembly 12 and the confocal detection assembly 14. In many embodiments, the patient interface device 22 is configured to interface with an eye of the patient 24. For example, the patient interface device 22 can be configured to be vacuum coupled to an eye of the patient 24 such as described in co-pending U.S. Provisional Patent Application Ser. No. 61/721,693, entitled "Liquid Optical Interface for Laser Eye Surgery System", filed Nov. 2, 2012. The laser surgery system 10 can further optionally include a base assembly 26 that can be fixed in place or repositionable. For example, the base assembly 26 can be supported by a support linkage that is configured to allow selective reposi-tioning of the base assembly 26 relative to a patient and secure the base assembly 26 in a selected fixed position relative to the patient. Such a support linkage can be supported in any suitable manner such as, for example, by a fixed support base or by a movable cart that can be reposi-tioned to a suitable location adjacent to a patient. In many embodiments, the support linkage includes setup joints with each setup joint being configured to permit selective articu-lation of the setup joint and can be selectively locked to prevent inadvertent articulation of the setup joint, thereby securing the base assembly 26 in a selected fixed position relative to the patient when the setup joints are locked. Laser surgery system 10, including laser assembly 12, preferably does not include a pulse picker.

In many embodiments, the laser assembly 12 is config-ured to emit an electromagnetic radiation beam 28. The beam 28 can include a series of laser pulses of any suitable energy level, duration, and repetition rate.

In many one embodiments, the laser assembly 12 incor-porates femtosecond (FS) laser technology. By using fem-tosecond laser technology, a short duration (e.g., approxi-mately 10-13 seconds in duration) laser pulse (with energy level in the micro joule range) can be delivered to a tightly focused point to disrupt tissue, thereby substantially lower-ing the energy level required to image and/or modify an intraocular target as compared to laser pulses having longer durations. In other embodiments, a pulse duration of the laser pulses is generally between 1 ps and 100 ns.

The laser assembly 12 can produce laser pulses having a wavelength suitable to treat and/or image tissue. For example, the laser assembly 12 can be configured to emit an electromagnetic radiation beam 28 such as emitted by any of the laser surgery systems described in U.S. application Ser. No. 14/069,042, entitled "Laser Eye Surgery System," filed Oct. 31, 2013 (issued as U.S. Pat. No. 9,445,946); and U.S. patent application Ser. No. 12/987,069, entitled "Method and System For Modifying Eye Tissue and Intraocular Lenses", filed Jan. 7, 2011 (published as U.S. 2011/0172649A1). For example, the laser assembly 12 can produce laser pulses having a wavelength from 1020 nm to 1050 nm. For example, the laser assembly 12 can have a diode-pumped solid-state configuration with a 1030 (+/5) nm center wavelength. As another example, the laser assembly 12 can produce ultraviolet light pulses having a wavelength of between 320 nm and 430 nm, preferably between 320 and 400 nm, preferably between 320 to 370 nm, and more preferably between 340 nm and 360 nm. In many embodiments, the laser pulses have a wavelength of 355 nm. The 320 nm to 430 nm light source may be, for instance, a Nd:YAG laser source operating at the 3rd harmonic wavelength, 355 nm.

When UV wavelengths are used, the tissue modification is preferably carried out using chromophore absorption without plasma formation and/or without bubble formation and an associated cavitation event. Here, chromophore absorption refers to the absorption of at least a portion of the ultraviolet light by one or more chemical species in the target area. The use of ultraviolet light significantly reduces the threshold for plasma formation and associated formation of cavitation bubbles but also decreases the threshold energy required for linear absorption enhanced photodecomposition without the formation of cavitation bubbles for a few reasons. First, the focused spot diameter scales linearly with wavelength which squares the peak radiant exposure within the focal plane. Second, the linear absorption of the material itself allows an even lower threshold for plasma formation or low density photodecomposition as initially more laser energy is absorbed in the target structure. Third, the use of UV laser pulses in the nanosecond and sub-nanosecond regime enables linear absorption enhanced photodecomposition and chromophore guided ionization.

Furthermore, this chromophore guided ionization when using ultraviolet wavelength strongly lowers the threshold for ionization in case of plasma formation as well lowers the threshold for low density photodecomposition for material modification or alteration without cavitation even under very weak absorption. The linear absorption also allows for the specific treatment of topical lens structures (e.g. the lens capsule) as the optical penetration depth of the laser beam is limited by the linear absorption of the lens. This is especially true for aged lenses which absorption in the UV-blue spectral region increases strongly compared to young lenses.

The laser pulses preferably have a wavelength 320 nm to 430 nm. For example, the laser assembly 12 can include an Nd:YAG laser source operating at the 3rd harmonic wavelength (355 nm) and producing pulses having 50 picosecond to 15 nanosecond pulse duration. Depending on the spot size, typical pulse energies used can be in the nanojoule to micro joule range. The laser assembly 12 can also include two or more lasers of any suitable configuration.

The laser assembly 12 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses.

Such conditioning components can include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 and the confocal detection assembly 14 have fixed positions relative to the base assembly 26. The beam 28 emitted by the laser assembly 12 propagates along a fixed optical path through the confocal detection assembly 14 to the shared optics 16. The beam 28 propagates through the shared optics 16 along a variable optical path 30, which delivers the beam 28 to the scanning assembly 18. In many embodiments, the beam 28 emitted by the laser assembly 12 is collimated so that the beam 28 is not impacted by patient movement induced changes in the length of the optical path between the laser assembly 12 and the scanner 16. The scanning assembly 18 is operable to scan the beam 28 (e.g., via controlled variable deflection of the beam 28) in at least one dimension. In many embodiments, the scanning assembly 18 is operable to scan the beam 28 in two dimensions transverse to the direction of propagation of the beam 28 and is further operable to scan the location of a focal point of the beam 28 in the direction of propagation of the beam 28. The scanned beam is emitted from the scanning assembly 18 to propagate through the objective lens assembly 20, through the interface device 22, and to the patient 24.

The shared optics 16 is configured to accommodate a range of movement of the patient 24 relative to the laser assembly 12 and the confocal detection assembly 14 in one or more directions while maintaining alignment of the beam 28 emitted by the scanning assembly 18 with the patient 24. For example, in many embodiments, the shared optics 16 is configured to accommodate a range movement of the patient 24 in any direction defined by any combination of unit orthogonal directions (X, Y, and Z).

The shared optics 16 supports the scanning assembly 18 and provides the variable optical path 30, which changes in response to movement of the patient 24. Because the patient interface device 22 is interfaced with the patient 24, movement of the patient 24 results in corresponding movement of the patient interface device 22, the objective lens assembly 20, and the scanning assembly 18. The shared optics 16 can include, for example, any suitable combination of a linkage that accommodates relative movement between the scanning assembly 18 and, for example, the confocal detection assembly 24, and optical components suitably tied to the linkage so as to form the variable optical path 30.

A portion of the electromagnetic radiation beam 28 that is reflected by eye tissue at the focal point propagates back to the confocal detection assembly 14. Specifically, a reflected portion of the electromagnetic radiation beam 28 travels back through the patient interface device 22, back through the objective lens assembly 20, back through (and descanned by) the scanning assembly 18, back through the shared optics 16 (along the variable optical path 30), and to the confocal detection assembly 14. In many embodiments, the reflected portion of the electromagnetic radiation beam that travels back to the confocal detection assembly 14 is directed to be incident upon a sensor that generates an intensity signal indicative of intensity of the incident portion of the electromagnetic radiation beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, and the posterior surface of the lens capsule. In many embodiments, the amount of the reflected electromagnetic radiation beam that travels to the confocal detection assembly 14 is substantially independent of expected variations in the length of the variable optical path 30 due to patient movement, thereby enabling the ability to ignore patient movements when processing the intensity signal to image/locate structures of the eye.

Figure 2:
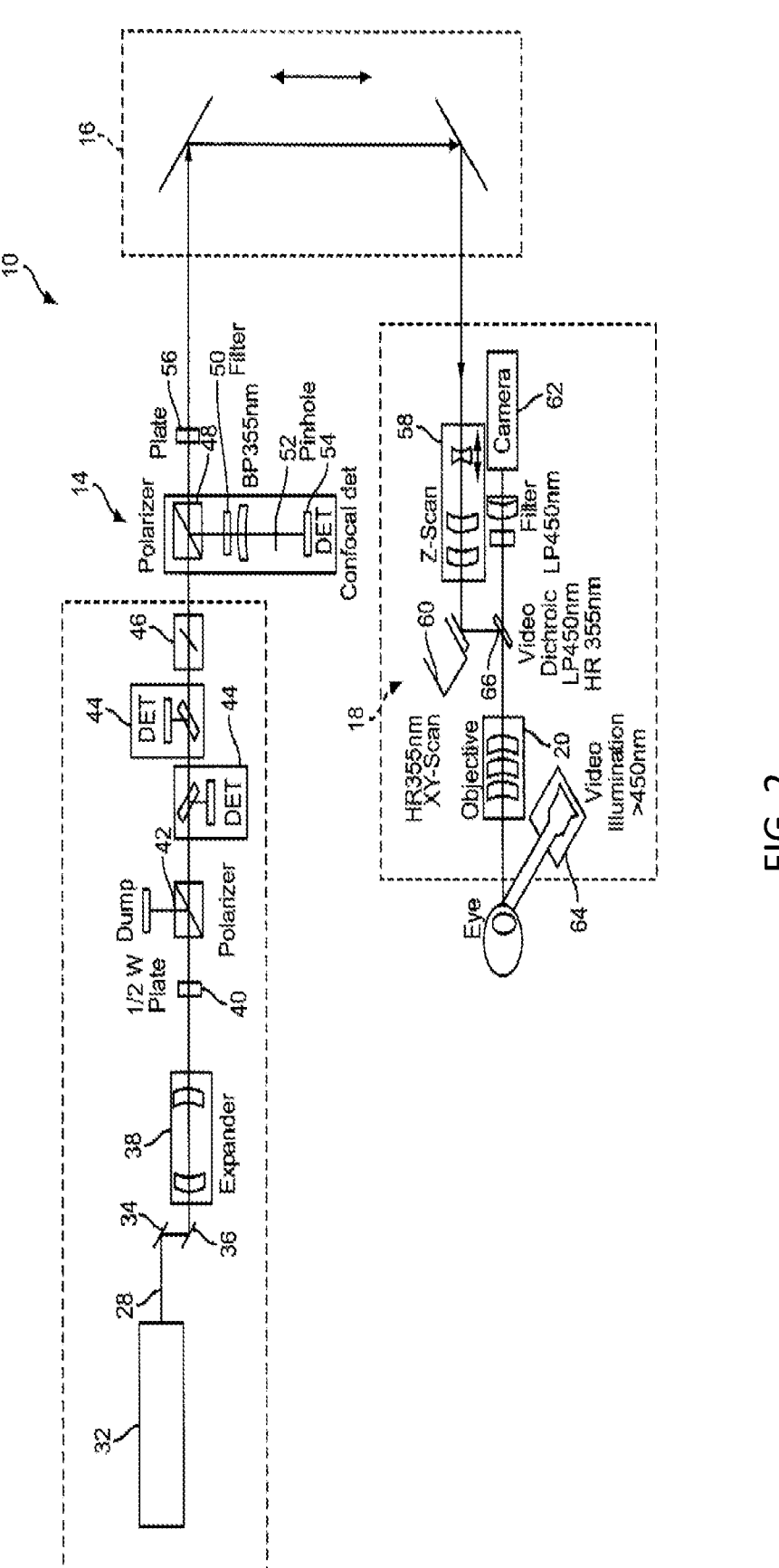
FIG. 2 is a schematic diagram of an embodiment of the laser surgery system of FIG. 1.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 can include an ultrafast (UF) laser 32 (e.g., a femtosecond laser), alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 is deflected by the alignment mirrors 34, 36. In many embodiments, the alignment mirrors 34, 36 are adjustable in position and/or orientation so as to provide the ability to align the beam 28 with the downstream optical path through the downstream optical components. Next, the beam 28 passes through the beam expander 38, which increases the diameter of the beam 28. Next, the expanded beam 28 passes through the one-half wave plate 40 before passing through the polarizer. The beam exiting the laser is linearly polarized. The one-half wave plate 40 can rotate this polarization. The amount of light passing through the polarizer depends on the angle of the rotation of the linear polarization. Therefore, the one-half wave plate 40 with the polarizer acts as an attenuator of the beam 28. The light rejected from this attenuation is directed into the beam dump. Next, the attenuated beam 28 passes through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

As shown in the illustrated embodiment, the confocal detection assembly 14 can include a polarization-sensitive device such as a polarized or unpolarized beam splitter 48, a filter 50, a focusing lens 51, a pinhole aperture 52, and a detection sensor 54. A one-quarter wave plate 56 is disposed downstream of the polarized beam splitter 48. The beam 28 as received from the laser assembly 12 is polarized so as to pass through the polarized beam splitter 48. Next, the beam 28 passes through the one-quarter wave plate 56, thereby rotating the polarization axis of the beam 28. A quarter rotation is a presently preferred rotation amount. After reflecting from the focal point in the eye, the returning reflected portion of the beam 28 passes back through the one-quarter wave plate 56, thereby further rotating the polarization axis of the returning reflected portion of the beam 28. Ideally, after passing back through the one-quarter wave plate 56, the returning reflected portion of the beam has experienced a total polarization rotation of 90 degrees so that the reflected light from the eye is fully reflected by the polarized beam splitter 48. The birefringence of the cornea can also be taken into account if, for example, the imaged structure is the lens. In such a case, the plate 56 can be adjusted and/or configured so that the double pass of the plate 56 as well as the double pass of the cornea sum up to a polarization rotation of 90 degrees. Because the birefringence of the cornea may be different from patient to patient, the configuration/adjustment of the plate 56 can be done dynamically so as to optimize the signal returning to the detection sensor 54. Accordingly, the returning reflected portion of the beam 28 is now polarized to be at least partially reflected by the polarized beam splitter 48 so as to be directed through the filter 50, through the lens 51, and to the pinhole aperture 52. The filter 50 can be configured to block wavelengths other than the wavelengths of interest. The pinhole aperture 52 is configured to block any returning reflected portion of the beam 28 reflected from locations other than the focal point from reaching the detection sensor 54. Because the amount of returning reflected portion of the beam 28 that reaches the detection sensor 54 depends upon the nature of the tissue at the focal point of the beam 28, the signal generated by the detection sensor 54 can be processed in combination with data regarding the associated locations of the focal point so as to generate image/location data for structures of the eye.

In this embodiment, the same laser assembly may be used both for treatment (i.e. modification) and imaging of the target tissue. For instance, the target tissue may be imaged by raster scanning pulsed laser beam 28 along the target tissue to provide for a plurality of data points, each data point having a location and intensity associated with it for imaging of the target tissue. In some embodiments, the raster scan is selected to deliver a sparse pattern in order to limit the patient's exposure, while still discerning a reasonable map of the intraocular targets. In order to image the target tissue, the treatment laser beam (i.e. the laser beam having the parameters suitably chosen as described above for the modification of tissue) is preferably attenuated to the nano-Joule level for imaging of the structures to be treated. When used for imaging, the attenuated laser beam may be referred to as an imaging beam. In many embodiments, the treatment beam and the imaging beam may be the same except that the pulse energy of the laser source is lower than the treatment beam when the laser beam is used for imaging. In many embodiments, the pulse energy of the laser beam when used for imaging is preferably from about 0.1 nJ to 10 nJ, preferably less than 2 nJ and more preferably less than 1.8 nJ. The use of the same laser beam for both treatment and imaging provides for the most direct correlation between the position of the focal locations for imaging and treatment—they are the same beam. This attenuated probe beam can is preferably used directly in a back reflectance measuring configuration, but, alternatively, may be used indirectly in a fluorescence detection scheme. Since increases in both back-scatter and fluorescence within tissue structures will be evident, both approaches have merit.

In a preferred embodiment, imaging of a first target area to be modified is performed sequentially with the modification of the tissue in the first target area before moving on to a second, different, target area, i.e. imaging is performed sequentially with treatment in a predetermined target area. Thus, for instance imaging of the lens capsule is preferably followed by treatment of the lens capsule before imaging is carried out on other either structures, such as the cornea or iris. In another embodiment, imaging of a first target area where a first incision to be place is performed sequentially with the scanning the treatment beam to perform the incision in the first target area before moving on to a second target area for performing a second incision, i.e. imaging of the area to be incised is performed sequentially with scanning the treatment beam to perform in the predetermined target area.

In another embodiment, a cataract procedure comprises a capsulotomy incision, and at least one of a cataract incision and a limbal relaxing incision. In one embodiment, imaging of the target tissue where the capsulotomy is to be performed is followed by scanning of the treatment to perform the capsulotomy, and then the treatment beam is scanned to perform the capsulotomy. Subsequently, imaging of the target tissue where the at least one of the cataract incisions (CI) and the limbal relaxing incision (LRI) is carried out and then the treatment beam is scanned to perform the at least one of the LRI and the CI. When an LRI is selected, this minimizes the chance for the patient to move between imaging and treatment for the LRIs which are the most critical/sensitive to eye movements between image and treatment.

As shown in the illustrated embodiment, the scanning assembly 18 can include a z-scan device 58 and a xy-scan device 60. The z-scan device 58 is operable to vary a convergence/divergence angle of the beam 28 and thereby change a location of the focal point in the direction of propagation of the beam 28. For example, the z-scan device 58 can include one or more lenses that are controllably movable in the direction of propagation of the beam 28 to vary a convergence/divergence angle of the beam 28. The xy-scan device 60 is operable to deflect the beam 28 in two dimensions transverse to the direction of propagation of the beam 28. For example, the xy-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown in the illustrated embodiment, a camera 62 and associated video illumination 64 can be integrated with the scanning assembly 18. The camera 62 and the beam 28 share a common optical path through the objective lens assembly 20 to the eye. A video dichroic 66 is used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

Figure 3:
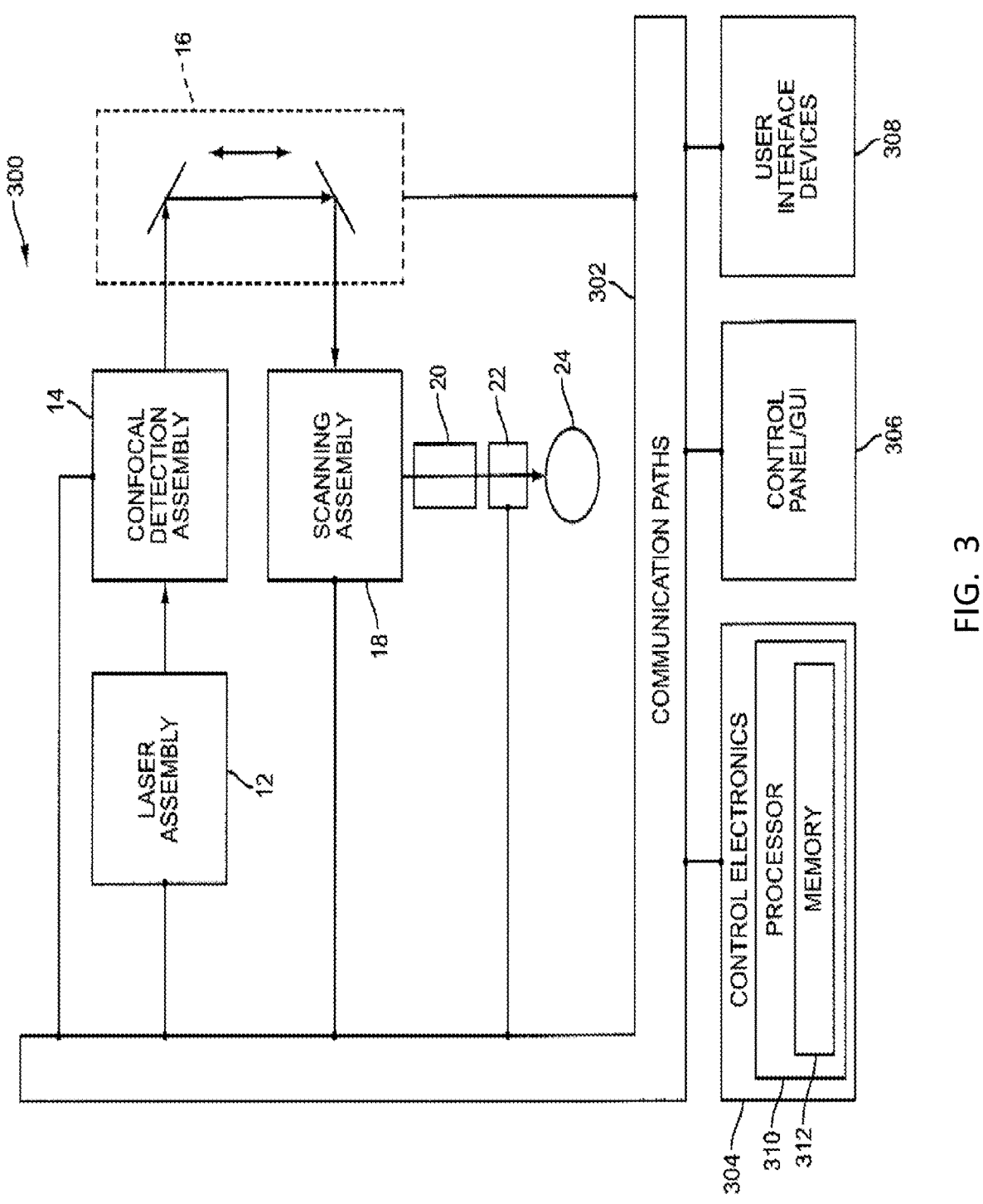
FIG. 3 is a schematic diagram of an embodiment of the laser surgery system of FIG. 1.

FIG. 3 schematically illustrates a laser surgery system 300, in accordance with many embodiments. The laser surgery system 300 includes the laser assembly 12, the confocal detection assembly 14, the shared optics 16, the scanning assembly 18, the objective lens assembly 20, the patient interface 22, communication paths 302, control electronics 304, control panel/graphical user interface (GUI) 306, and user interface devices 308. The control electronics 304 includes processor 310, which includes memory 312. The patient interface 22 is configured to interface with a patient 24. The control electronics 304 is operatively coupled via the communication paths 302 with the laser assembly 12, the confocal detection assembly 14, the shared optics 16, the scanning assembly 18, the control panel/GUI 306, and the user interface devices 308.

The scanning assembly 18 can include a z-scan device and a xy-scan device. The laser surgery system 300 can be configured to focus the electromagnetic radiation beam 28 to a focal point that is scanned in three dimensions. The z-scan device can be operable to vary the location of the focal point in the direction of propagation of the beam 28. The xy-scan device can be operable to scan the location of the focal point in two dimensions transverse to the direction of propagation of the beam 28. Accordingly, the combination of the z-scan device and the xy-scan device can be operated to controllably scan the focal point of the beam in three dimensions, including within a tissue of the patient 24 such as within an eye tissue of the patient 24. The scanning assembly 18 is supported by the shared optics 16, which may be configured to accommodate patient movement induced movement of the scanning assembly 18 relative to the laser assembly 12 and the confocal detection assembly 14 in three dimensions.

The patient interface 22 is coupled to the patient 24 such that the patient interface 22, the objective lens assembly 20, and the scanning assembly 18 move in conjunction with the patient 24. For example, in many embodiments, the patient interface 22 employs a suction ring that is vacuum attached to an eye of the patient 24. The suction ring can be coupled with the patient interface 22, for example, using vacuum to secure the suction ring to the patient interface 22.

The control electronics 304 controls the operation of and/or can receive input from the laser assembly 12, the confocal detection assembly 14, the free-floating assembly 16, the scanning assembly 18, the patient interface 22, the control panel/GUI 306, and the user interface devices 308 via the communication paths 302. The communication paths 302 can be implemented in any suitable configuration, including any suitable shared or dedicated communication paths between the control electronics 304 and the respective system components.

The control electronics 304 can include any suitable components, such as one or more processors, one or more field-programmable gate arrays (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 may be a non-volatile computer readable medium, and is coupled to the processor 310 in order to store data used by the processor and other system elements, and in many embodiments, to store one or more programs embodying one or more steps for carrying out the methods of the present invention. The processor 310 interacts with the other components of the system as described more fully throughout the present specification. In an embodiment, the memory 312 can include a look up table that can be utilized to control one or more components of the laser system surgery system 300.

The processor 310 can be a general purpose microprocessor configured to execute instructions and data, such as a Pentium processor manufactured by the Intel Corporation of Santa Clara, California. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 312 can be local or distributed as appropriate to the particular application. Memory 312 can include a number of memories including a main random access memory (RAM) for storage of instructions and data during program execution and a read only memory (ROM) in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input device suitable to provide user input to the control electronics 304. For example, the user interface devices 308 can include devices such as, for example, a touch-screen display/input device, a keyboard, a footswitch, a keypad, a patient interface radio frequency identification (RFID) reader, an emergency stop button, and a key switch.

The laser surgical techniques described herein a pulsed 320 nm to 430 nm laser to perform highly precise physical modifications of ocular targets, including tissues (such as lens, lens capsule, cornea, etc.) and synthetic intraocular lens implants. This can be done in two different operating regimes; with or without cavitation bubble formation. The sub-cavitation regime can also be used to modify the refractive index of ocular targets. Although the wavelengths used in the present invention are shorter or in the range than those associated with retinal blue light toxicity, the absorption of the 320 nm to 400 nm laser light within the aged lens further minimizes the risk of retinal damage, as this light will be absorbed by the lens volume. Furthermore, the risk of damaging the corneal endothelium or other corneal structures is also minimized. The threshold pulse energy will be $E_{th}=\Phi*d^2/4$, where $\Phi$ is the threshold radiant exposure and d is the focal spot diameter. Here, the focal spot diameter, d, is $d=\lambda F/D_b$ where $\lambda$ is the wavelength, F is the focal length of the last focusing element and $D_b$ is the beam diameter of the last lens. For stable and reproducible operation, pulse energy should exceed the threshold by at least a factor of 2; however, the energy level can be adjusted to avoid damage to the corneal endothelium.

The incident light of the laser used for the modification of the eye tissue generally has a wavelength of between 320 nm and 430 nm, preferably between 320 and 400 nm, preferably between 320 to 370 nm, and more preferably between 340 nm and 360 nm. In many embodiments, the laser light has a wavelength of 355 nm.

The pulse energy of laser pulses is generally between 0.01 μJ and 500 μJ. In many embodiments, the pulse energy will be between 0.1 μJ and 100 μJ, or more precisely, between 0.1 μJ and 40 μJ, or between 0.1 μJ and 10 μJ.

A pulse repetition rate of the laser pulses is generally between 500 Hz and 500 kHz. In many embodiments, the pulse repetition rate is between 1 kHz to 200 kHz, or between 1 KHz to 100 KHz.

Spot sizes of the laser pulses are generally smaller than 10 μm. In many embodiments, the spot size is preferably smaller than 5 μm, typically 0.5 μm to 3 μm.

A pulse duration of the laser pulses is generally between 1 ps and 100 ns. In many embodiments, the pulse duration is between 100 ps to 10 ns, or between 100 ps and 1 ns. In a preferred embodiment, the pulse duration is between 300 ps and 700 ps, preferably 400 ps to 700 ps.

In some embodiments, the beam quality, also referred to as $M^2$ factor, is between 1 and 1.3. The $M^2$ factor is a common measure of the beam quality of a laser beam. In brief, the $M^2$ factor is defined as the ratio of a beam's actual divergence to the divergence of an ideal, diffraction limited, Gaussian $TEM_{00}$ beam having the same waist size and location as is described in ISO Standard 11146.

A peak power density, obtained by dividing the peak power of the laser pulse by the focal spot size, is generally expressed in units of $GW/cm^2$. In general, the peak power density of the laser pulses should be sufficiently high to modify the ocular tissue to be treated. As would be understood by those ordinarily skilled, the peak power density depends upon a number of factors, including the wavelength of the selected laser pulses. In some embodiments, a peak power density is generally in the range of 100 $GW/cm^2$ to 800 $GW/cm^2$ will be used to cut ocular tissue with 355 nm light.

The scan range of the laser surgical system is preferably in the range of 6 to 10 mm.

In many embodiments for the modification of ocular tissue, spot spacing between adjacent laser pulses is typically in the range of about 0.20 μm to 10 μm, preferably 0.2 μm to 6 μm.

A numerical aperture should be selected that preferably provides for the focal spot of the laser beam to be scanned over a scan range of 6 mm to 10 mm in a direction lateral to a Z-axis that is aligned with the laser beam. The NA of the system should be less than 0.6, preferably less than 0.5 and more preferably in a range of 0.05 to 0.4, typically between 0.1 and 0.3. In some specific embodiments, the NA is 0.15. For each selected NA, there are suitable ranges of pulse energy and beam quality (measured as an $M^2$ value) necessary to achieve a peak power density in the range required to cut the ocular tissue. Further considerations when choosing the NA include available laser power and pulse rate, and the time needed to make a cut. Further, in selection of an appropriate NA, it is preferable to ensure that there is a safe incidental exposure of the iris, and other ocular tissues, that are not targeted for cuts.

Table 1 and Table 2, below, show typical laser beam parameters in accordance with many embodiments of the present invention.

TABLE 1

| wavelength (nm) | 355 | 355 | 355 | 355 | 355 | 355 |
|---|---|---|---|---|---|---|
| energy (uJ) | 1 | 4 | 2.25 | 9 | 0.36 | 1.44 |
| pulse rate (kHz) | 70 | 100 | 70 | 100 | 70000 | 100 |
| Pulse length (s) | 6.00E−10 | 6.00E−10 | 6.00E−10 | 6.00E−10 | 6.00E−10 | 6.00E−10 |
| NA (1/e^2) | 0.15 | 0.15 | 0.1 | 0.1 | 0.25 | 0.25 |
| M^2 (1/e^2) | 1.3 | 1 | 1.3 | 1 | 1.3 | 1 |
| spot spacing (μm) | 1 | 2 | 1.5 | 3 | 0.6 | 1.2 |
| theta (rad, 1/e^2) | 0.3 | 0.3 | 0.2 | 0.2 | 0.5 | 0.5 |
| BP (μm, 1/e^2) | 0.588 | 0.452 | 0.588 | 0.452 | 0.587 | 0.452 |
| SS (μm, 1/e^2) | 1.95 | 1.5 | 2.94 | 2.26 | 1.18 | 0.904 |
| area (mm^2, 1/e^2) | 3.01E−06 | 1.78E−06 | 6.77E−06 | 4.01E−06 | 1.08E−06 | 6.42E−07 |
| area (cm^2, 1/e^2) | 3.01E−08 | 1.78E−08 | 6.78E−08 | 4.01E−08 | 1.08E−08 | 6.42E−09 |
| peak energy density (J/cm^2) | 66.4 | 449 | 66.4 | 449 | 66.34 | 449 |
| peak power density (W/cm^2) | 1.E+11 | 7.E+11 | 1.E+11 | 7.E+11 | 1.E+11 | 7.E+11 |
| peak power density (GW/cm^2) | 111 | 748 | 111 | 748 | 111 | 748 |
| ratio to NS | 100% | 100% | 100% | 100% | 100% | 100% |
| average power (W) | 0.07 | 0.4 | 0.158 | 0.9 | 0.0252 | 0.144 |

TABLE 1-continued

| spots per mm^2 | 1,000,000 | 250,000 | 444,000 | 111,000 | 2,778,000 | 694,000 |
|---|---|---|---|---|---|---|
| time per pattern mm^2 (s) | 14.3 | 2.500 | 6.35 | 1.11 | 39.7 | 6.94 |
| average pattern energy density (J/cm^2) | 100 | 100 | 100 | 100 | 100 | 100 |
| relative possible iris safety limit (8*6T^.75 (J/cm^2)) | 353 | 95.4 | 192 | 51.9 | 758 | 205 |
| ratio energy density delivered/safety | 0.284 | 1.05 | 0.521 | 1.93 | 0.132 | 0.487 |

TABLE 2

| wavelength (nm) | 355 | 355 | 355 | 355 |
|---|---|---|---|---|
| energy (uJ) | 9 | 36 | 0.141 | 0.562 |
| pulse rate (Hz) | 70000 | 100000 | 70000 | 100000 |
| Pulse length (s) | 6.00E-10 | 6.00E-10 | 6.00E-10 | 6.00E-10 |
| NA (1/e^2) | 0.05 | 0.05 | 0.4 | 0.4 |
| M^2 (1/e^2) | 1.3 | 1 | 1.3 | 1 |
| spot spacing (μm) | 3 | 6 | 0.375 | 0.75 |
| theta (rad, 1/e^2) | 0.1 | 0.1 | 0.8 | 0.8 |
| BP (μm, 1/e^2) | 0.588 | 0.452 | 0.0588 | 0.452 |
| SS (μm, 1/e^2) | 5.88 | 4.52 | 0.735 | 0.565 |
| area (mm^2, 1/e^2) | 2.71E-05 | 1.61E-05 | 4.24E-07 | 2.51E-07 |
| area (cm^2, 1/e^2) | 2.71E-07 | 1.61E-07 | 4.24E-09 | 2.51E-09 |
| peak energy density (J/cm^2) | 66.4 | 449 | 66.4 | 449 |
| peak power density (W/cm^2) | 1.E+11 | 7.E+11 | 1.E+11 | 7.E+11 |
| peak power density (GW/cm^2) | 111 | 748 | 111 | 748 |
| ratio to NS | 100.00% | 100.00% | 100.00% | 100.00% |
| average power (W) | 0.63 | 3.6 | 0.00984 | 0.0563 |
| spots per mm^2 | 111,000 | 27,800 | 7,111,000 | 1,778,000 |
| time per pattern mm^2 (s) | 1.59 | 0.278 | 102 | 17.8 |
| average pattern energy density (J/cm^2) | 100.000 | 100.000 | 100.000 | 100.000 |
| relative possible iris safety limit (8*6 T^.75(J/cm^2)) | 67.9 | 18.4 | 154 | 416 |
| ratio energy density delivered/safety | 1.47 | 5.45 | 0.065 | 0.241 |

In Tables 1 and 2, theta is the divergence half-angle, BP is the beam parameter product, SS is the spot size, and the area is the area of the laser spot. Here, the $1/e^2$ width is equal to the distance between the two points on the marginal distribution that are $1/e^2=0.135$ times the maximum value.

In many embodiments, the laser eye surgery methods and/or laser eye surgery systems described herein are used in for maintaining iris exposures below a predetermined limit while making corneal incisions during a laser cataract surgery.

In cataract surgery, a capsulotomy incision, often in the form of a small round hole is formed in the anterior side of the lens capsule to provide access to the lens nucleus.

In addition, cataract surgery may include three types of cornea incisions: arcuate incisions, primary incisions ("primary cataract incisions", or "cataract incisions") and sideport incisions. Parameters that may be used to define the capsulotomy include shape (i.e. circular, elliptical, rectangular or polygonal) and size. The systems described herein are designed to receive these parameters based on user or physician's input and preferably, to provide a prompt for their input where not received.

Primary incisions and sideport incisions may have the same structure. They are generally multiplanar structures that create an opening that allow the physician access into the anterior chamber. The primaries are used for insertion of the aspiration tool and the insertion of the IOL. Sideport incisions may be used for inserting smaller instrumentation into the anterior chamber. The location and shape of both the primary incisions and the sideport incisions are determined by the user parameters and, optionally, by information from a section scan as described herein, where the cornea anterior and posterior surfaces may be modeled by circles. The anterior and posterior curvatures of the cornea as measured in the circular fits of the section scans may optionally be used to position the cuts. Parameters that may be used to define the primary cataract incision or the sideport incision are preferably selected from the group consisting of limbus offset, width; side cut angle, plane depth and length. The systems described herein are designed to receive these parameters based on user or physician's input and preferably, to provide a prompt for their input where not received.

Arcuate incisions may be used to correct a patient's astigmatism. For instance, they may adjust the curvature of the cornea to a more spherical shape by means relaxing stresses along the meridian on which they are placed. They are parts of a conical surface that crosses both the anterior and posterior surfaces of the cornea. In some embodiments, the anterior curvature and posterior curvature of the cornea, as measured in a circular fit to a section scan, are used to position an "along-the-cut" scan. The along-the-cut scan lays on the surface of a cone that transverses the cornea. The arcuate incision can be located within the along-the-cut scan. Parameter that may be used to define the arcuate incision may include the size of the optical zone, arc length, uncut anterior portion, uncut posterior portion and side cut angle. The systems described herein are designed to receive these parameters based on user or physician's input and preferably, to provide a prompt for their input where not received.

The laser surgery system 10 can be used to form any suitably shaped arcuate, primary or sideport incisions.

Figure 4A:
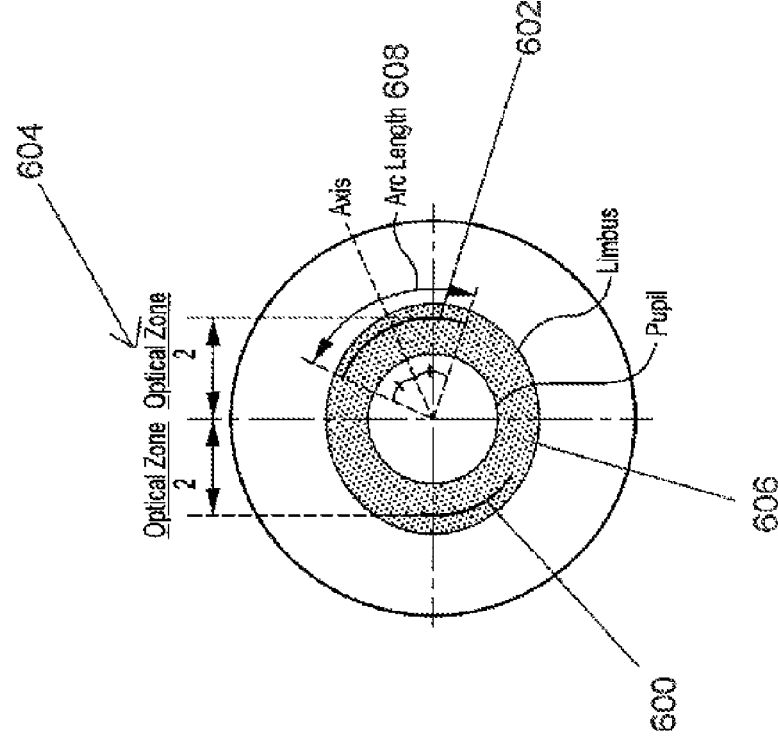
FIGS. 4A, 4B and 4C illustrate aspects of arcuate incisions of a cornea that can be formed by the laser surgery system of FIG. 1, in accordance with many embodiments.
Figures 4B, 4C:
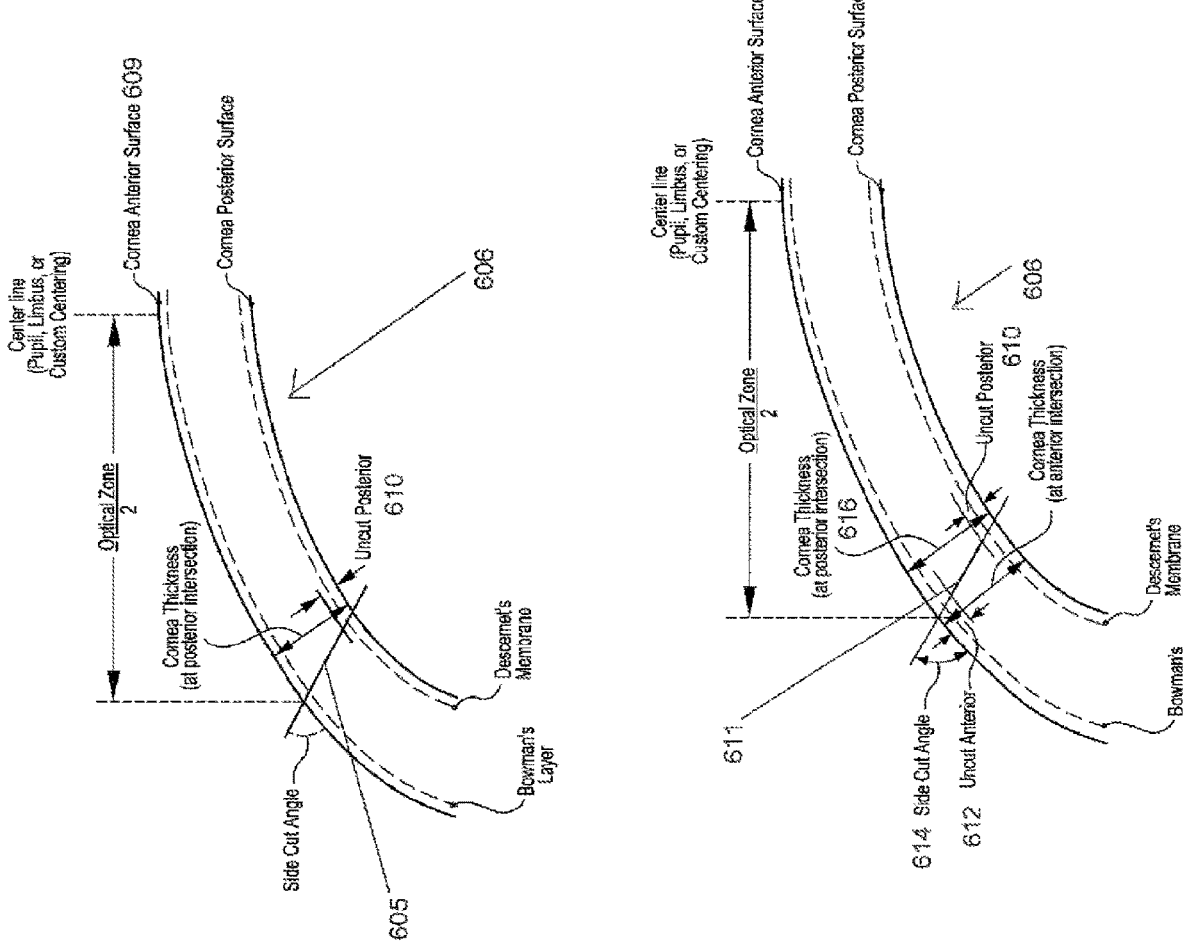

FIGS. 4A through 4C illustrate aspects of arcuate incisions of a cornea that can be formed by the laser surgery system 10, in accordance with many embodiments. FIG. 4A shows an en face view of arcuate incisions 600, 602 within the optical zone 604 of the cornea 606 that can be formed using the system 2. The optical zone 606 is user-adjustable within the range of 2 mm-11 mm. For asymmetric arcuate incisions, the optical zone 606 is independently adjustable for each incision. Arc length 608 is user-adjustable within the range of 10°-120°.

FIG. 4B shows a cross-sectional view of an arcuate incision 605 in the cornea 606 that can be formed using the system 2 and that penetrates the cornea anterior surface 609 and has an uncut posterior portion 610. FIG. 4C shows a cross-sectional view of an arcuate intrastromal incision 611 in the cornea 606 that can be formed using the system 2. The arcuate intrastromal incision 611 has an uncut anterior portion 612 and an uncut posterior portion 610. Side cut angle 614 is user-adjustable within the range of 30°-150°. Uncut posterior and anterior portions 610, 612 are user-adjustable within the range of 100 µm-250 µm or 20%-50% of the cornea thickness. Cornea thickness is measured at the projected intersection of the incision with the cornea anterior/posterior measured at 90° to anterior/posterior cornea surface regardless of what side cut angle 614 is chosen.

Figures 5A, 5B:
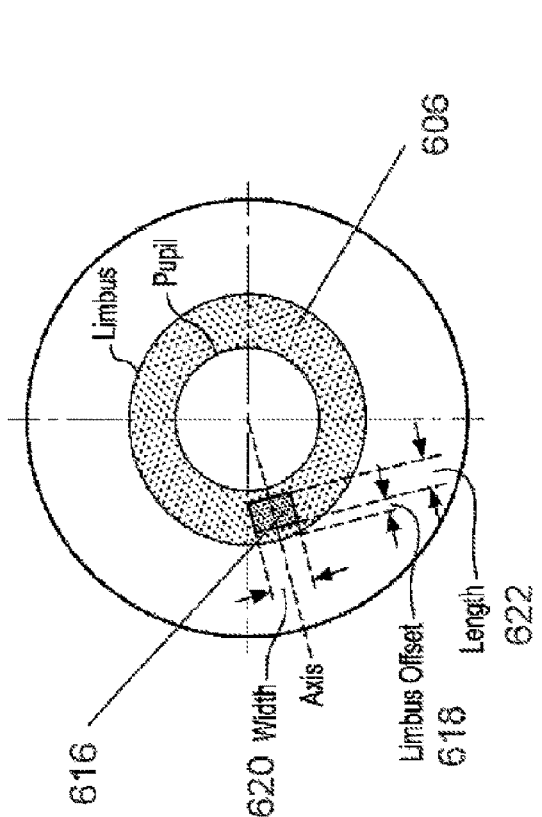
FIGS. 5A, 5B, 5C, 5D, 5E and 5F illustrate aspects of primary cataract surgery access incisions of a cornea that can be formed by the laser surgery system of FIG. 1, in accordance with many embodiments.
Figures 5C, 5D:
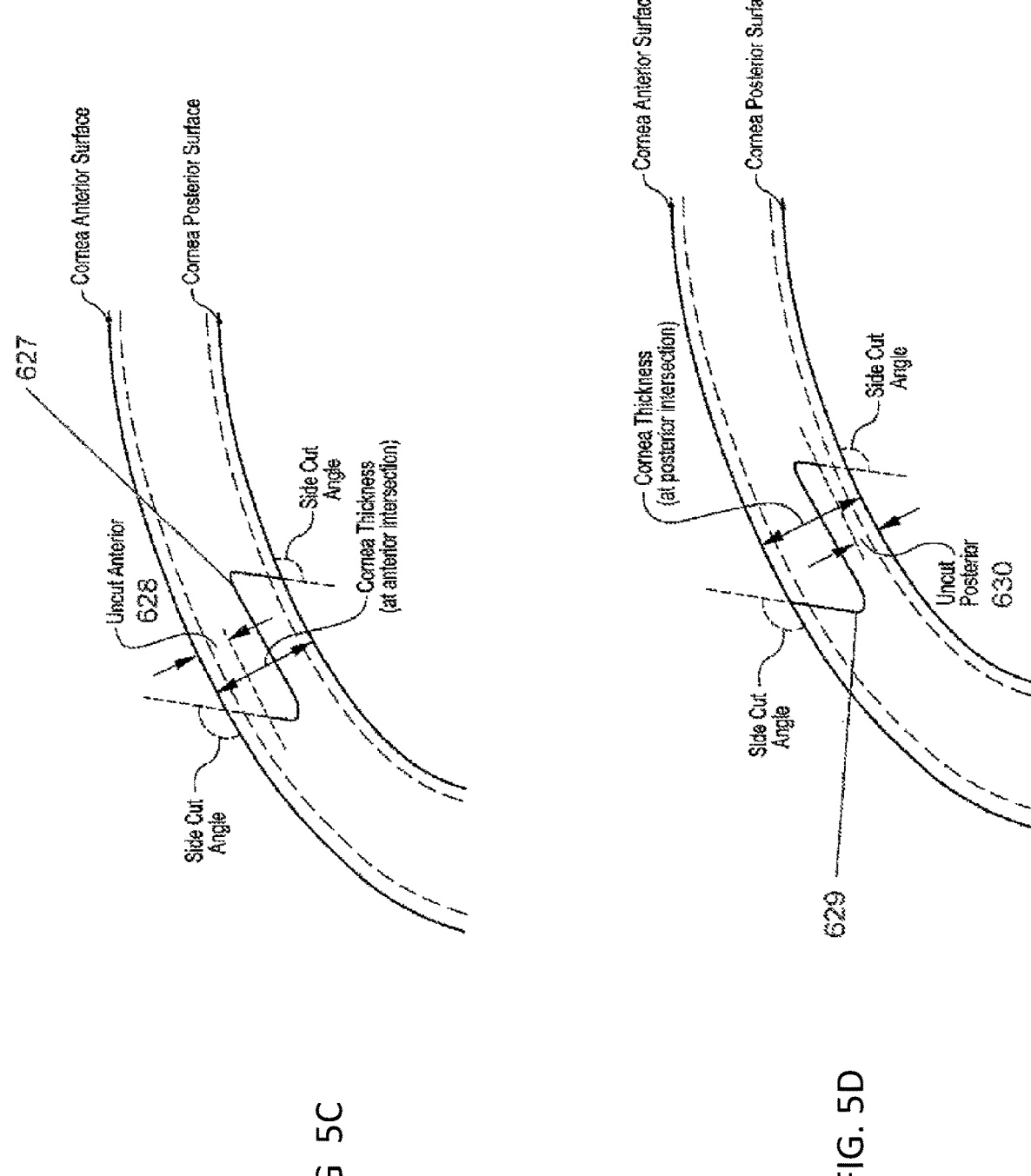
Figures 5E, 5F:
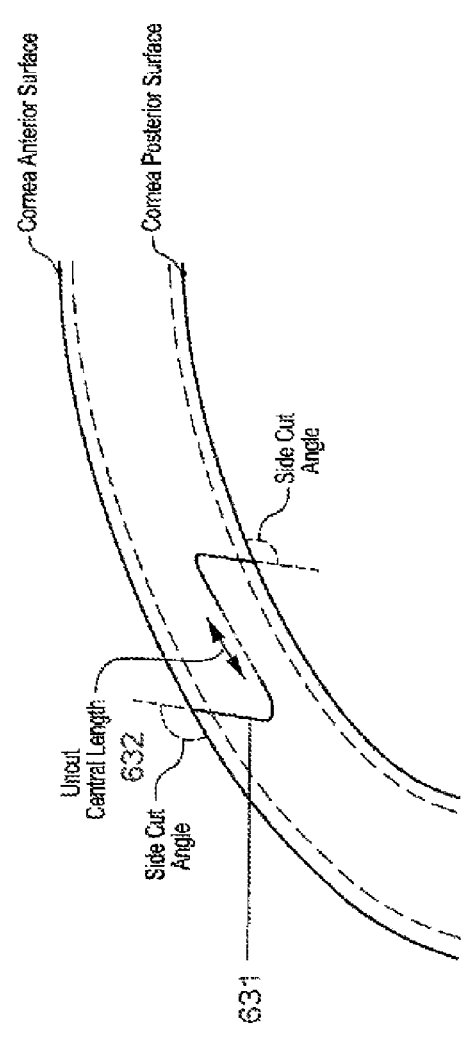

FIG. 5A shows an enface view of a primary cataract incision 616 in the cornea 606 that can be formed using the system 2. The primary cataract incision 616 provides access to surgical tools used to, for example, remove the fragmented crystalline lens nucleus and insert an IOL. FIG. 5B shows a cross-sectional view of a primary cataract incision 617 of the cornea 606 that can be formed using the system 2. Limbus offset 618 is user-adjustable within the range of 0.0 mm-5.0 mm. Width 620 is user-adjustable within the range 0.2 mm-6.5 mm. Length 622 is user-adjustable within the range of 0.5 mm-3.0 mm. Side Cut Angle 624 is user-adjustable within the range of 30°-150°. Plane depth 626 is user-adjustable within the range of 125 µm-375 µm or 25%-75% of the cornea thickness. Length 622 is defined as the enface view distance between the projected incision intersection with the cornea anterior and the cornea posterior. FIG. 5C shows a cross-sectional view of a primary cataract incision 627 that includes an uncut anterior portion 628. FIG. 5D shows a cross-sectional view of a primary cataract incision 629 that includes an uncut posterior portion 630. FIG. 5E shows a cross-sectional view of a primary cataract incision 631 that includes an uncut central length 632. And FIG. 5F shows a cross-sectional view of a primary cataract incision 634 that includes no uncut portion. Side Cut Angle 636 is user-adjustable within the range of 30°-150°. Uncut central length 632 is user-adjustable within the range of 25 µm-1000 µm.

Figure 6A:
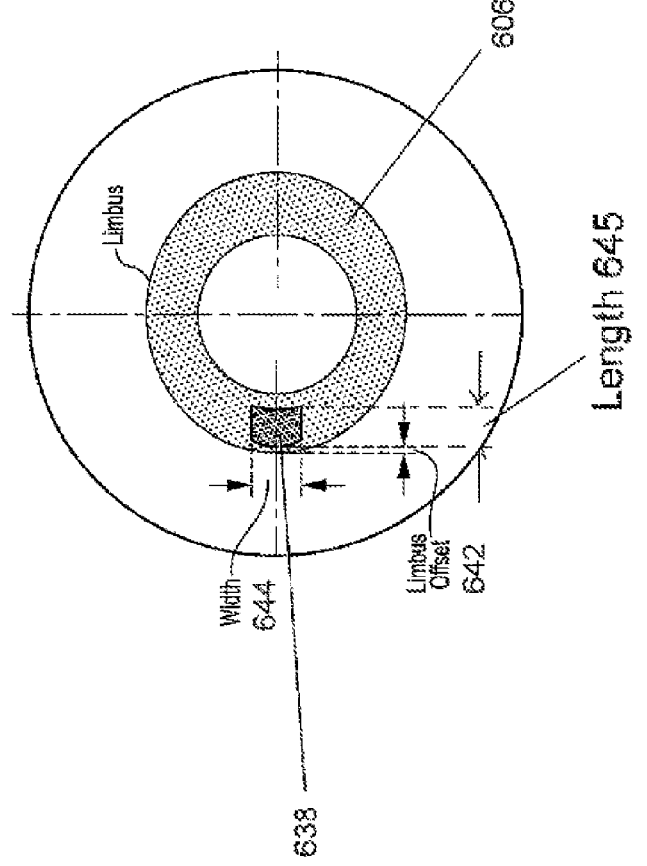
FIGS. 6A, 6B, 6C, 6D and 6E illustrate aspects of sideport cataract surgery access incisions of a cornea that can be formed by the laser surgery system of FIG. 1, in accordance with many embodiments.
Figures 6B, 6C:
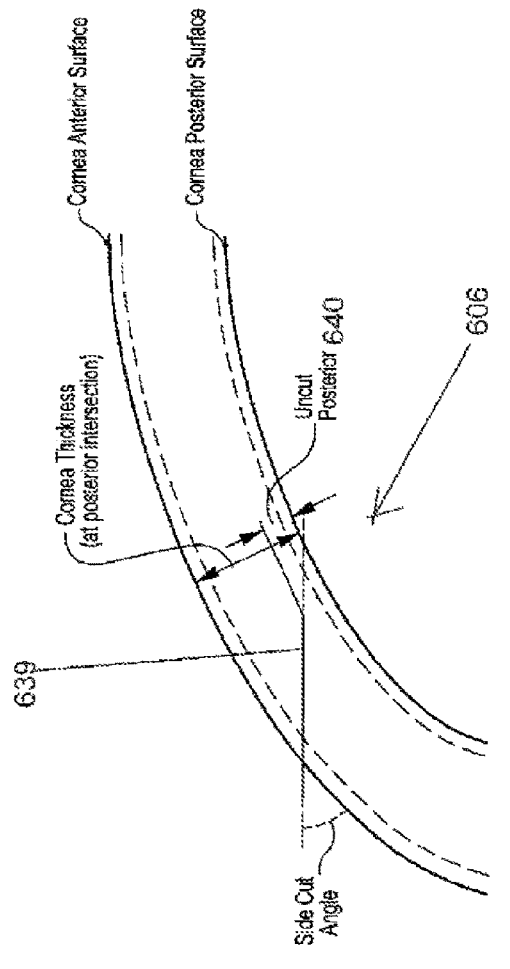
Figures 6D, 6E:
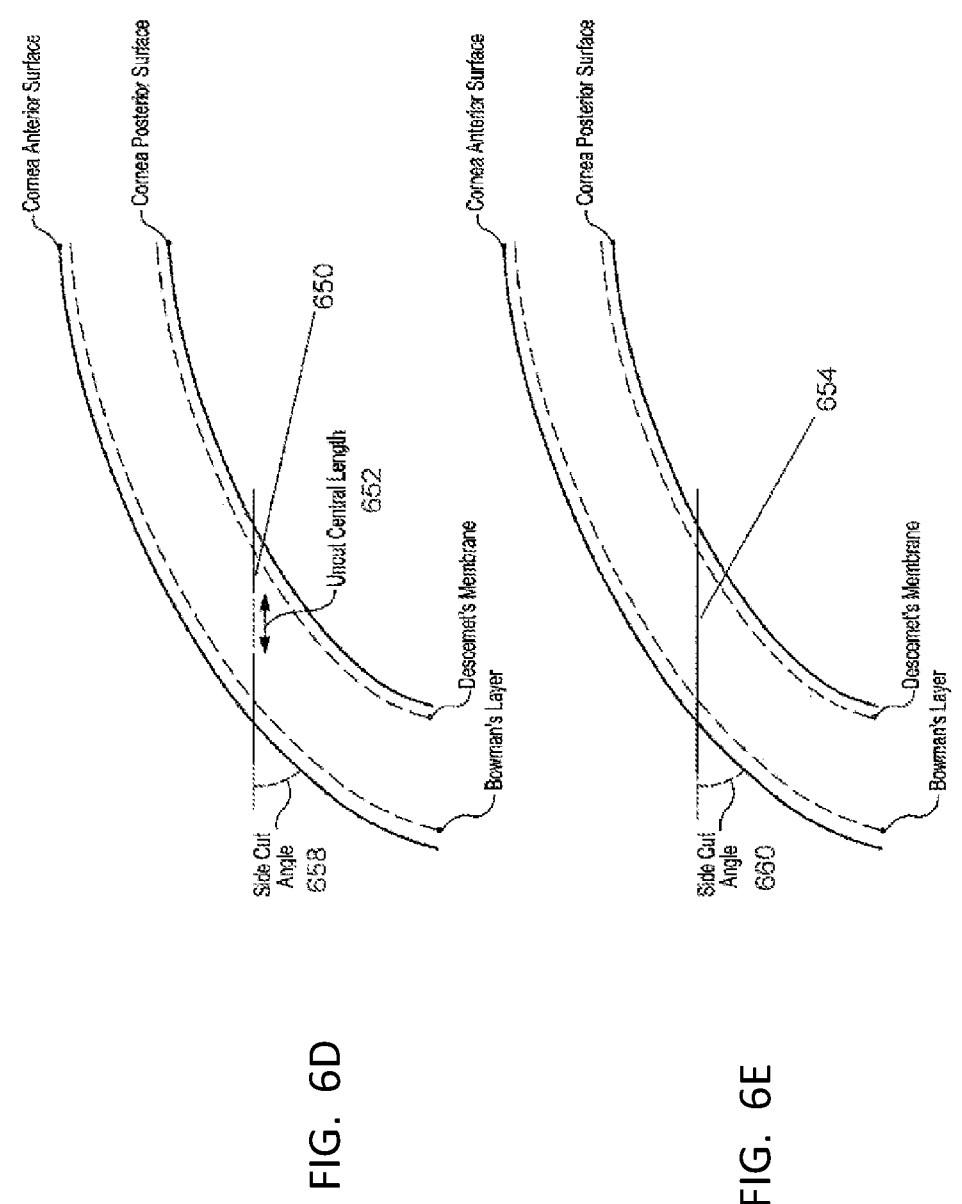

FIG. 6A shows an enface view of a sideport cataract incision 638 in the cornea 606 that can be formed using the system 2. The sideport cataract incision 638 provides access for surgical tools used, for example, to assist in the removal of the fragmented crystalline lens. FIG. 6B shows a cross-sectional view of a sideport cataract incision 639 of the cornea 606 that has an uncut posterior portion 640 and can be formed using the system 2. Limbus offset 642 is user-adjustable within the range of 0.0 mm-5.0 mm. Width 644 is user-adjustable within the range 0.2 mm-6.5 mm. Length 645 is user-adjustable within the range of 0.5 mm-3.0 mm. FIG. 6C shows a cross-sectional view of a sideport cataract incision 646 that includes an uncut anterior portion 648. FIG. 6D shows a cross-sectional view of a sideport cataract incision 650 that includes an uncut central length 652. And FIG. 6E shows a cross-sectional view of a sideport cataract incision 654 that includes no uncut portion. Side Cut Angle 656, 658, 660 is user-adjustable within the range of 30°-150°. Uncut central length 652 is user-adjustable within the range of 100 µm-250 µm or 20%-50% of the cornea thickness. Cornea thickness 662 is measured at the projected intersection location of the incision with the cornea anterior/posterior measured at 90° to the anterior/posterior cornea surface regardless of what side cut angle is chosen.

TABLE 3

User-adjustable parameters for arcuate incisions.

| Feature | Default* | Range | Increment | Step Size | Units |
|---|---|---|---|---|---|
| Incision Type | N/A | Single, Symmetric, Asymmetric | N/A | 0.5 | N/A |
| Axis** | N/A | 0-360 | 1 | 2.5 | ° |
| Optical Zone** | N/A | 2-11 | 0.1 | 10 | mm |
| Arc Length** | N/A | 10-120 | 1 | 0.5 | ° |
| Centering Method | N/A | Pupil, Limbus, Custom | N/A | 0.5 | N/A |
| Penetration Type | Anterior | Anterior or Intrastromal | N/A | N/A | N/A |
| Depth Units | Percentage | Percentage or Absolute | N/A | N/A | N/A |
| Uncut Anterior*** | 20% | 20-50% | 1 | 2 | % |
|  | 100 | 100-250 | 1 | 10 | µm |
| Uncut Posterior | 20% | 20-50% | 1 | 2 | % |
|  | 100 | 100-250 | 1 | 10 | µm |
| Side Cut Angle | 90 | 30-150 | 1 | 5 | ° |
| Horizontal Spot Spacing | 4 | 2-10 | 1 | 1 | µm |
| Vertical Spot Spacing | 10 | 1-25 | 1 | 1 | µm |
| Pulse Energy | 2 | 1~4 | 0.1 | 0.1 | µJ |

*Parameters do not have default values; user must select each parameter.
**Independently adjustable parameters for asymmetric incisions.
***Not applicable for anterior penetrating.

TABLE 4

User-adjustable parameters for primary cataract incisions.

| Feature | Default* | Range | Increment | Step Size | Units |
|---|---|---|---|---|---|
| Axis | N/A | 0-360 | 1 | 5 | ° |
| Limbus Offset | N/A | 0.0-5.0 | 0.1 | 0.1 | mm |
| Width | 2.2 | 0.2-6.5 | 0.1 | 0.1 | mm |
| Length | 2.2 | 0.5-3.0 | 0.1 | 0.1 | mm |
| Uncut Region | Central | Anterior, Central, Posterior, None | N/A | N/A | N/A |
| Depth Units | Percentage | Percentage or Absolute | N/A | N/A | N/A |
| Uncut Anterior/ Uncut Posterior | 20% / 100 | 20-50% / 100-250 | 1% / 1 | 5% / 25 | % / µm |
| Uncut Central Length* | 100 | 25-1000 | 1 | 25 | µm |
| Plane Depth | 50% / 250 | 25-75% / 125-375 | 1% / 1 | 5% / 50 | % / µum |
| Side Cut Angle | 120 | 30-150 | 1 | 5 | ° |
| Horizontal Spot Spacing | 10 | 2-10 | 1 | 5 | µ |
| Vertical Spot Spacing | 20 | 1-25 | 1 | 5 | µm |
| Pulse Energy | 5 | 1-4 | 0.1 | 0.5 | µJ |

*If the uncut central length is longer than the length parameter, then the uncut central length will be set as equal to the length parameter.

TABLE 5

User-adjustable parameters for sideport cataract incisions.

| Feature | Default* | Range | Increment | Step | Units |
|---|---|---|---|---|---|
| Number of Incisions | N/A | 0~6 | 1 | 1 | N/A |
| Axis* | N/A (0) | 0-360 | 1 | 5 | ° |
| Limbus Offset* | N/A (1.0) | 0.0-5.0 | 0.1 | 0.1 | mm |

21

TABLE 5-continued

User-adjustable parameters for sideport cataract incisions.

| Feature | Default* | Range | Increment | Step | Units | |
|---|---|---|---|---|---|---|
| Width* | N/A | (0.5) | 0.2-6.5 | 0.1 | 0.1 | mm |
| Uncut Type | Central | Anterior, Central, Posterior, None | N/A | N/A | N/A | |
| Uncut Units | Percentage | Percentage or Absolute | N/A | N/A | N/A | |
| Uncut Length | 20% | 20-50% | 1% | 2% | % | |
| (Anterior, | 100 | 100-250 | 1 | 10 | μm | |
| Posterior, | Lens Apex | Cornea | N/A | N/A | N/A | |
| Side Cut | | Posterior | | | | |
| Angle Type | | Apex, | | | | |
| | | AC Center, | | | | |
| | | Lens Apex, | | | | |
| | | Lens Center, | | | | |
| | | Custom | | | | |
| Custom Side Cut Angle | 90 | 30-150 | 1 | 5 | ° | |
| Horizontal Spot Spacing | 10 | 2-10 | 1 | 5 | μm | |
| Vertical Spot Spacing | 20 | 1-25 | 1 | 5 | μm | |
| Pulse Energy | 5 | 1-4 | 0.1 | 0.5 | μJ | |

Although many different imaging techniques may be used in different embodiments, a combination of video/camera imaging and confocal imaging based on pulsed laser raster scanning of the tissue to be treated is preferred.

As illustrated in the embodiment of FIG. 2, video imaging of the tissue to be treated, preferably a human eye, can be achieved by a camera 62 and associated video illumination 64 integrated with the scanning assembly 18. The camera 62 and the beam 28 share a common optical path through the objective lens assembly 20 to the eye. A video dichroic 66 is used to combine/separate the beam 28 with/from the illumination wavelengths used by the camera. In one embodiment, the beam 28 can have a wavelength of between 320 and 370 nm, preferably about 355 nm, and the video illumination 64 can be configured to emit illumination having wavelengths greater than 370 nm, or more than 400 or more than 450 nm. Accordingly, the video dichroic 66 can be configured to reflect the beam between 320 and 370 nm while transmitting wavelengths greater than 370 nm, thus facilitating video imaging of the eye without interference from beam 28. The location of the capsulotomy incision and any corneal incision specified by the physician can be projected onto the video image prior to treatment as expected scan locations for each respective incision.

In many embodiments, the imaging of the eye 24 further includes confocally imaging one or more portions of the tissue, preferably the eye, to be treated. Any suitable device, assembly, and/or system, such as described herein, can be used to confocally image one or more portions of the eye or other tissue to be imaged. The confocal imaging methods used herein generally include using a beam source, preferably a pulsed laser source, to generate an electromagnetic radiation beam; propagating the electromagnetic radiation beam to a scanner along an optical path to the eye; focusing the electromagnetic radiation beam to a focal point at a location within the eye; using the scanner to scan, preferably raster scan, the focal point to different locations within the eye; propagating a portion of the electromagnetic radiation beam reflected from the focal point location back along the shared optical path to a sensor; and generating an intensity signal indicative of the intensity of a portion of the electromagnetic radiation beam reflected from the focal point location and propagated to the sensor. The method can include modifying polarization of at least one of the electromagnetic radiation beam and a portion of the electromagnetic radiation beam reflected from the focal point location. The method can include using the polarization-sensitive device to reflect a portion of the electromagnetic radiation beam reflected from the focal point location so as to be incident upon the sensor.

Based on the calibration of the system described herein, the focal point location of the confocally detected light can be related to the physical location of the focal point within the eye, and the location within the eye and the magnitude of the intensity at each location can be used to identify boundaries, edges and layers within the eye. Boundaries, edges and layers may be located in a confocal image by, for instance, Delaunay triangulation and Dijkstra segmentation. These confocal images, including the boundaries, edges and layers can then be displayed to a user as a graphical representation of the areas of the eye to be treated.

In many embodiments, the lens capsule, and optionally a portion or the entire lens, is imaged using confocal imaging, and preferably, these portions include the area of the lens capsule where the capsulotomy will be placed. In general, the parameters necessary to define the capsulotomy are input by a user or physician, and a raster scan with a pulsed laser beam sweeps through the relevant portion of the lens capsule for imaging the lens capsule. Based on the recorded location and magnitude of the confocally reflected intensity measurements at each location, the capsule is identified by image recognition, such as by Delaunay triangulation and Dijkstra segmentation, and the capsule shape is fit to the segmented image. The resulting confocal image of lens may then be shown to the physician for use in visualizing the capsulotomy incision.

In many embodiments, the methods and systems may include confocally imaging a cornea by scanning one or more of portions of the cornea where a primary incision, sideport incision or arcuate incision is to be placed. In a preferred embodiment, one sectional image of the cornea is performed for each selected corneal incision. These images are preferably in the form of a section scan. A section scan crosses cornea along plane and measures the confocal intensity at every location of a pulsed laser during the scan. Preferably, a section scan comprises a raster scan of a pulsed laser beam along the cornea including the anterior surface and posterior surface, on a vertical plane centered at the cornea incision center and oriented along an incision's meridian. The trajectory goes from deep to shallow, inside the eye, crossing the cornea. The posterior and anterior boundaries of the cornea may be identified in the image by, for instance, Dijkstra segmentation of the image, and the resulting image may be provided to the user.

If the selected corneal incision is an arcuate incision, an "along-the-cut" imaging scan is also preferably performed. An along-the-cut imaging scan may assist a physician in choosing the correct location for the arcuate incision in order to maintain an adequate depth and avoid posterior penetration. The "along the cut" scan preferably has the same conical shape as the arcuate incision and is inclusive of the entire area to be covered arcuate incision. The conical sector in the "along the cut" scan is mapped into a rectangular domain 520 defined by the conical coordinates. The resulting conical image is segmented and fit. Optionally, the resulting fits to the anterior and posterior surfaces of the cornea are used to construct the arcuates, which can then be overlaid on their sections and "along the cut" scans.

In many embodiments, the optical surface of the eye is fit with one or more with one or more of a Fourier transform, polynomials, a spherical harmonics, Taylor polynomials, a wavelet transform, or Zernike polynomials. The optical tissue surface may comprise one or more of the anterior surface of the cornea, the posterior surface of the cornea, the anterior surface of the lens capsule, the posterior surface of the lens capsule, an anterior surface of the lens cortex, a posterior surface of the lens cortex, an anterior surface of the lens nucleus, a posterior surface of the lens nucleus, one or more anterior surfaces of the lens having a substantially constant index of refraction, one or more posterior surfaces of the lens having a substantially constant index of refraction, the retinal surface, the foveal surface, a target tissue surface to correct vision such as a target corneal surface, an anterior surface of an intraocular lens, or a posterior surface of an intraocular lens, for example.

After the relevant portions of the ocular tissue, including the cornea, have been imaged, the incisions defined by the physician parameters may be projected onto the image, and a treatment scan of the laser light beam is generated. Here, the treatment scan refers to a simulated scan pattern, not an actual scan of the laser pulses in the eye tissue. The treatment scan preferably consists of a continuous set of x, y, z points arranged in space that are designed to carry out the incisions defined by the user. The locations of the treatment scans are projected onto at least one of the video and confocal images in order to define the set of expected scan locations of the incisions. The treatment scans according to the invention generally take the form of a raster scan of the ocular tissue to be incised.

In many embodiments, the present invention is directed to maintaining an exposure on the iris caused by scanning a pulsed laser beam in a pattern according to a treatment below a predetermined iris exposure limit.

The predetermined iris exposure limit is preferably set at a value below an iris exposure that will cause damage to the iris tissue. A number of different manners of establishing exposure limits are known in the art, and the systems and methods of the present invention can be suitably used with any known model for an exposure limit. In many, the predetermined exposure limit will be dependent on an exposure time of the iris to the incident radiation.

In some embodiments, the iris exposure limit ($E_L$) is a percentage of an Exposure ($E_{MVL}$, in J/cm$^2$) causing a Minimal Visible Lesion (MVL) in the iris, which may be determined experimentally and/or calculated theoretically. Specifically, the iris exposure limit, $E_L$, can be defined by the formula:

$$E_L = c*E_{MVL}, \text{ where } c \leq 1.$$

The variable c can be chosen based on a desired safety margin below the $E_{MVL}$. In some embodiments, c may be 0.9 or less, 0.8 or less, 0.7 or less, 0.6 or less, 0.50 or less, 0.40 or less, 0.3 or less, 0.2 or less, or 0.10 or less. Preferably, a value of c chosen is based, at least in part, on the uncertainty of the data that establishes $E_{MVL}$. The larger the uncertainty of $E_{MVL}$, the smaller the value of c that is appropriate to use. Preferably, values of c are less than 0.5.

Figure 20:
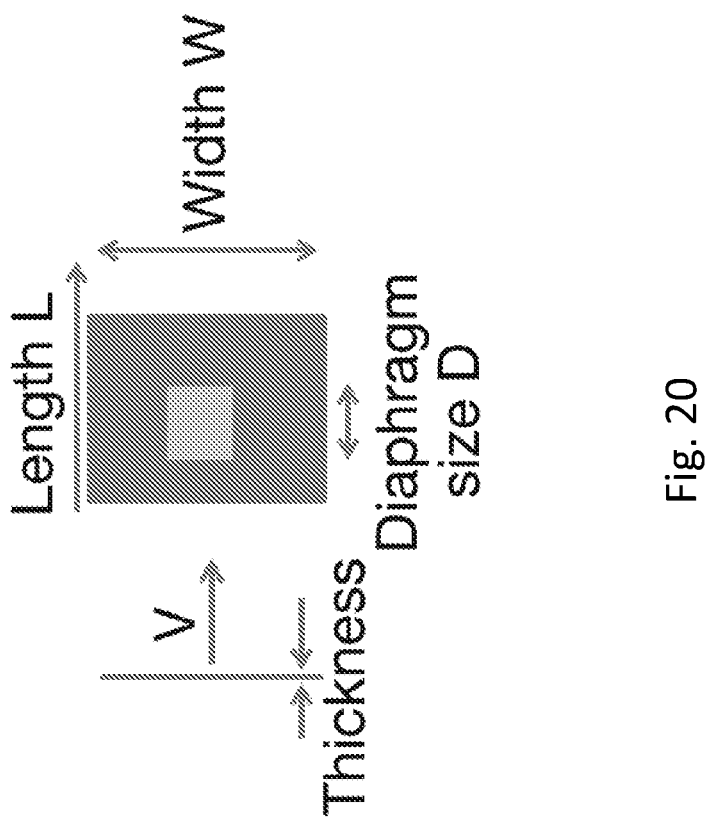
FIG. 20 is a graphical illustration of an integrating aperture.
Figure 21:
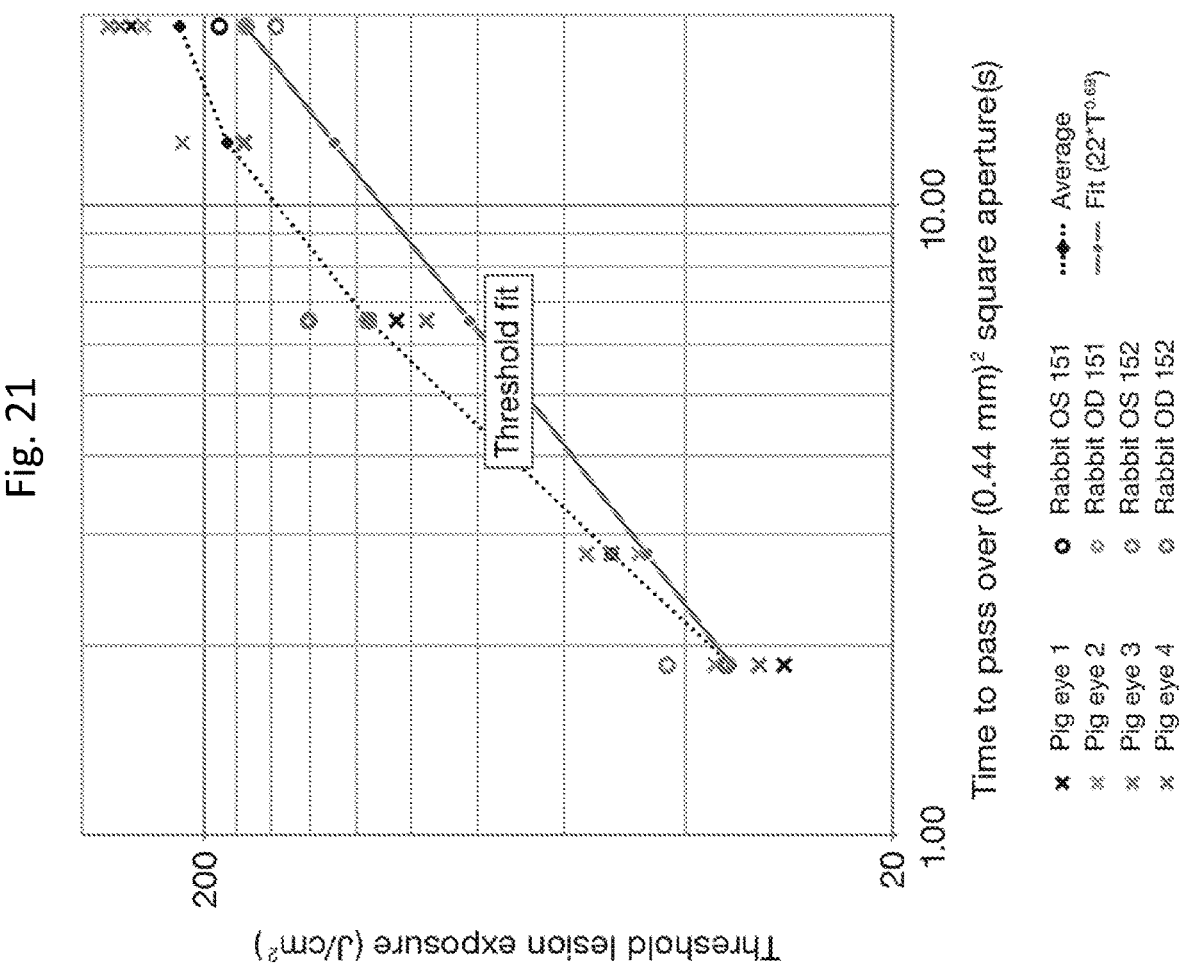
FIG. 21 is a graph of the Time to pass over a square aperture vs. Threshold Lesion Exposure (J/cm²).
Figure 22:
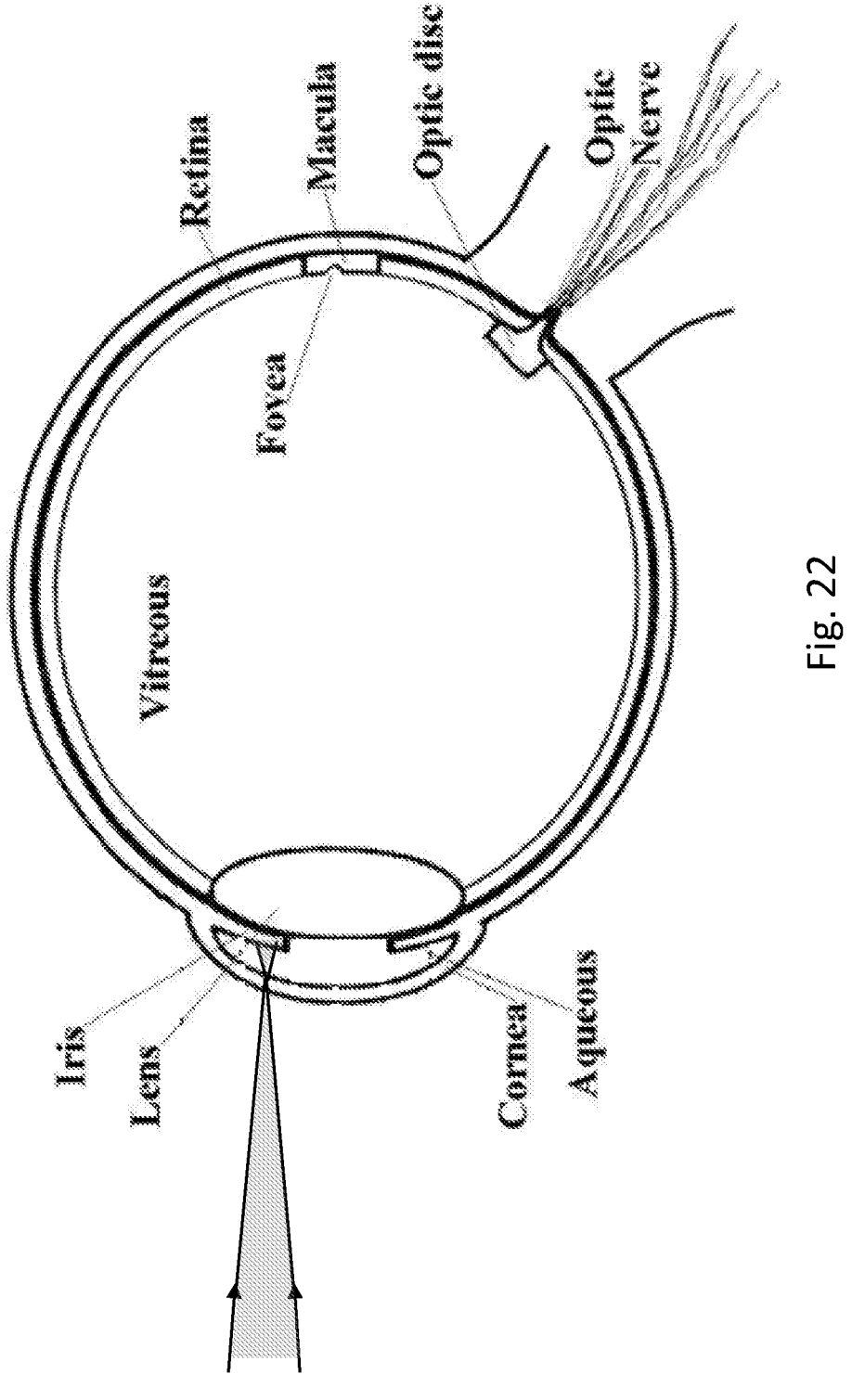
FIG. 22 is a schematic diagram illustrating an image of the eye having an electromagnetic beam focused on a portion of the cornea of the eye.

In many embodiments, $E_{MVL}$ is an exposure (preferably in J/cm$^2$) expressed as a function of an exposure time of an integrating aperture having a specified size. In many embodiments, the integrating aperture for the iris is the area of the integrating aperture specified for the Group 2 anterior chamber limit from ISO15004, (0.5 mm diameter) as the most appropriate aperture for the iris. In many embodiments, the area of this aperture is converted to a square aperture of the same area as the 0.5 mm diameter circular aperture, which is a square of approximately 0.44 mm×0.44 mm (FIG. 20). This square aperture is then used for the minimum visible lesion threshold function. The exposure time for an integrating aperture of the square aperture is determined to find the threshold exposure from the function. The data over the time region of interest is preferably fit by least squares fit of the data at the appropriate time points (see below, 1.86 s and 19.23 s, rabbit only), which allows the $E_{MVL}$ as a function of time to be conservatively expressed as:

$$E_{MVL}(T) = aT^b \text{J/cm}^2 \tag{Formula II}$$

and $$E_L = c*E_{MVL}(T) = acT^b, \text{ where } c \leq 1. \tag{Formula III}$$

where T is the time for the scanned pattern to pass over selected integration aperture, and parameters a and b are the best fit parameter from the data. The parameter, b, may be 0.75.

In some embodiments, $E_{MVL}$ as a function of time is expressed as Formula II.

$E_{MVL}$ as a function of time is expressed as Formula III.

Iris exposure limits are typically based on the use of an integration aperture arranged over the region to be exposed. In general, these safe exposure limits place an upper limit on the amount of power that can be pumped into the integration aperture over a time period. As a result, the safety limits are predicated on delivering a permissible amount of power, W, in a certain amount of time, T.

Iris exposures during laser surgery are maintained below a predetermined exposure limit according to at least two different strategies: (1) in a first embodiment, laser surgical methods and systems safely deliver a predetermined amount of power in a treatment scan by controlling the time over which the power is delivered to the ocular tissue; and (2) in a second embodiment, laser surgical methods and systems safely deliver a predetermined power by modifying one or more incision parameters, thereby limiting the power delivered during the planned incision.

Thus, in some embodiments of the present invention, the energy associated with a planned treatment scan is maintained below a predetermined exposure level by extending the time of the treatment scan by adding one or more treatment scan modifying elements so as to cause the iris exposure to be smaller than the predetermined exposure limit.

A system for cataract surgery on an eye of a patient according to this embodiment comprises: a laser assembly for generating a pulsed laser treatment beam; an imaging system configured for imaging an ocular tissue of the patient, the ocular tissue comprising corneal tissue; an optical scanning system configured for positioning the focal zone of the treatment beam to targeted locations of the ocular tissue, the targeting locations including a location in the corneal tissue; and a computer control system operatively coupled to the laser assembly, the imaging system, and the optical scanning system. The computer control system is programmed to: a) generate an initial treatment scan and an initial iris exposure corresponding to the initial treatment scan; b) determine whether the initial iris exposure is less than a predetermined exposure limit; c) generate a revised treatment scan comprising one or more treatment scan modifying elements when the initial iris exposure is greater than the predetermined exposure limit, wherein the one or more treatment scan modifying elements cause the iris exposure to be smaller than the predetermined exposure limit; and d) operate the optical scanning system and laser assembly to direct a treatment beam in a pattern corresponding to the revised treatment scan so as to create a corneal incision. The acts of step (d) may be performed automatically or may require additional actions by a user. In some embodiments, the system automatically delivers the treatment in some embodiments. In other embodiments, the methods and systems of the present invention require some additional act by a user (such as a physician) in order to initiate delivery of the treatment beam. For instance, the system may preferably be configured to provide a message or warning through, for instance, a graphical user interface, to a user that a revised treatment scan has been determined and may be delivered to the patient. The system may require that a user manually command delivery of the treatment scan once an acceptable scan has been determined. The system may require that the user press a button, peddle, lever or other device to initiate scan. In some embodiments, it may be preferable that a user be required to continually depress a button, lever, peddle or other device throughout a procedure to initiate and maintain delivery of the treatment scan from initiation to completion. In some embodiments, a user may be required to enter a command via a graphical user interface in order to initiate a treatment scan.

A laser surgical method for performing a corneal incision while maintaining iris exposure below a predetermined exposure limit according to this embodiment comprises: determining an initial iris exposure based on an initial treatment scan, the treatment scan corresponding to a predetermined corneal incision, determining whether the initial iris exposure is less than the predetermined exposure limit; generating a revised treatment scan comprising one or more treatment scan modifying elements when the initial iris exposure is greater than the predetermined exposure limit, and scanning the focal zone of a pulsed laser beam according to the revised treatment scan, thereby performing the corneal incision, wherein the one or more treatment scan modifying elements causes the iris exposure to be smaller than the predetermined exposure limit.

Certain steps to be carried out in a method or performed by a system according to this embodiment are shown in FIG. 7A. These include a step 402 of receiving a parameter set defining a corneal incision. The values of the parameter are generally set by a physician or other user. In many embodiments, the corneal incisions to be carried out according to the methods and systems of the present invention are selected from the group consisting of an arcuate incision, a primary cataract incision and sideport incision. The parameters that can be used to define these incisions, together with default and permissible values of each incision are shown in Tables 3, 4, 5 and FIGS. 4A-4C, 5A-5F, and 6A-6E respectively and in the related text. The parameter sets used to define incisions preferably include the pulse energy of the pulsed laser beam, the horizontal spot spacing and the vertical spot spacing.

A step 404 comprises obtaining image data of an area of the cornea corresponding to the incision location. In some embodiments, the image data may be obtained by optical coherence tomography imaging or confocal imaging. As indicated above, many embodiments include confocally imaging a cornea by scanning one or more of portions of the cornea where a primary incision, sideport incision or arcuate incision is to be placed. In a preferred embodiment, one sectional image of the cornea is performed for each selected corneal incision. These images are preferably in the form of a section scan. A section scan crosses cornea along plane and measures the confocal intensity at every location of a pulsed laser during the scan. Preferably, a section scan comprises a raster scan of a pulsed laser beam along the cornea including the anterior surface and posterior surface, on a vertical plane centered at the cornea incision center and oriented along an incision's meridian. The trajectory goes from deep to shallow, inside the eye, crossing the cornea.

A step 406 according this embodiment comprises, projecting the defined corneal incision on the image date to generate an Initial Treatment Scan. The Initial Treatment Scan is a simulated scan and is not actually delivered to the patient. The initial treatment scan preferably comprises of a continuous set of x, y, z points arranged in space that are designed to carry out the incisions defined by the user. The Initial Treatment Scan is typically the scan generated by the system without consideration of exposure limits to the iris, and therefore typically is an optimized scan or default scan pattern generated by the system based solely on a user parameter set and without regard to iris safety consideration. The location of the initial treatment scans may be projected onto at least one of the video and confocal images in order to define the set of expected scan locations of the incisions. The treatment scans according to the invention generally take the form of a raster scan of the ocular tissue to be incised.

A step 408 comprises calculating an initial exposure on the iris based on the initial treatment scan. The parameter sets defining the Initial treatment scan comprise a set of parameters that fully define the geometry (size and shape) of planned incision as well as the pulse energy, the horizontal spot spacing and the vertical spot spacing for carrying out the incision. As such, it is possible to calculate the spot density (for instance, spots/cm$^2$) as well as the power supplied by the pulses. Since the geometry of the eye in the area of the planned incision is known from the imaging scans, the size of the scanned pattern on the iris can be computed. As such, one can calculate an exposure of the iris tissue associated with the initial treatment scan. The exposure may be calculated by Pulse energy/cm2 as a function of the time taken to deliver the energy within a computed integrating aperture on the iris surface, and the worst case exposure within all such possible apertures on the iris surface is evaluated against the limit.

A step 410 comprises determining whether the calculated exposure is less than a predetermined iris exposure limit. A Step 414 comprises delivering the treatment beam to carry out the treatment scan and form the corneal incision. The delivery may be performed automatically or may require additional actions by a user. In some embodiments, if the exposure on the iris based on the initial treatment scan is lower than the predetermined limit, the system automatically delivers the treatment in some embodiments. In other embodiments, the methods and systems of the present invention require some additional act by a user (such as a physician) in order to initiate delivery of the treatment beam. For instance, the system may preferably be configured to provide a message or warning through, for instance, a graphical user interface, to a user that a revised treatment scan has been determined and may be delivered to the patient. The system may require that a user manually command delivery of the treatment scan once an acceptable scan has been determined. The system may require that the user press a button, peddle, lever or other device to initiate scan. In some embodiments, it may be preferable that a user be required to continually depress a button, lever, peddle or other device throughout a procedure to initiate and maintain delivery of the treatment scan from initiation to completion.

In some embodiments, a user may be required to enter a command via a graphical user interface in order to initiate a treatment scan.

A step 412 comprises generating a simulated revised treatment scan comprising one or more treatment scan modifying elements. That is, if the exposure on the iris caused by the initial treatment scan is greater than the predetermined exposure limit, the initial treatment scan is revised by adding one or more treatment scan modifying elements. The treatment scan modifying elements generally extend the period required to scan the ocular tissue or, in some instance, extend a period required to scan a specified aperture contained within the ocular tissue. In a preferred embodiment the inclusion of the treatment scan modifying elements to create a revised treatment scan does not modify the energy of the pulses, the spot spacing, and/or the spot density. That is, in many embodiments, the energy of the pulses actually delivered to the ocular tissue in the revised treatment scan is 90% or more, or 95% or more or 99% or more of the energy of the pulses in the initial treatment scan. In many embodiments, the spot density of the pulses actually delivered in the revised treatment scan is 90% or more, or 95% or more or 99% or more of the spot density of the pulses in the initial treatment scan. In many embodiments, the vertical spot spacing of the pulses actually delivered in the revised treatment scan is 90% or more, or 95% or more or 99% or more of the vertical spot spacing of the pulses in the initial treatment scan. In many embodiments, the horizontal spot spacing of the pulses actually delivered in the revised treatment scan is 90% or more, or 95% or more or 99% or more of the horizontal spot spacing of the pulses in the initial treatment scan. Further, the treatment scan modifying elements preferably do not change the size or geometry of the incision or its placement within the ocular tissue.

It should be noted that it may not be known precisely how many treatment scan modifying elements may be necessary to achieve a revised treatment scan with an exposure below the predetermined exposure limit. As such, one or more modified treatment elements may be added iteratively until the condition of Step 410 is satisfied. Thus, one or more initial treatment scan modifying elements may be included in a revised treatment scan (Step 410), the exposure of the revised treatment may be calculated (Step 410) and compared to the predetermined exposure limit (410). If the revised treatment scan does not result in an exposure below the exposure limit, additional treatment scan modifying elements may be include in the revised treatment scan until the condition of Step 408 is satisfied. At step 414, when exposure of a revised treatment scan is less than the predetermined limit, the system enables the physician to deliver the treatment beam to the ocular tissue to carry out the revised treatment scan, including any treatment scan modifying elements.

Figure 7B:
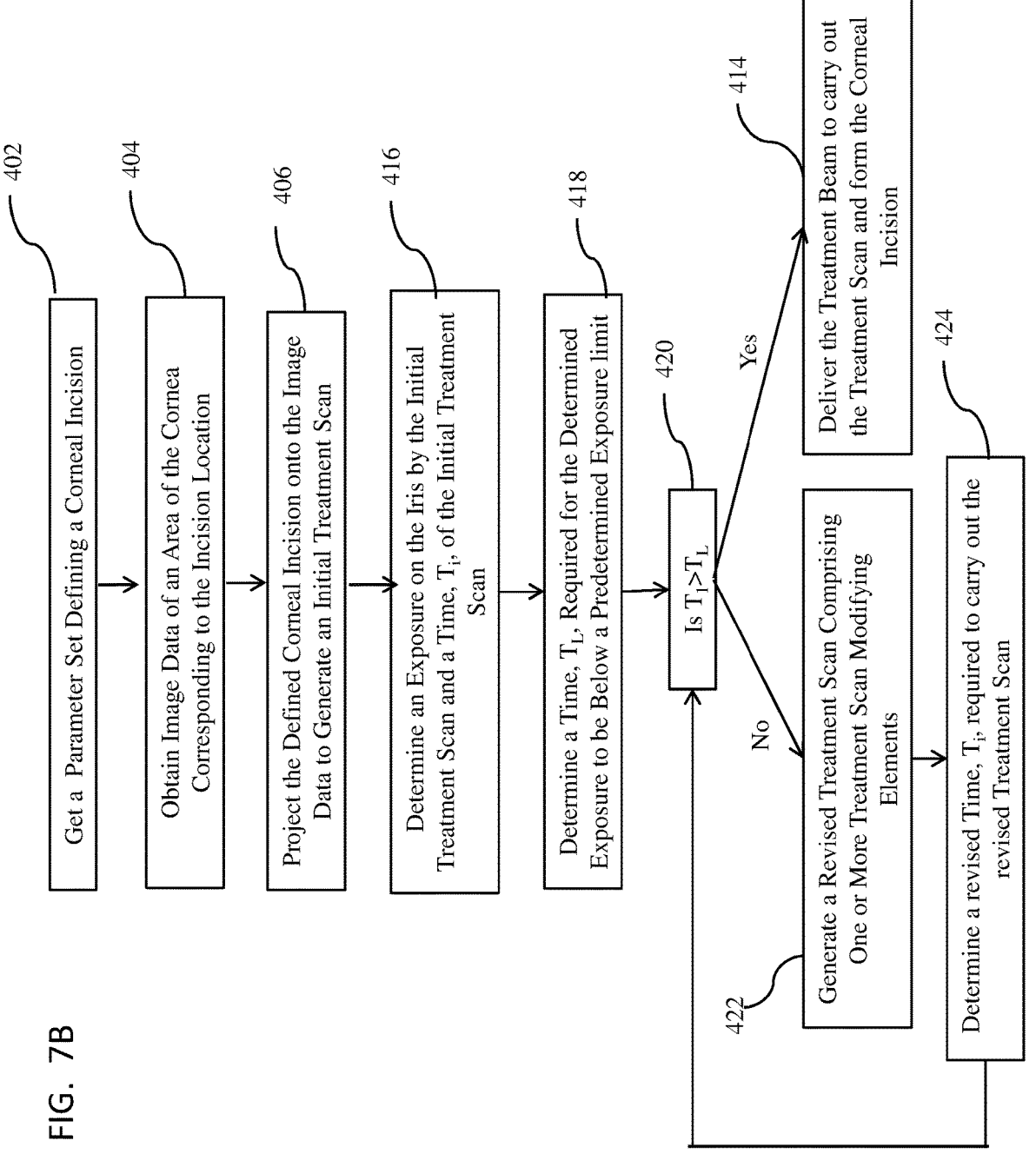
FIG. 7B is a diagram illustrating certain steps and acts in connection with an embodiment of a laser surgical method for performing a corneal incision while maintaining iris exposure below a predetermined exposure limit according to one embodiment.

A second embodiment in which the exposure associated with a planned treatment scan is maintained below a predetermined exposure level by extending time of the treatment scan by adding one or more treatment scan modifying elements so as to cause the iris exposure to be smaller than the predetermined exposure limit is shown in FIG. 7B.

A system for cataract surgery on an eye of a patient according to this embodiment comprises: a laser assembly for generating a pulsed laser treatment beam; an imaging system configured for imaging an ocular tissue of the patient, the ocular tissue comprising corneal tissue; an optical scanning system configured for positioning the focal zone of the treatment beam to targeted locations of the ocular tissue, targeting locations including a location in the corneal tissue; and a computer control system operatively coupled to the laser assembly, the imaging system, and the optical scanning system. The controller is programmed to: a) generate an initial treatment scan and an initial iris exposure and an initial scan time corresponding to the initial treatment scan; b) determine a minimum scan time required for the initial iris exposure to be below a predetermined exposure limit; c) determine whether the initial scan time is less than the minimum scan time; d) generate a revised treatment scan comprising one or more treatment scan modifying elements when the initial scan time is less than the minimum scan time, wherein the one or more treatment scan modifying elements cause a revised scan time to be longer than the permissible scan time; and e) operate the optical scanning system and laser assembly to direct a treatment beam in a pattern corresponding to the revised treatment scan so as to create a corneal incision.

In this embodiment, a laser surgical method for performing a corneal incision while maintaining an iris exposure below a predetermined exposure limit, the method comprising: determining an initial iris exposure and an initial scan time based on an initial treatment scan, the treatment scan corresponding to a predetermined corneal incision, determining a minimum scan time required for the initial iris exposure to be below a predetermined exposure limit; determining whether the initial scan time is less than the minimum scan time; generating a revised treatment comprising one or more treatment scan modifying elements, wherein the one or more treatment scan modifying elements causes a revised scan time to be longer than the minimum scan time, and scanning the focal zone of a pulsed laser beam according to the revised treatment scan, thereby performing the corneal incision.

Steps to be carried out in method to be performed by a system according to this embodiment are shown in FIG. 7B. These include a steps 402, 404 and 406, which are the same as are describe above with respect to FIG. 7A.

In the embodiment of FIG. 17B, Step 416 requires determining an exposure on the iris by the initial treatment scan and a time, $T_i$, over which the initial treatment scan will be carried out on the ocular tissue. The parameter sets used to derive the initial treatment scan comprise a set of parameters that fully define the geometry (size and shape) of planned incision as well as the pulse energy, the horizontal spot spacing and the vertical spot spacing for carrying out the incision. As such, it is possible to calculate the time which the system will require to carry out the initial treatment scan. This can be done with references to the known scan speed of the scanning system as well as the total distance traveled in the scan A step 418 comprises determining a minimum time, $T_L$, required for the determined exposure to be below a predetermined exposure limit. Specifically, since the energy to be delivered to the ocular tissue by the initial treatment scan is known, as is spot density and the size and geometry of the incision, it is possible to calculate the minimum time, $T_L$, over which the power can be safely delivered to the ocular tissue.

Let

Ex=the needed exposure to make the incision in: energy/unit area. (J/cm^2)

EL=the exposure limit in: energy/unit area=11*T^0.69 (J/cm^2)

Ae=the area of the full treatment scan exposure

Aa=the integrating aperture area

Te=total exposure time

Ti=the initial time for the treatment scan

Tai=the initial time for treatment within the integrating aperture=Ti*Aa/Ae

TL=the limit time for the incision

TaL=the limit time for exposure within the integrating aperture

Since we want to find the time that gives an exposure limit equal to the needed exposure:

EL=Ex

Then TaL=(Ex/11)^(−0.69)

TL=TaL*Ae/Aa

A step 420 comprises determining whether the time $T_i$ of the initial scan is greater than the minimum scan time, $T_L$. A Step 414 comprises delivering the treatment beam to carry out the treatment scan and form the corneal incision. Thus, if the time $T_i$ of the initial scan is greater than minimum time $T_L$, the initial treatment scan is delivered to the ocular tissue, thereby forming the corneal incision without any modification to the initial treatment scan.

The delivery of the treatment beam may be performed automatically or may require additional actions by a user. In some embodiments, the system automatically delivers the treatment in some embodiments. In other embodiments, the methods and systems of the present invention require some additional act by a user (such as a physician) in order to initiate delivery of the treatment beam. For instance, the system may preferably be configured to provide a message or warning through, for instance, a graphical user interface, to a user that a revised treatment scan has been determined and may be delivered to the patient. The system may require that a user manually command delivery of the treatment scan once an acceptable scan has been determined. The system may require that the user press a button, peddle, lever or other device to initiate scan. In some embodiments, it may be preferable that a user be required to continually depress a button, lever, peddle or other device throughout a procedure to initiate and maintain delivery of the treatment scan from initiation to completion. In some embodiments, a user may be required to enter a command via a graphical user interface in order to initiate a treatment scan.

A step 422 comprises generating a revised treatment scan comprising one or more treatment scan modifying elements. That is, if the time $T_i$ of the initial scan is less than minimum time $T_L$, the initial treatment scan is revised by adding on or more treatment scan modifying elements. The treatment scan modifying elements generally extend the period required to scan the ocular tissue or, in some instance, extend a period required to scan a specified aperture contained within the ocular tissue. In a preferred embodiment the inclusion of the treatment scan modifying elements to create a revised treatment scan does not modify the power of the energy pulses, the spot spacing, the spot density, or the number of pulses per unit area. That is, in many embodiments, the energy of the pulses actually delivered to the ocular tissue in the revised treatment scan is 90% or more, or 95% or more or 99% or more of the energy of the pulses in the initial treatment scan. In many embodiments, the spot density of the pulses actually delivered in the revised treatment scan is 90% or more, or 95% or more or 99% or more of the spot density of the pulses in the initial treatment scan. In many embodiments, the vertical spot spacing of the pulses actually delivered in the revised treatment scan is 90% or more, or 95% or more or 99% or more of the vertical spot spacing of the pulses in the initial treatment scan. In many embodiments, the horizontal spot spacing of the pulses actually delivered in the revised treatment scan is 90% or more, or 95% or more or 99% or more of the horizontal spot spacing of the pulses in the initial treatment scan. Further, the treatment scan modifying elements preferably do not change the size or geometry of the incision or its placement within the ocular tissue.

It should be noted that in some embodiments, it may not be known precisely how many treatment scan modifying elements may be necessary to achieve a revised treatment scan with a scam time $T_i$ greater than the minimum scan time, $T_L$. As such, one or more modified treatment elements may be added iteratively until the condition of Step 420 is satisfied. Thus, one or more initial treatment scan modifying elements may be included in a revised treatment scan (Step 422), the time of the revised treatment may be calculated (Step 424) and compared to the minimum scan time $T_L$ (410). If the revised treatment scan does not result in an exposure below the exposure limit, additional treatment scan modifying elements may be include in the revised treatment scan until the condition of Step 408 is satisfied. At step 414, when exposure of a revised treatment scan is less than the predetermined limit, the treatment beam is delivered to the ocular tissue to carry out the revised treatment scan, including any treatment scan modifying elements.

In other embodiments, a treatment scan modifying element may have associated with it a known scan time so that the addition of a treatment scan modifying element will have a predetermined effect on the total scan time. In this way, treatment scan modifying elements can be added to an initial treatment scan to achieve a known total scan time, and one or more treatment scan modifying elements can be advantageously selected from amongst the various treatment scan modifying elements based on their respective known contributions to the scan time.

In the two methods shown in FIGS. 7A and 7B, the evaluation in step 410 and step 420 may be expressed more generally as: Determining whether a calculated indication of exposure level of a treatment scan (the initial treatment scan or a revised treatment scan) satisfies a predetermined safe exposure condition. In the method of FIG. 7A, the calculated indication of exposure level of the treatment scan is the exposure, calculated in step 408, while the safe exposure condition is expressed as "the calculated exposure is less than the predetermined Iris Exposure Limit" (step 410). In the method of FIG. 7B, the calculated indication of exposure level of the treatment scan is the time $T_i$ required to carry out the treatment scan, calculated in step 416 for the initial treatment scan and in step 424 for the revised treatment scan, while the safe exposure condition is expressed as "the time $T_i$ required to carry out the treatment scan is longer than a minimum time $T_L$ required for iris exposure to be below a predetermined exposure limit" (step 420). In both methods, after generating a revised treatment plan (step 412 in FIG. 7A and step 422 in FIG. 7B), the method re-calculates the indication of exposure level of the revised treatment scan (step 408 in FIG. 7A and step 424 in FIG. 7B), and re-evaluates the safe exposure condition for the revised treatment plan (repeat step 410 in FIG. 7A and step 420 in FIG. 7B). In both methods, this process is repeated until the safe exposure condition is satisfied (Yes in step 410 or 420), before proceeding to step 414.

Figure 8:
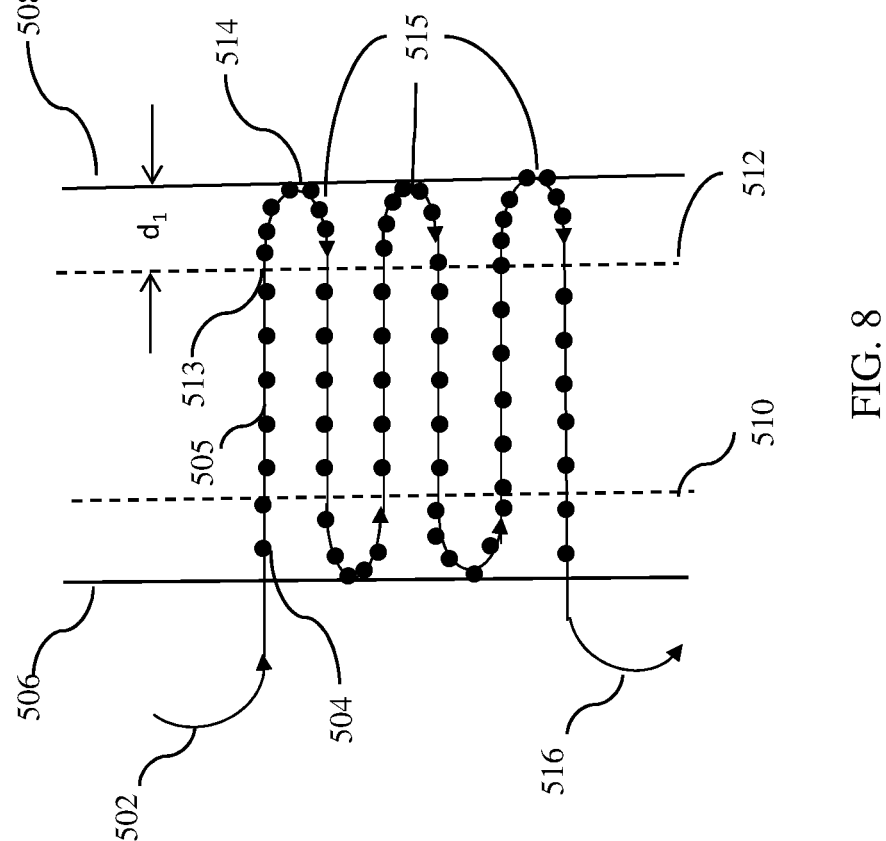
FIG. 8 is a graphical illustration of a treatment scan that does not include treatment scan modifying elements according to the present invention.
Figure 9:
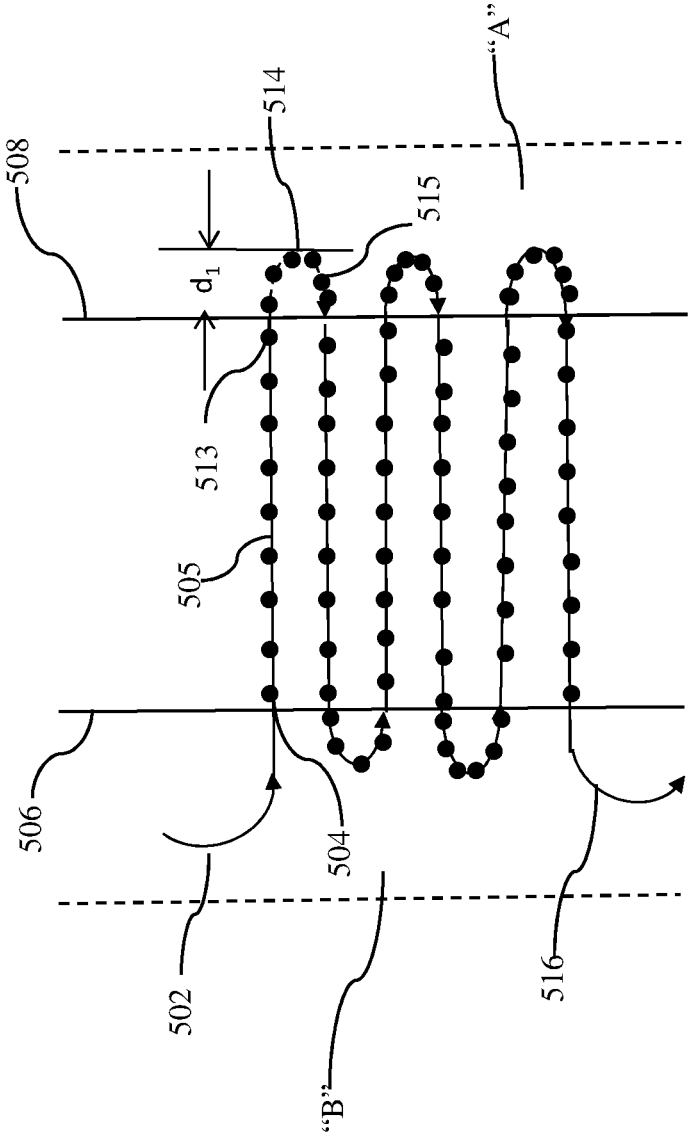
FIG. 9 is a graphical illustration of a treatment scan having an extension of scan paths in which the turnarounds occur beyond an incision boundary.
Figure 10A:
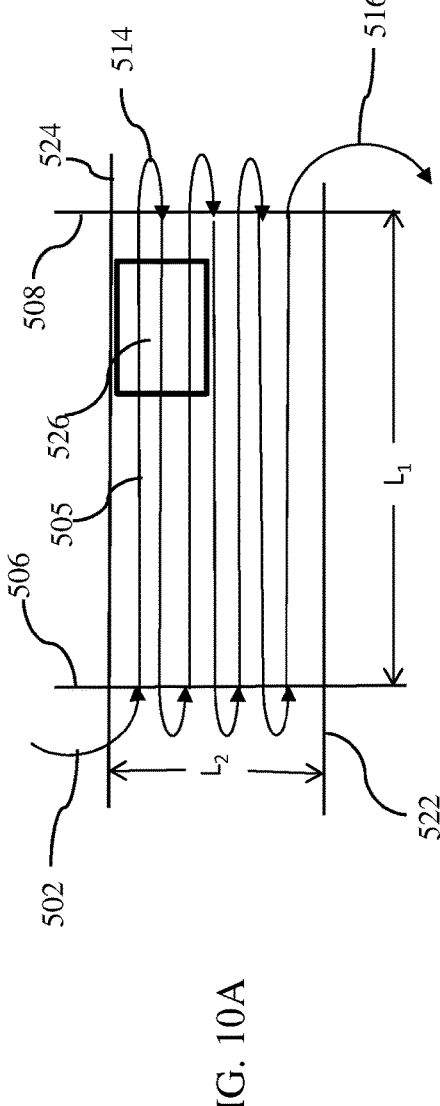
FIGS. 10A and 10B are graphical illustrations illustrating an advantage of reorienting an axis along a longer axis.
Figure 10B:
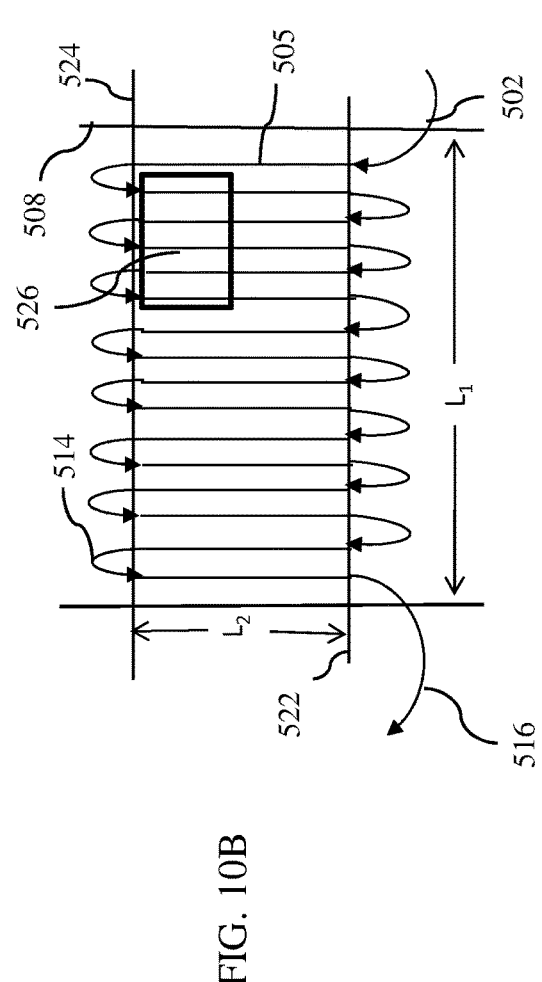
Figures 11A, 11B:
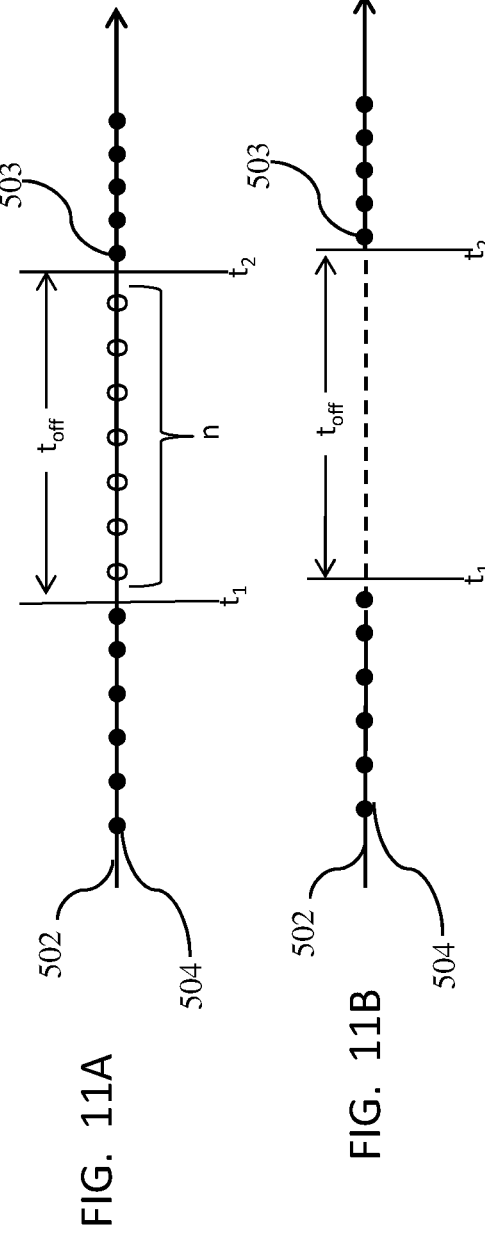
FIGS. 11A and 11B are graphical illustrations of pulse gating.
Figures 12A, 12B:
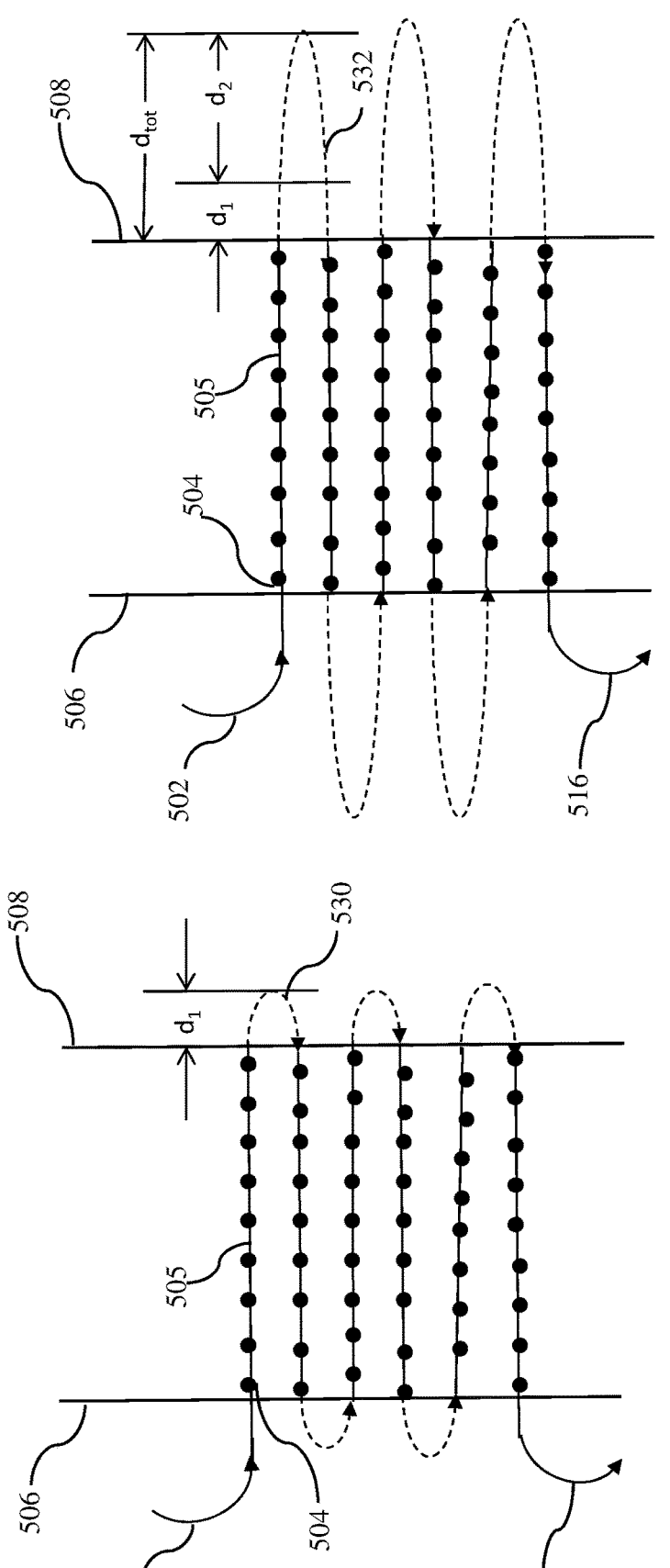
FIGS. 12A and 12B are graphical illustration of different embodiments of pulse gating turnarounds.
Figure 13:
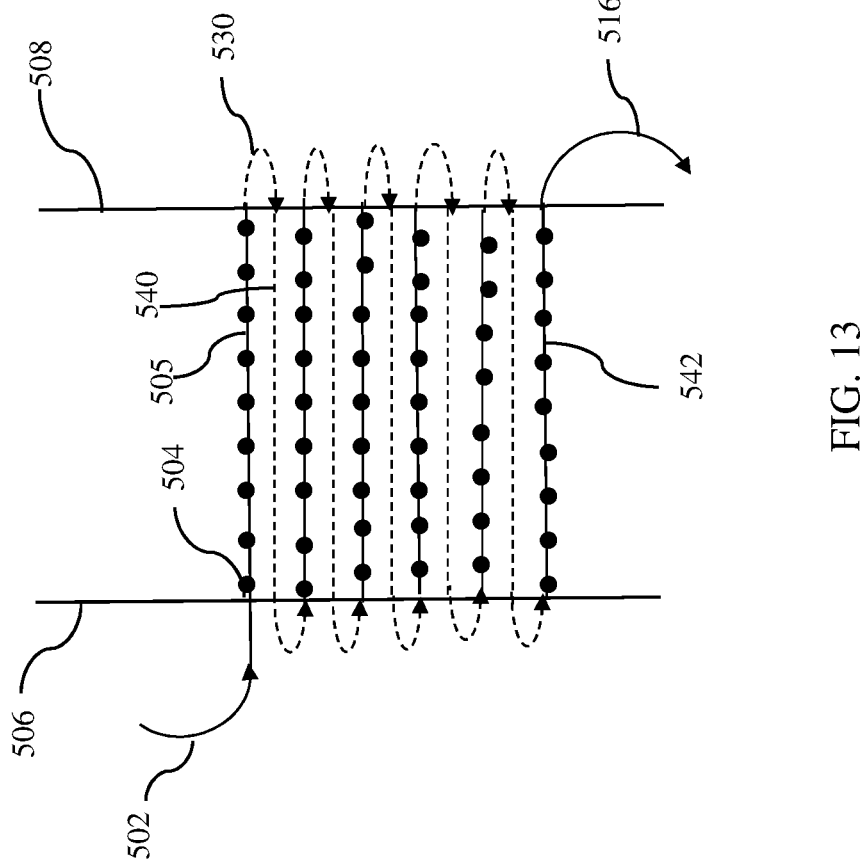
FIG. 13 is a graphical illustration of pulse gating rows.

In many embodiments, including the above embodiments, the one or more treatment scan modifying elements is selected from the group consisting of: an extension of scan paths so that at least a portion of the respective turnarounds occur beyond an incision boundary; a reoriented scan axis; an extension of the scan paths so that at least a portion of the respective turnarounds are gated and also extend beyond the incision boundary; and, an insertion of a gated rows with active rows in a fixed proportion. FIGS. 8-13 show different aspects and embodiments of treatment scan modifying elements according to the present invention. FIG. 8 is a graphical illustration of a treatment scan that does not include treatment scan modifying elements according to the present invention. FIG. 9 is a graphical illustration of a treatment scan having an extension of scan paths in which the turnarounds occur beyond an incision boundary. FIGS. 10A and 10B are graphical illustrations illustrating an advantage of reorienting an axis along a longer axis. FIGS. 11A and 11B are graphical illustrations of pulse gating. FIGS. 12A and 12B are graphical illustration of different embodiments of pulse gated turnarounds. FIG. 13 is a graphical illustration of pulse gated rows.

FIG. 8 is a graphical illustration of a treatment scan that does not include treatment scan modifying elements according to the present invention. As such, it illustrates certain features of an initial treatment scan generated by the system without consideration of exposure limits to the iris. It may be typically an optimized or default scan pattern generated by the system based solely on a user parameter set and without regard to iris safety consideration. The treatment scan path 502 is a continuous set of x, y, z points traveled by the focal zone of the laser beam in the directions shown by the arrows of the scan path 502. In some embodiments, the scan path comprises a plurality of rows 505 with turnarounds 515 at or near boundaries 506, 508. Although rows 515 are shown as being linear in FIG. 8, rows may be curves. The plurality of rows is preferably parallel. Here, the term substantially parallel means an angle formed by the intersection of the two rows is preferably less than 20°, or less than 10°, or less than 5°, or less than 1°.

Turnarounds 515 occur as the light beam reaches the end of row 505 and initiates a process for reversing the direction of the laser beam along the scan path 504 to scan an adjacent row. Specifically, the laser beam begins deceleration at location 513 (a turnaround start location 513) along and reaches a zero velocity location 514 at which its velocity is zero, before changing direction and accelerating into the next row. A turnaround distance, $d_1$, is defined as the distance from the turnaround start location 513 to zero velocity location 514 in a direction parallel to the rows 505.

Laser pulses 504 are periodically emitted by the pulsed laser system as the focal zone of the laser is scanned along scan path 502. The size of the pulses 504 shown in the drawings are not to scale and are for illustrative purposes only. The spacing between adjacent spots is generally included in the parameter set defining the incision. However, in raster patterns such as those of FIG. 8, a higher density of pulses (and closer spot spacing than intended) can occur at or near the boundaries 506, 508 due to the deceleration of the laser light beam in the turnaround, which results in higher exposures at the incision boundaries 506, 508 where turnarounds 515 occur. This can result in spot spacing between pulses less than were specified by a user in the parameter set defining the incision. Further, the adjacent turnarounds can cause the occurrence of regions of very high density laser pulses in a direction perpendicular to the rows (a first region between line 512 defined by connecting adjacent turnaround start points and the boundary 508 and second region on the opposite end of the rows between line 510 and boundary 506). These regions of very high exposures, or "hot zones," can cause excessive exposures or excessive heating and can significantly degrade incision quality.

FIG. 9 is a graphical illustration of a treatment scan modifying element a scan path 502 is extended such that turnarounds 515 occur beyond an incision boundary. It is noted that in the embodiment of FIG. 9, Regions "A" and "B" occurring on either side of the incision boundaries 508, 506, respectively, should be non-incisionable material. The portion of Regions "A" and "B" into which the turnarounds 515 extend should not be ocular tissue that might be incised by the laser beam. More preferably, the focal zone of the laser does not significantly interact with material of Regions "A" and "B" as the focal zone is being scanned through regions. This is because the focal zone of laser pulses is swept through Regions "A" and "B." Excessive exposure of inappropriate incisions could occur if the material were incisionable or otherwise significantly interacted with the laser pulses 504. Example of suitable material for Regions "A" and "B" include air and water. Examples of incisions in which the embodiment of FIG. 9 may be implemented are sideport incisions.

In FIG. 9, rows 505 are sized so that at least a portion of the turnarounds 515 of the scan path 502 extend beyond the incisions boundaries 506, 508. However, the entirety of the turnaround need not extend beyond incision boundaries 506, 508. In many embodiments, rows 505 are sized such that the zero velocity location 514 extends beyond incision boundary 508 by an amount greater than 50% of the turnaround distance $(0.5d_1)$ and less than the turnaround distance $(d_1)$, or beyond the boundary in an amount greater than 70% of the turnaround distance $(0.7d_1)$ and less than the turn the turnaround distance $(d_1)$, or beyond the boundary in amount greater than 90% $(0.9d_1)$ of the turnaround distance and less than the turnaround distance $(d_1)$. In many embodiments, rows 505 are sized such that the zero velocity location 514 extends beyond incision boundary 508 by an amount equal to or greater than the turnaround distance $(d_1)$. In many embodiments, rows 505 are sized such that the zero velocity location 514 extends beyond incision boundary 508 by an amount equal to the turnaround distance $(d_1)$.

By scanning the laser beyond incisions boundaries 506, 508, the total length of time to complete the scan increases, thus providing more time for the energy supplied within boundaries 506, 608 to dissipate. Moreover, spot spacing is more uniform within incision boundaries 506, 508 and hot zones are eliminated.

FIGS. 10A and 10B are graphical illustrations of a treatment scan modifying element having a reoriented scan axis. FIGS. 10A and 10B both show a scan pattern for scanning an incision have two sets of opposed boundaries. A first set of opposed boundaries 506, 508 are separated by a first and longer distance $L_1$. A second set of opposed boundaries 522, 524 is separated by a second and shorter distance $L_2$. In FIG. 10A, rows 505 of scan pattern 502 are scanned along the long dimension $L_1$, while in FIG. 10B, rows 505 of scan pattern 502 are scanned long the short dimension $L_2$. An exposure aperture 526 is disposed within the boundaries of the incision. Since the rows in FIG. 10A are longer and in the rows in FIG. 10A, there is a longer period between the time the laser beam exits the aperture and returns to the aperture in the scan pattern of FIG. 10A than the analogous time period of FIG. 10A. This longer time period provides more time for the aperture area 526 to dissipate heat between scans of the laser beam through the aperture. As such, in many embodiments, particularly in long, narrow incision, rows 505 of the scan path are preferably oriented along the longer axis $L_1$.

In many embodiments, orienting the scan paths along the longer axis $L_1$, as shown, for instance in the embodiment of FIG. 10A, may be preferentially adopted, where, for example, $L_1 \geq 1.5L_2$, $L_1 \geq 2L_2$, $L_1 \geq 3L_2$, $L_1 \geq 5L_2$, or even $L_1 \geq 5L_2$. An example of an incision for which the treatment scan modifying element may be particularly well suited is the sideport incision.

FIGS. 11A and 11B graphically illustrate several aspects of a pulse gating technique according to many embodiments of the present invention. In the pulse gating technique, the laser source is controlled by the controller so as to be first turned off and then turned back on one or more times during a treatment scan of the ocular tissue to be incised. When the laser source is a Q-switched ND:YAG laser, the Q-Switch is turned off and on to effectuate the pulse gating during the treatment scan. This Off/On sequence during an active scan controls the placement and duration of the pulse gate.

As illustrated in FIG. 11A, as the laser pulses 504 are scanned along treatment scan path 502, the laser is turned OFF at a time $t_1$ and remains OFF until the laser is turned ON again at a time $t_2$, thus establishing a total time the laser is off, $t_{off}$. Although the laser is OFF during the $t_{off}$ period, the scanning system remains active during entire entirety of this time period and operating to carry out the scan path of the treatment scan. That is, the scan path traced by the scanning system continues during this $t_{off}$ period. As such, when the laser is turned ON at time $t_2$, the laser pulses are positioned at the same position they otherwise would have been had the laser been ON throughout $t_{off}$.

This OFF/ON sequence is referred to herein as a "Pulse Gate" or "Pulse Gating." As used herein, a treatment scan is "active" when the laser is ON and laser pulses are being actually delivered to the ocular tissue laser source and scanning system. And a treatment scan is "gated" or "blanked" when the laser is OFF during the treatment scan. Thus, for instance, in FIG. 11A, the treatment scan is active before $t_1$ and after $t_2$. The treatment scan is gated (also termed blanked) during the gated time period, $t_{off}$. In FIG. 11A, the unfilled circles represent the locations of laser pulses that would have been delivered to the ocular tissue had the laser been turned ON during the $t_{off}$ period. These can be referred to as "gated pulses" or "blanked pulses."

The length of the gated time period can be defined in terms of either seconds or milliseconds or, because the scanning system is active during the gated period, as a number of gated pulses, n. In some embodiments, the gated time period $t_{off}$ is less than 200 ms, or less than 100 ms, or less than 50 ms or less than 20 ms. It has also been determined that the first pulse after the laser is turned on at a time $t_2$ may have a significantly different energy than other laser pulses. As such, if the number of pulse gates are sequenced closely together, the average power delivered will be larger active pulses may be larger than the set value. Thus, in some embodiments, there is a space of 3 active pulses or more, or 5 or more active pulses, or 10 or more active pulses between pulse gates.

FIG. 11B is identical to FIG. 11A except that it represents gated regions with dashed lines. This representation is used in FIGS. 12A, 12B, and 13.

FIGS. 12A and 12B graphically illustrate a gated turnaround treatment scan element. In the examples of 12A and 12B, the treatment scan modifying element typically comprises an extension of the scan paths so that at least a portion of the respective turnarounds are gated and extend beyond the incision boundary FIG. 12A is similar to that described above in connection with FIG. 9 except that the turnarounds in FIG. 9 are active and the turnarounds in FIG. 12A are gated. Since the turnarounds in the embodiment of FIG. 12A are gated, the material beyond incision boundaries 506, 508 in Regions "A" and "B" may be any material, including the same tissue as is between boundaries 506, 508. As such, a gated turnaround treatment scan modifying element may be used with any number of incisions, especially corneal incisions.

In the embodiment, rows 505 are sized so that at least a portion of the turnarounds 530 of the scan path 502 are gated and extend beyond the incisions boundaries 506, 508. However, the entirety of the turnaround needs not be gated and extend beyond incision boundaries 506, 508. In many embodiments, rows 505 are sized such that the zero velocity location 514 extends beyond incision boundary 508 by an amount greater than 50% of the turnaround distance ($0.5d_1$) and less than the turnaround distance ($d_1$) and this portion is gated. Or rows 505 are sized such that the zero velocity location 514 extends beyond incision boundary 508 beyond the boundary in an amount greater than 70% of the turnaround distance ($0.7d_1$) and less than the turn the turnaround distance ($d_1$) and this portion is gated. Or rows 505 are sized such that the zero velocity location 514 extends beyond incision boundary 508 beyond the boundary in amount greater than 90% ($0.9d_1$) of the turnaround distance and less than the turnaround distance ($d_1$) and this portion is gated. In many embodiments, rows 505 are sized such that the zero velocity location 514 extends beyond incision boundary 508 by an amount equal to the turnaround distance ($d_1$).

FIG. 12B shows an embodiment in which rows 505 are sized such that the zero velocity location 514 extends beyond incision boundary 508 by an amount greater than the turnaround distance ($d_1$), and the entire turnaround is gated by an additional extension amount, $d_2$. Here the additional amount extension amount $d_2$ is added to the turnaround distance in order to lengthen the total length of time to complete the treatment scan. In some embodiments, the total turnaround distance, $d_{tot} \geq 1.1d_1$, or $d_{tot} \geq 1.5d_1$, or $d_{tot} \geq 2d_1$, or $d_{tot} \geq 5d_1$.

By scanning the laser beyond incisions boundaries 506, 508, the total length of time to complete the scan increases, thus providing more time for the energy supplied within boundaries 506, 608 to dissipate. The gated turnarounds prevent any damage to structures beyond incision boundaries 506, 508. And spot spacing is more uniform within incision boundaries 506, 508 and hot zones are eliminated.

FIG. 13 is a graphical illustration of a treatment scan modifying element comprising pulse gated rows. The treatment scan modifying element of this embodiment generally comprises an insertion of gated rows with respective active rows in a fixed proportion. In the preferred embodiment illustrate in FIG. 13, optional gated turnarounds 130 are shown.

In the embodiment of FIG. 13, the treatment scan is generated according the parameter set defining the incision and gated rows are added to the active rows of the treatment scan in a fixed proportion. In the embodiment of FIG. 13 gated rows are added to active rows in a substantially 1:1 ratio. In many embodiments the ration of gated rows to active rows is 1:1, or 2:1 or 3:1. In many embodiments the ratio of gated rows to active rows is between substantially 1:1 and substantially 10:1. Here, the term "substantially" reflects that the total number of rows may be an odd number. Specifically, as shown in FIG. 13, there may be no need to provide a gated row after the last active scan in a treatment scan and the laser beam is exits 516 the scan location.

In another embodiment, laser surgical methods and systems safely deliver a predetermined power by modifying one or more incision parameters, thereby limiting the power delivered during the planned incision.

In a first embodiment, a user of a laser surgical system is permitted to revise the incision parameter so that the iris exposure is below the predetermined iris exposure limit. According to this embodiment, a system for cataract surgery on an eye of a patient comprises: a laser assembly for generating a pulsed laser treatment beam; an imaging system configured for imaging an ocular tissue of the patient, the ocular tissue comprising corneal tissue; an optical scanning system configured for positioning the focal zone of the treatment beam to targeted locations of the ocular tissue, the targeting locations including a location in the corneal tissue; a user interface for receiving input from a user, a graphical user interface for providing information to the user; and a computer control system operatively coupled to the laser assembly, the imaging system, the optical scanning system, the user interface and the graphical user interface. The computer control system is programmed to: a) generate an initial treatment scan based on a parameter set received via the user interface, and also generate an initial iris exposure corresponding to the initial treatment scan; b) determine whether the initial iris exposure is less than a predetermined exposure limit; c) generate a revised treatment scan based on a revised parameter set received from the user via the user interface, the revised parameter set having at least one different parameter value than the initial parameter set, d) generate a revised exposure corresponding to the revised treatment scan; and e) operate the optical scanning system and laser assembly to direct a treatment beam in a pattern corresponding to the revised treatment scan so as to create a corneal incision if the revised iris exposure is smaller than the predetermined exposure limit.

Figure 14A:
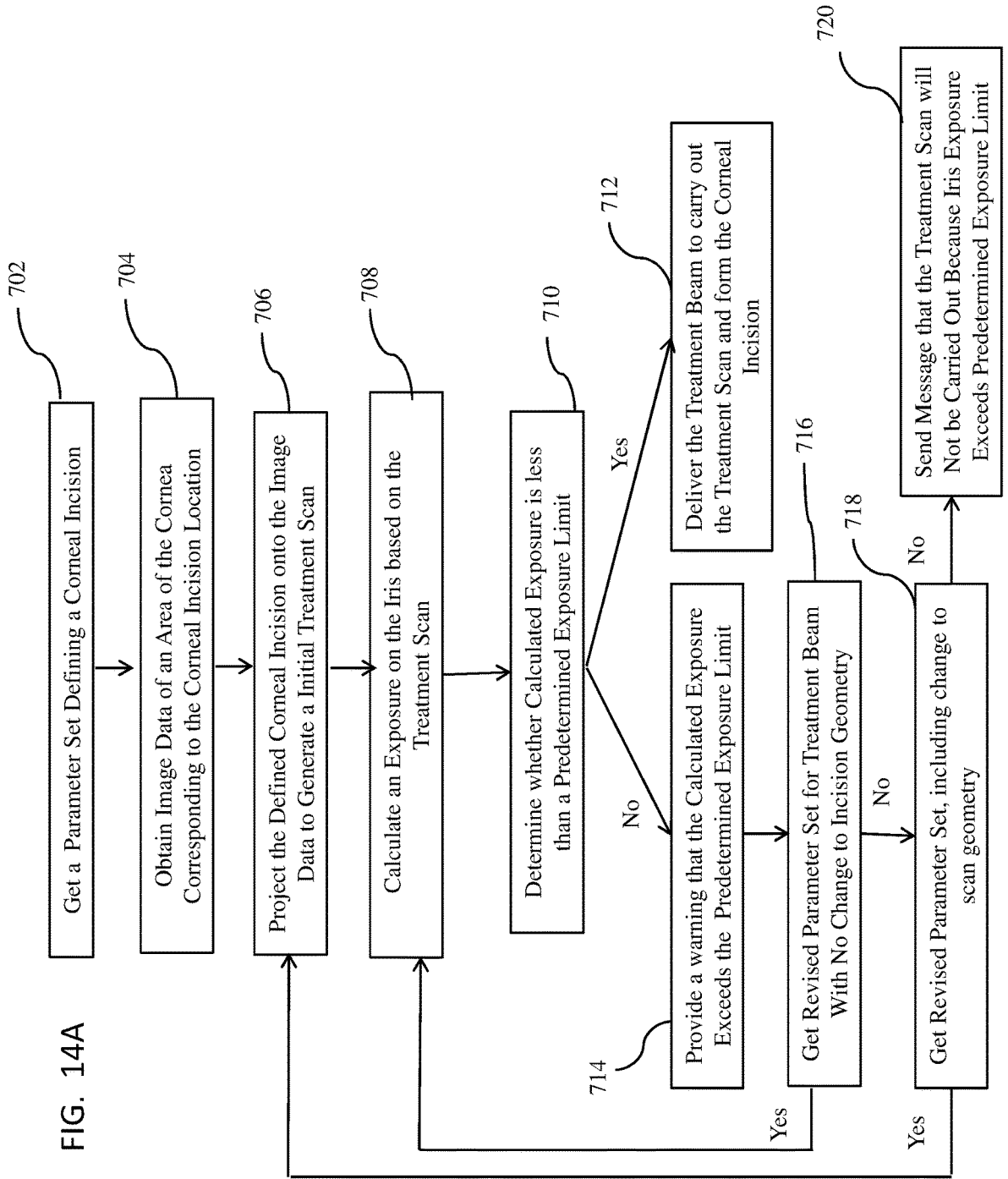
FIG. 14A is a diagram illustrating certain steps and acts in connection with an embodiment of a laser surgical method for performing a corneal incision while maintaining iris exposure below a predetermined exposure limit according to an embodiment.

Steps to be carried out in method to be performed by a system according to this embodiment are shown in FIG. 14A. These include Steps 702, 704, 706, 708 and 710, which are analogous to Steps 402, 404, 406, 408 and 410 describe above with respect to FIG. 7A.

Thus, for instance, a Step 702 comprises receiving a parameter set defining a corneal incision. A Step 704 comprises obtaining image data of an area of the cornea corresponding to the to the corneal incision location. A Step 706 comprises projecting the defined corneal incisions on the image data to generate an initial treatment scan. A Step 708 comprises calculating an exposure on the iris based on the initial treatment scan. A Step 710 comprises determining whether the calculated exposure is less than a predetermined exposure limit.

A Step 712 comprises delivering the treatment beam to carry out the treatment scan and form the corneal incision. Thus, if the exposure on the iris based on the initial treatment scan is lower than the predetermined limit, the initial treatment scan is delivered to the ocular tissue, thereby forming the corneal incision without any modification to the initial treatment scan. The delivery of the treatment beam may be performed automatically or may require additional actions by a user. In some embodiments, the system automatically delivers the treatment. In other embodiments, the methods and systems of the present invention require some additional act by a user (such as a physician) in order to initiate delivery of the treatment beam. For instance, the system may preferably be configured to provide a message or warning through, for instance, a graphical user interface, to a user that a revised treatment scan has been determined and may be delivered to the patient. The system may require that a user manually command delivery of the treatment scan once an acceptable scan has been determined. The system may require that the user press a button, peddle, lever or other device to initiate scan. In some embodiments, it may be preferable that a user be required to continually depress a button, lever, peddle or other device throughout a procedure to initiate and maintain delivery of the treatment scan from initiation to completion. In some embodiments, a user may be required to enter a command via a graphical user interface in order to initiate a treatment scan.

A Step 714 comprises providing a warning that the calculated exposure limit exceeds the predetermined exposure limit. Thus, if the exposure on the iris based on the initial treatment scan is higher than the predetermined limit, a warning is provided to a physician or other user of the system, thereby informing the user that the iris exposure limit is exceeded. The warning is preferably provided to the use via the graphical user interface under the control of the controller. The warning preferably provides a means, such as through the graphical user interface, for provide a revised parameter set having at least one different parameter value than the initial parameter set.

Step 720 comprising sending a message the user that the treatment scan will not be carried out if a revised parameter set is not received. Thus, if no revised parameter set is received in response to the warning, the treatment scan is not carried out. In this way, the methods and systems of the present embodiment ensure that the iris exposure limit is not exceeded by the treatment scan.

A Step 716 comprises receiving a revised parameter set for the treatment beam with no change to incision geometry. A Step 718 comprises receiving a revised parameter set that includes changes to incision geometer. As indicated above, a user may provide a revised parameter set for the incision to be formed in the ocular tissue. Some parameters in the revised parameter set may affect incision geometry and some may not affect incision geometry. In tables 3, 4, and 5, the parameters that do not affect incision geometry are the horizontal spot spacing, the vertical spot spacing and the pulse energy. All of the other parameters typically affect incision geometry.

If, in Step 716, are revised parameter not affected geometry is received, i.e., the parameter set contains changes only to one or more horizontal spot spacing, the vertical spot spacing and the pulse energy, the exposure on the iris is recalculated at Step 708 and it is subsequently determined whether the revised exposure exceeds the predetermined exposure limit at Step 710.

In Step 718, if the revised parameter set changes the geometry of an incision, the revised corneal incision is projected onto the image data to generate a revised treatment scan at Step 706, the exposure on the iris is recalculated at Step 708, and it is subsequently determined whether the revised exposure exceeds the predetermined exposure limit at Step 710.

It should be noted that revisions to the parameter set may be performed iteratively. As such, one or more parameters may be changed iteratively until the condition of Step 710 is satisfied. Thus, one or more parameters values may be revised (Steps 716, 718), the exposure of the revised treatment may be calculated (Step 706, 708) and compared to the predetermined exposure limit (710). If the revised treatment scan does not result in an exposure below the exposure limit, additional parameter values may be changed until the condition of Step 710 is satisfied. At step 712, when exposure of a revised treatment scan is less than the predetermined limit, the treatment beam is delivered to the ocular tissue to carry out the revised treatment scan, including any treatment scan modifying elements. The delivery of the treatment beam may be performed automatically or may require additional actions by a user. In some embodiments, the system automatically delivers the treatment. In other embodiments, the methods and systems of the present invention require some additional act by a user (such as a physician) in order to initiate delivery of the treatment beam. For instance, the system may preferably be configured to provide a message or warning through, for instance, a graphical user interface, to a user that a revised treatment scan has been determined and may be delivered to the patient. The system may require that a user manually command delivery of the treatment scan once an acceptable scan has been determined. The system may require that the user press a button, peddle, lever or other device to initiate scan. In some embodiments, it may be preferable that a user be required to continually depress a button, lever, peddle or other device throughout a procedure to initiate and maintain delivery of the treatment scan from initiation to completion. In some embodiments, a user may be required to enter a command via a graphical user interface in order to initiate a treatment scan.

In connection with the above method, a user may not be unsure which parameter can be changed in order to reduce the exposure to an exposure below the predetermined exposure limit. As such, in some embodiments, the system provides a series of optional scan patters, each resulting in an iris exposure below the predetermined iris exposure limit.

In many embodiments, a system for cataract surgery on an eye of a patient comprises: a laser assembly for generating a pulsed laser treatment beam; an imaging system configured for imaging an ocular tissue of the patient, the ocular tissue comprising corneal tissue; an optical scanning system configured for positioning the focal zone of the treatment beam to targeted locations of the ocular tissue, the targeting locations including a location in the corneal tissue; a user interface for receiving input from a user, a graphical user interface for providing information to the user; and a computer control system operatively coupled to the laser assembly, the imaging system, the optical scanning system, the user interface and the graphical user interface. The computer controls system is programmed to: a) generate an initial treatment scan based on a parameter set received via the user interface, and also generate an initial iris exposure corresponding to the initial treatment scan; b) determine whether the initial iris exposure is less than a predetermined exposure limit; c) generate one or more revised parameter sets, each of the one or more parameter sets having at least one different parameter value, and generate a revised treatment scan corresponding to each revised parameter set, wherein a revised iris exposure corresponding to each respective revised treatment scan is smaller than the predetermined exposure limit; d) cause the one or more revised parameter sets to be provided to a user via the graphical user interface, e) receive a selected one of the one or more revised parameter sets; and f) operate the optical scanning system and laser assembly to direct a treatment beam in a pattern corresponding to the revised treatment scan generated from the selected parameter set so as to create a corneal incision.

Steps to be carried out in method to be performed by a system according to this embodiment are shown in FIG. 14B. These include Steps 702, 704, 706, 708, 710, 712 and 714, which are the same as those of Steps 702, 704, 706, 708, 710, 712 and 714 described above with respect to FIG. 14A. In the embodiment of FIG. 14B, a Step 716 comprises providing one or more revised parameter sets, each resulting in a treatment scan with an iris exposure below the predetermined iris exposure limit. A Step 718 comprises determining whether a selection of a revised parameter set is received. If a revised parameter set is not received, Step 720 comprises sending a message to the user that the treatment scan will not be carried out. Thus, if no revised parameter set is received in response to the warning, the treatment scan is not carried out. In this way, the methods and systems of the present embodiment ensure that the iris exposure limit is not exceeded by the treatment scan. It is noted that in the embodiments of FIGS. 14A and 14B, the safe exposure condition evaluated in step 710 is similar to that in step 410 of FIG. 7A. In alternative embodiments, the method may evaluation a safe exposure condition similar to that in step 420 of FIG. 7B, i.e., whether the time Ti required to carry out the treatment scan is longer than a minimum time $T_L$ required for iris exposure to be below a predetermined exposure limit. Correspondingly, step 710 in FIGS. 14A and 14B will be replaced by a step similar to step 416 or step 424 of FIG. 7B to calculate the time $T_i$ required to carry out the initial or revised treatment scan. Although flowcharts for such alternative methods are not provided, those skilled in the art will be able to implement these alternative methods by referring to FIGS. 7A and 7B. Stated more generally, step 710 in FIGS. 14A and 14B is a step of determining whether a calculated indication of exposure level of a treatment scan (the initial treatment scan or a revised treatment scan) satisfies a predetermined safe exposure condition, where the calculated indication of exposure level of the treatment scan is either the exposure or the time $T_i$ required to carry out the treatment scan.

EXPERIMENTAL

Methods

Figure 18:
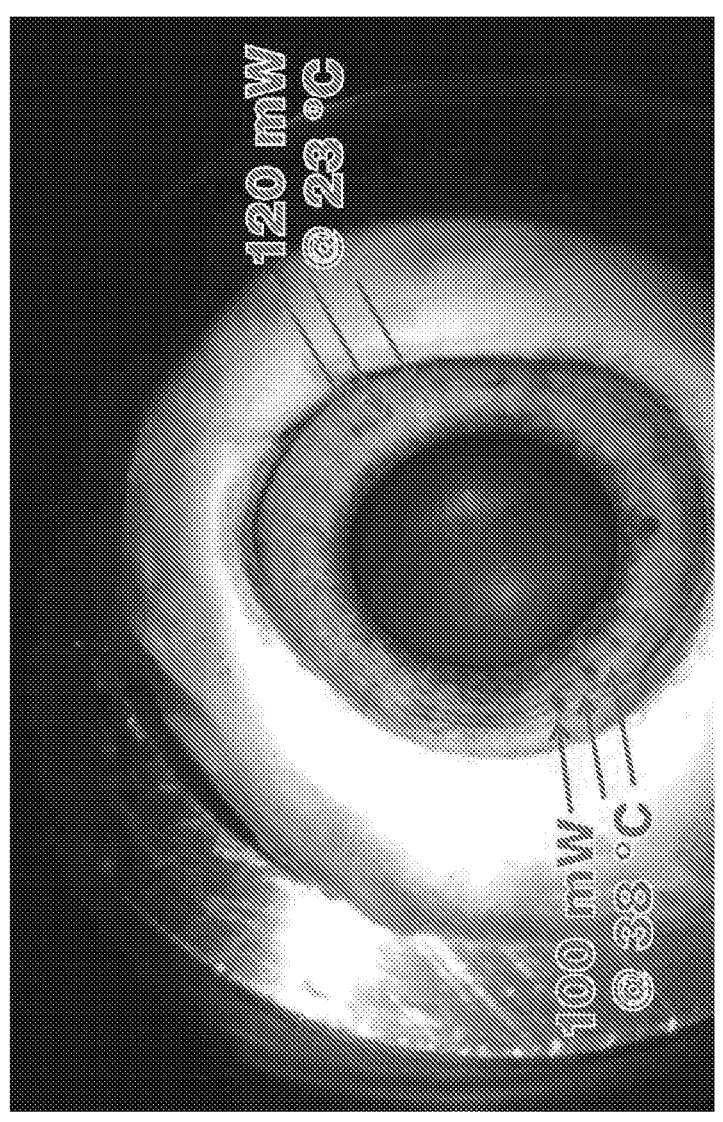
FIG. 18 is an enface image of an Ex vivo porcine eye showing an MVL of the iris at different temperatures and laser power.
Figure 19:
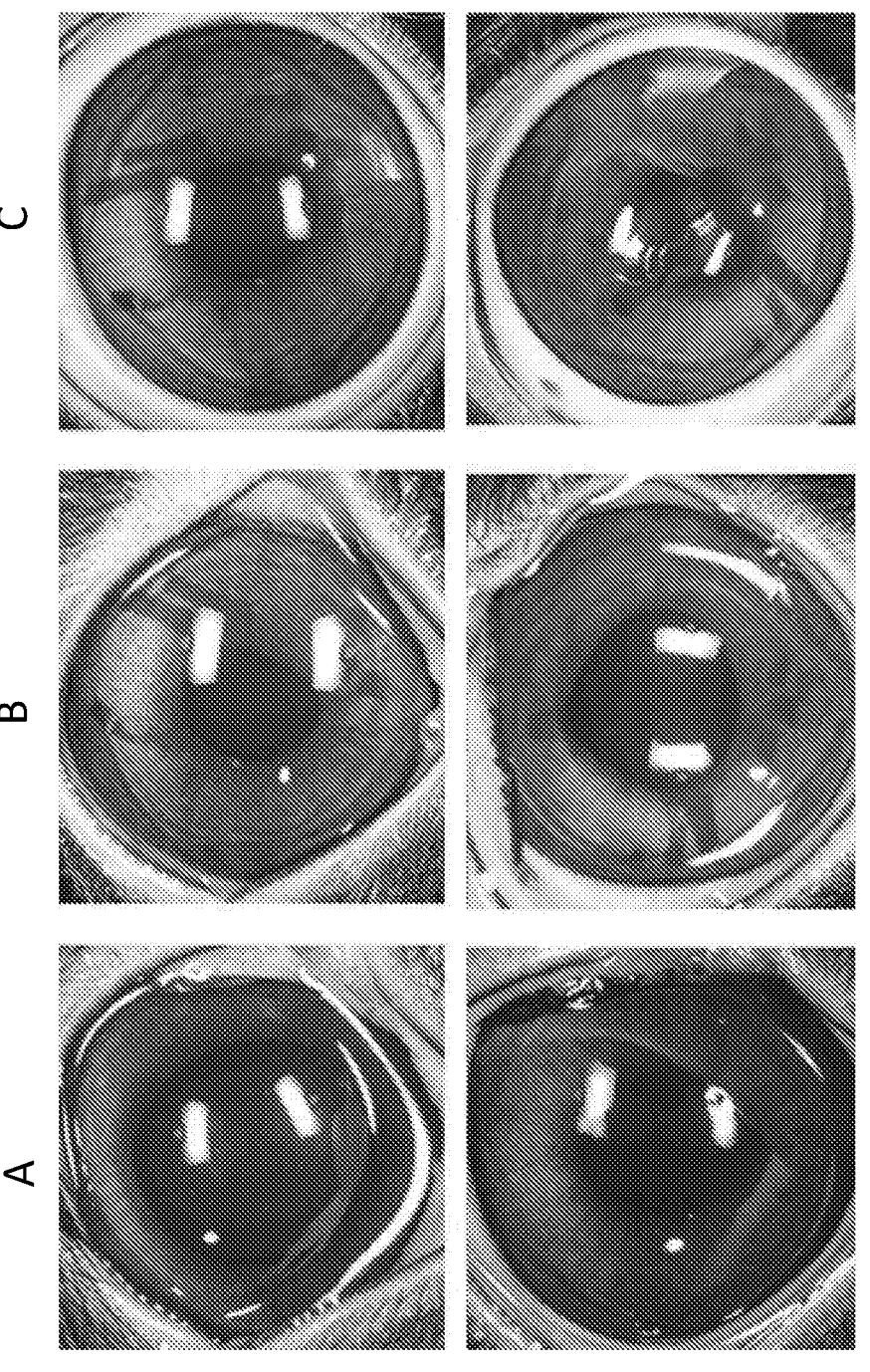
FIG. 19 is an enface image of in vivo exposed rabbit irises, before (A), immediately after (B), and 1 h-post exposure (C).

Ex Vivo. Experimental evaluation of minimal visible lesions (MVL) of the iris was done on fresh (<25 h post mortem) porcine eyes with removed corneas immersed in water. A 355 nm pulsed laser beam (spot size 180 μm) with variable spot spacing, was scanned over the iris surface, creating rectangular lesions of various sizes. Lesions were analyzed under a surgical microscope to determine the MVL threshold (FIG. 18 and Table 1).

In Vivo. Experimental evaluations of iris MVL were conducted using Dutch-belted rabbits under an approved animal IACUC protocol. The laser was applied in a 1 mm scanned pattern. The initial parameter settings were:

| Pattern Width (mm) | Spot Spacing (μm × μm) | Pulse Energy (μJ) |
|---|---|---|
| 1 | 1 × 1 | 0.51 |
| 1 | 2 × 2 | 0.63 |
| 3 | 1 × 1 | 1.31 |

Immediately after initial exposure, parameter settings were adjusted. If no MVL were present energy was increased by 100. If MVL were present energy was decreased to halfway between the current energy and the highest energy where no MVL were present. (See Table 6, below).

TABLE 6

Raw data table from the in vivo exposures for immediate and 1 h MVL
appearance of all parameters tested.

| Parameters | | Rabbit 151 OS | | | OD | | | Rabbit 152 OS | | | OD | | |
|---|---|---|---|---|---|---|---|---|---|---|---|---|---|
| Width (mm) | Spot spacing (μm) | Energy (μJ) | im. MVL | 1 h MVL | Energy (μJ) | im. MVL | 1 h MVL | Energy (μJ) | im. MVL | 1 h MVL | Energy (μJ) | im. MVL | 1 h MVL |
| 3 | 1 | 1.31 | 0 | 0 | 1.31 | 0 | 0 | 1.31 | 0 | 0 | 1.31 | 0 | 0 |
| 3 | 1 | 2.62 | 1 | 1 | 2.62 | 1 | 1 | 2.62 | 1 | 1 | 2.62 | 1 | 1 |
| 3 | 1 | 1.96 | 1 | 1 | 1.96 | 1 | 1 | 1.96 | 1 | 1 | 1.96 | 1 | 1 |
| 3 | 1 | 1.64 | 0 | 0 | 1.64 | 0 | 0 | 1.64 | 0 | 0 | 1.64 | 1 | 1 |
| 3 | 1 | 1.80 | 0 | 0 | 1.80 | 1 | 1 | 1.80 | 1 | 1 | 1.47 | 0 | 0 |
| 1 | 1 | 0.51 | 0 | 0 | 0.51 | 0 | 0 | 0.51 | 0 | 0 | 0.51 | 0 | 0 |
| 1 | 1 | 1.03 | 0 | 0 | 1.03 | 0 | 0 | 1.03 | 0 | 0 | 1.03 | 0 | 0 |
| 1 | 1 | 2.06 | 1 | 1 | 2.06 | 1 | 1 | 2.06 | 1 | 1 | 2.06 | 1 | 1 |
| 1 | 1 | 1.54 | 1 | 1 | 1.54 | 1 | 1 | 1.54 | 1 | 1 | 1.54 | 1 | 1 |
| 1 | 1 | 1.29 | 1 | 1 | 1.29 | 0 | 0 | 1.29 | 1 | 1 | 1.29 | 0 | 0 |
| 1 | 2 | 0.63 | 0 | 0 | 0.63 | 0 | 0 | 0.63 | 0 | 0 | 0.63 | 0 | 0 |
| 1 | 2 | 1.27 | 0 | 0 | 1.27 | 0 | 0 | 1.27 | 0 | 0 | 1.27 | 0 | 0 |
| 1 | 2 | 2.54 | 1 | 1 | 2.54 | 1 | 1 | 2.54 | 1 | 1 | 2.54 | 1 | 1 |
| 1 | 2 | 1.90 | 1 | 1 | 1.90 | 1 | 1 | 1.90 | 1 | 1 | 1.90 | 1 | 1 |
| 1 | 2 | 1.58 | 1 | 1 | 1.58 | 1 | 1 | 1.58 | 0 | 0 | 1.58 | 1 | 1 |

MVL 0 = not visible.
MVL 1 = visible.

Calculated Temperature Profile of Scanning the Iris with Pulsed Laser

Analytical Point Spread Function (PSF) solution and Finite Element Mesh (FEM) methods were used for temperature calculation. Temperature rise was calculated for a 1 μJ, 70 kHz lasers beam using a lawn-mower pattern, variable spot spacing (1-3 μm) and distant boundary conditions at body temperature. The analytical solution was used to verify the FEM method. All results were compared to the experimental MVL threshold data (See Table 7, below).

TABLE 7

Ex viva porcine MVL threshold as function of the
spot spacing and width of the cut. Calculated temperature is 75° C.

| | Spot spacing (pattern size = 1 mm × 1 mm) | | | | | |
|---|---|---|---|---|---|---|
| | 1 × 1 μm | | 1.5 × 1.5 μm | | 2 × 2 μm | |
| Eye # | No Lesion (μJ) | Lesion (μJ) | No Lesion (μJ) | Lesion (μJ) | No Lesion (μJ) | Lesion (μJ) |
| 1 | 1.0 | 1.1 | 1.1 | 1.2 | 1.1 | 1.2 |
| 2 | 0.9 | 1.0 | 1.0 | 1.1 | 1.4 | 1.5 |
| 3 | 1.1 | 1.2 | 1.2 | 1.3 | 1.2 | 1.3 |
| 4 | 0.9 | 1.0 | 1.1 | 1.2 | 1.2 | 1.3 |
| MVL | $ED_{50} = 1.04$ μJ | | $ED_{50} = 1.148$ μJ | | $ED_{50} = 1.27$ μJ | |

| | Spot spacing (pattern size = 1 mm × 1 mm) | | |
|---|---|---|---|
| | 1 × 1 μm | 1.5 × 1.5 μm | 2 × 2 μm |
| MVL | $ED_{50} = 1.04$ μJ | $ED_{50} = 1.84$ μJ | $ED_{50} = 2.6$ μJ |
| FEM Temperature | 72.6° C. | 75.9° C. | 77.4° C. |

| | Pattern width (pattern length = 1 mm, spot spacing = 1 μm × 1 μm) | | | | | |
|---|---|---|---|---|---|---|
| | 1 mm | | 2 mm | | 3 mm | |
| Eye # | No Lesion (μJ) | Lesion (μJ) | No Lesion (μJ) | Lesion (μJ) | No Lesion (μJ) | Lesion (μJ) |
| 1 | 1 | 1.1 | 1.7 | 1.8 | 2.5 | 2.6 |
| 2 | 0.9 | 1.0 | 1.7 | 1.8 | 2.4 | 2.5 |
| 3 | 1.1 | 1.2 | 2.1 | 2.2 | 2.7 | 2.8 |
| 4 | 0.9 | 1.0 | 1.7 | 1.8 | 2.6 | 2.7 |
| MVL | $ED_{50} = 1.04$ μJ | | $ED_{50} = 1.84$ μJ | | $ED_{50} = 2.6$ μJ | |

TABLE 7-continued

Ex viva porcine MVL threshold as function of the
spot spacing and width of the cut. Calculated temperature is 75° C.

| | Pattern width (pattern length = 1 mm, spot spacing = 1 μm × 1 μm) | | |
| --- | --- | --- | --- |
| | 1 mm | 2 mm | 3 mm |
| MVL | $ED_{50}$ = 1.04 μJ | $ED_{50}$ = 1.84 μJ | $ED_{50}$ = 2.6 μJ |
| FEM Temperature | 72.6° C. | 76.7° C. | 75.5° C. |

Figure 15A:
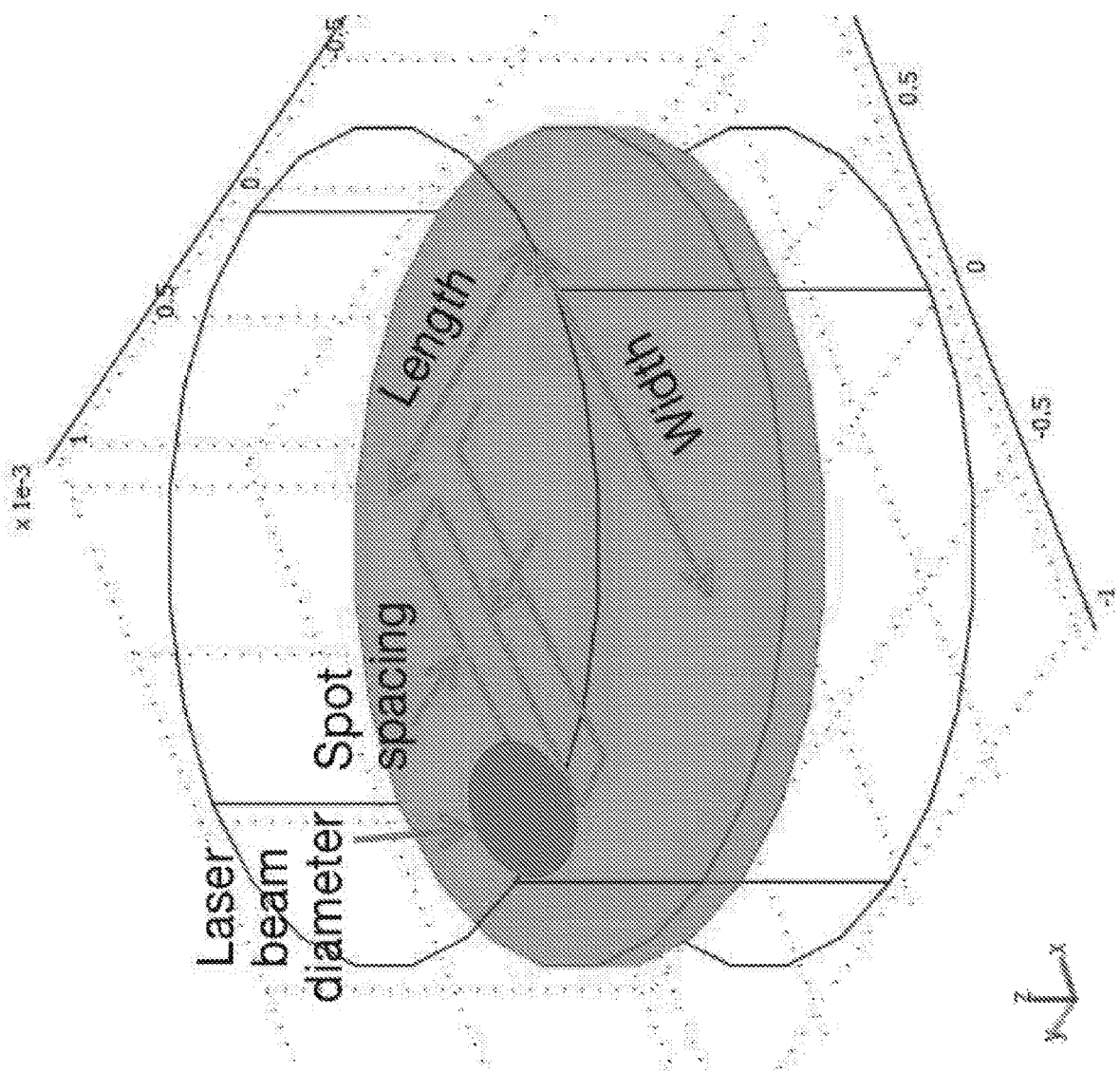
FIG. 15A is a schematic diagram illustrating a Lawn-mower raster pattern on the iris surface.
Figure 15B:
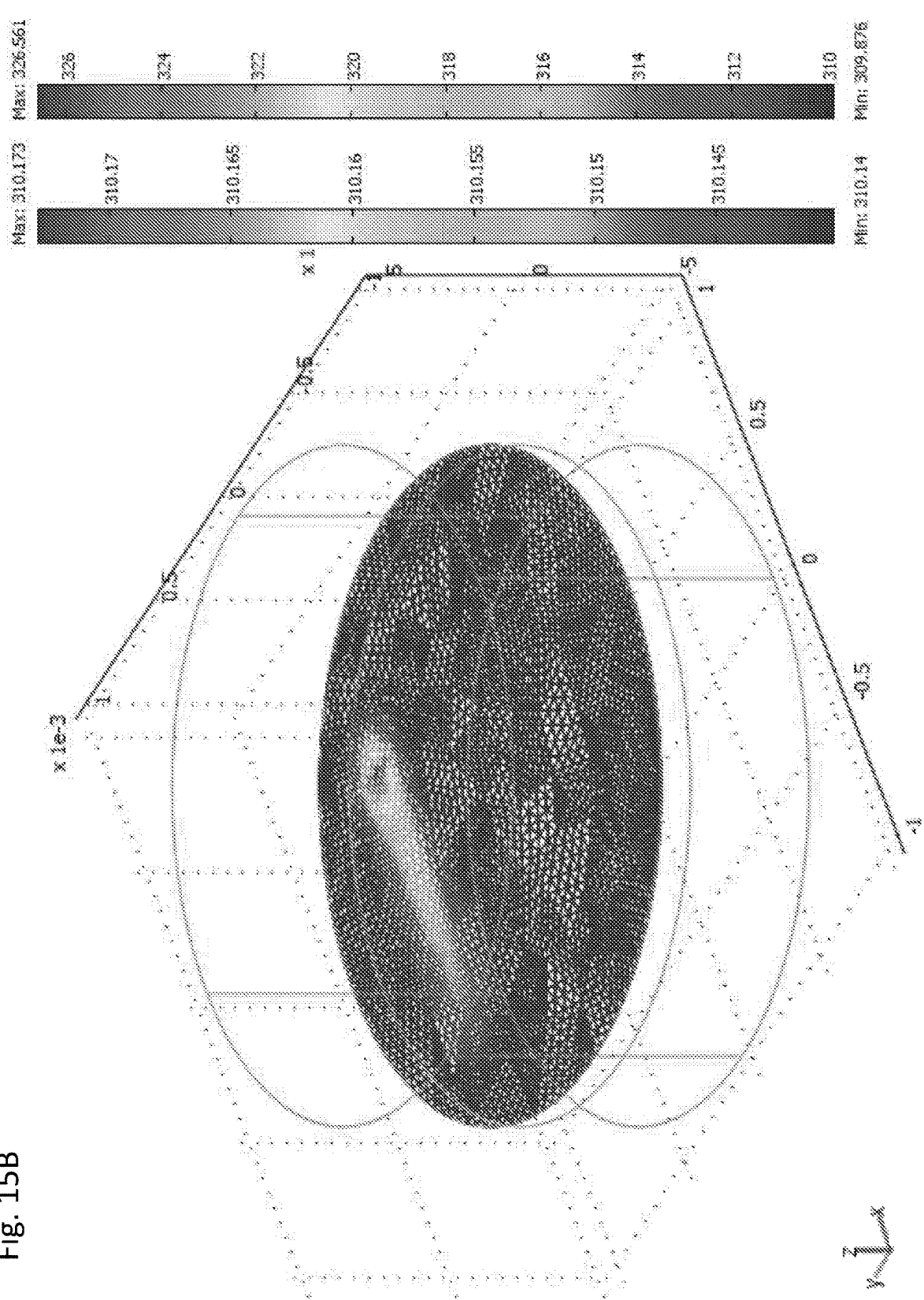
FIG. 15B is a graphical illustration showing the calculated temperature on the iris surface at a single point in time during the scan.

Temperature was calculated based on the thermal diffusion equation with remote fixed-temperature boundary conditions (FIGS. 15A and 15B).

$$\rho C \frac{\partial T}{\partial t} + \nabla(-k\nabla T) = Q_{ext}(x, y, z, t)$$

p=1000 kg/m$^3$ mass density
D=100 μm iris thickness
C=4781 J/(kg·K) specific heat of tissue
k=0, 597 W/(m·K) thermal conductivity of tissue
beam_r=90 μm 1/e beam radius
α=20 mm$^{-1}$ extinction coefficient
$I_0$=2.75 MW/m$^2$ irradiance in the center of the beam (70 mW)

Figure 16:
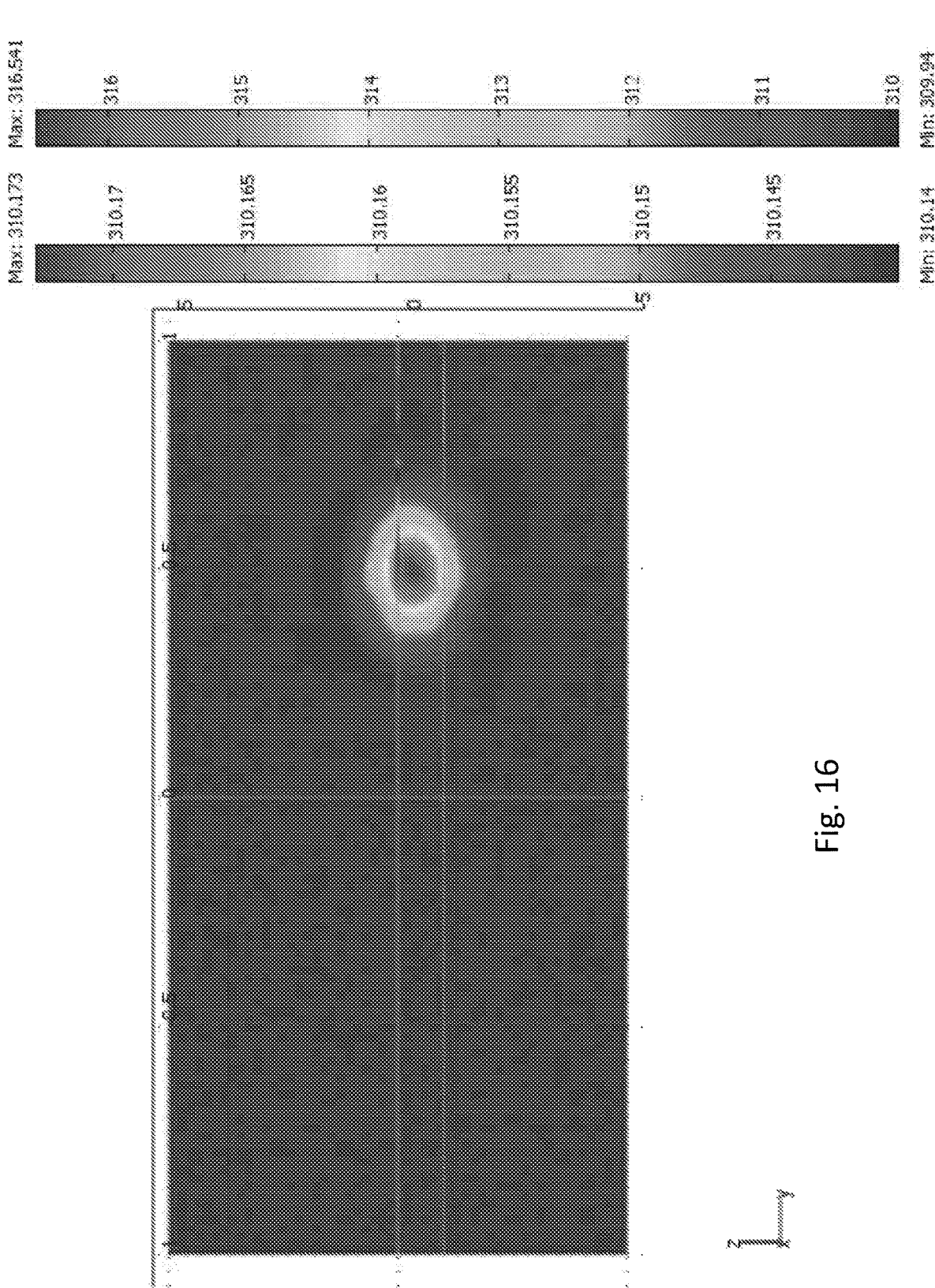
FIG. 16 is a graphical illustration showing a vertical cross-section of the temperature profile of the iris at a single point in time during the scan. The horizontal layer in the center is the iris.
Figure 17:
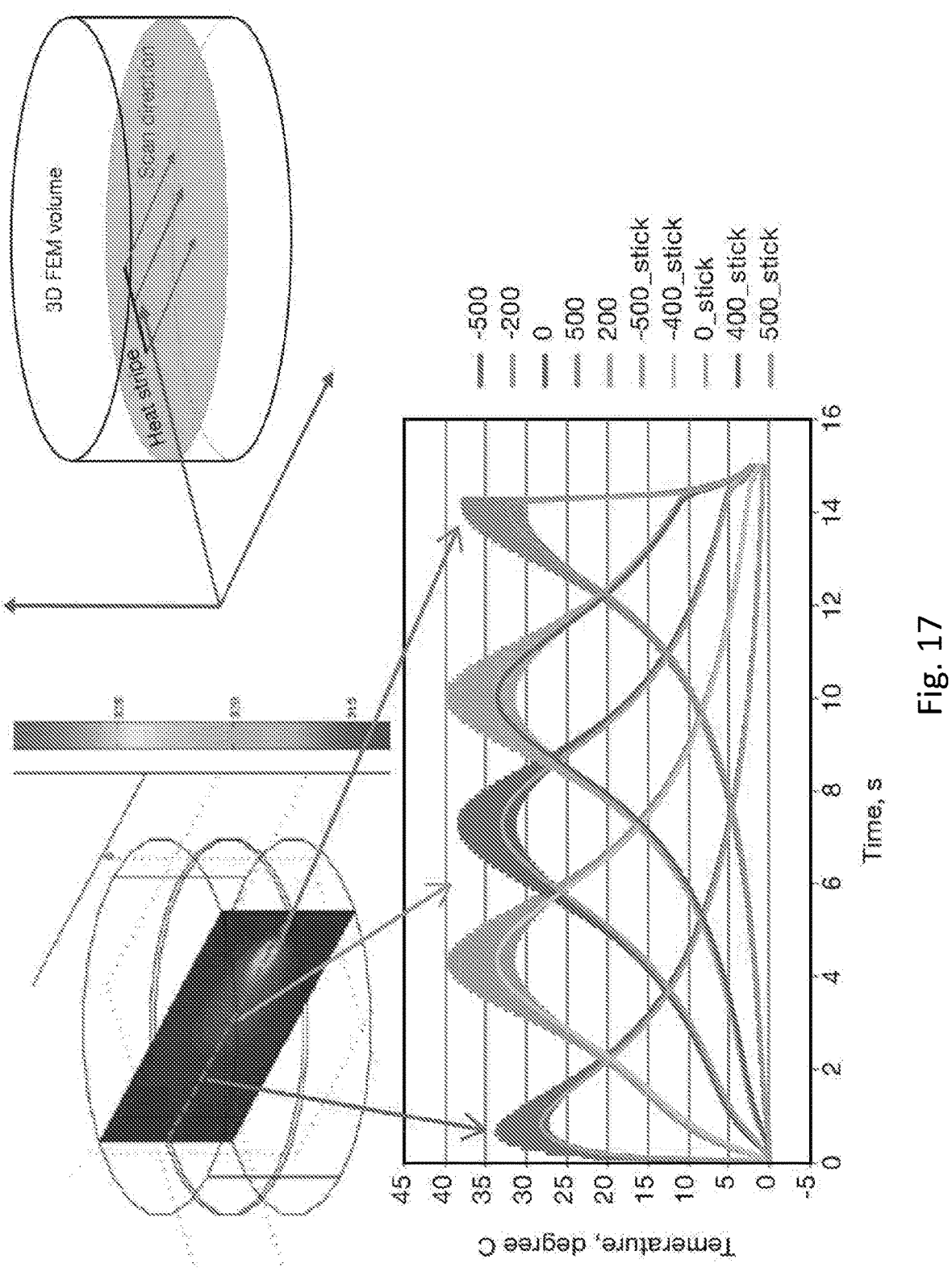
FIG. 17 is a graphical illustration of the temporal profile of the temperature at different points of the iris on the center of the scan.

Based on these foregoing, the following observations can be made regarding the temperature rise in tissue caused by pulsed laser scanning:

1. The temperature of the iris tissue reaches the maximum about 40 μm under the iris surface (FIG. 16);
2. The temperature of the iris tissue reaches a steady state in a fraction of second, and therefore, a maximum temperature of the iris tissue is independent of cut length;
3. The temperature profile consists of relatively slow temperature changes and relatively fast oscillations (FIG. 17);
4. Slow temperature changes correspond to the heat stripe scan in which only the slow-scanned axis of the pattern moves, as shown in FIG. 17, upper right. The heat stripe (black line) is scanned in one axis (red arrows) within the overall 3D FEM volume mesh. Fast oscillations were within 15% of the total maximum temperature.

Using this simplified model, it was found that:

1. A wide cut is cooler than a narrow cut;
2. The temperature of the iris tissue is inversely proportional to the width of the scan;
3. The maximum temperature of the iris tissue is almost independent of the spot spacing; and
4. Overall, the calculated temperatures of 75±2° C. for all cases were consistent with the assumption that the threshold temperature should be the same in all exposure settings.

Maximum temperature of the moving stripe depends on width and velocity of the stripe.

The velocity of the scanned line for a 2 μm-spot spacing, 70 kHz laser is 0.28 mm/s. The solution of the slowly moving line is close to the stationary line solution where movement is slow enough that thermal distribution can follow the movement of the line. As a result, all velocities slower than 1 mm/s have the maximum temperature close to the stationary solution. For instance, the maximum temperature for 1 μm spot spacing is 15% greater than the maximum for 2 μm. Thus, temperature has a weak dependence on spot spacing.

Since the exposure in J/cm$^2$ is dependent on spot density only, and the MVL threshold is a function of time, the threshold must be expressed in terms of the exposure time of a particular size of integrating aperture. The integrating aperture was chosen to match the integrating aperture specified for the Group 2 anterior chamber limit from IS015004, of 0.5 mm diameter as the most appropriate aperture for the iris.

The area of this aperture was then converted to a square aperture of the same area as the 0.5 mm diameter circular aperture, which is a square of 0.44 mm×0.44 mm (FIG. 20) for the minimum visible lesion threshold function. It is therefore necessary to compute the exposure time for an integrating aperture of (0.44 mm)$^2$ to find the threshold exposure from the function. Fitting the data over the time region of interest by least squares fit of the data at the 1.86 s and 19.23 s (rabbit only) time points allows the MVL as a function of time to be conservatively expressed as:

$$MVL(T)=22T^{0.69}J/cm^{2-}$$

where T is the time for the scanned pattern to pass over a (0.44 mm)$^2$ integration aperture. (See Table 8)

Experimental results match the theoretical model for predicting MVL. Based on these results, one can calculate parameters of a laser scanning system for various incision geometries.

TABLE 8

Combined threshold MVL for porcine and rabbit exposure on the iris.
Combined porcine and rabbit threshold data (J/cm$^2$)

| Exposure parameters | 1 mm × 2 μm | 1 mm × 1.5 μm | 1 mm × 1.0 μm | 1 mm × 2 mm × 1.0 μm | 1 mm × 3 mm × 1.0 μm |
| --- | --- | --- | --- | --- | --- |
| 0.44 mm cell pass over time (T) | 1.86 | 2.79 | 6.56 | 12.57 | 19.23 |
| Pig eye 1 | 29 | 51 | 105 | 175 | 255 |
| Pig eye 2 | 36 | 47 | 95 | 175 | 245 |
| Pig eye 3 | 31 | 56 | 115 | 215 | 275 |
| Pig eye 4 | 31 | 51 | 95 | 175 | 265 |
| Rabbit OS 151 | 35 | | 115 | | 190 |
| Rabbit OD 151 | 35 | | 141 | | 174 |
| Rabbit OS 152 | 42 | | 115 | | 174 |
| Rabbit OD 152 | 35 | | 141 | | 157 |
| Average | 34 | 51 | 115 | 185 | 217 |
| Fit (22*T$^{0.69}$) | 34 | 45 | 82 | 129 | 174 |

CONCLUSIONS

The foregoing experiments support at least the following conclusions:

1. Steady state is achieved in fractions of seconds;
2. Maximum temperature profile is in the center of the cut;
3. Temperature profile consists of slow temperature change and fast oscillations; and
4. The threshold MVL can be modeled by the function $22T^{0.69}$ (J/cm$^2$) where T is the time for the scanned pattern to pass over a (0.44 mm)$^2$ integration aperture While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A system for cataract surgery on an eye of a patient, comprising:
   a laser assembly for generating a pulsed laser treatment beam;
   an imaging system configured for imaging an ocular tissue of the patient, the ocular tissue comprising corneal tissue;
   an optical scanning system configured for positioning a focal zone of the treatment beam to targeted locations of the ocular tissue, the targeted locations including a location in the corneal tissue; and
   a computer control system operatively coupled to the laser assembly, the imaging system, and the optical scanning system, and programmed to:
   generate a simulated initial treatment scan pattern of the pulsed laser treatment beam corresponding to a predetermined corneal incision in the eye;
   calculate a first time period over which the initial treatment scan pattern is carried out to deliver a first amount of laser energy on an iris tissue of the eye;
   determine whether the first time period is greater than a predetermined minimum time period to deliver the first amount of laser energy on the iris tissue;
   generate a simulated revised treatment scan pattern of the pulsed laser treatment beam for incising the corneal tissue which is different from the initial treatment scan pattern and which comprises one or more treatment scan modifying elements when the first time period is not greater than the predetermined minimum time period, wherein the one or more treatment scan modifying elements cause a calculated second time period over which the revised treatment scan pattern is carried out to be greater than the predetermined minimum time period; and
   operate the optical scanning system and laser assembly to direct the laser treatment beam according to the revised treatment scan pattern, thereby performing the corneal incision.

2. The system of claim 1, wherein the one or more treatment scan modifying elements comprises an extension of scan paths so that at least a portion of turnarounds occur beyond an incision boundary, the extension of the scan paths being greater than 50% of a turnaround distance, and wherein a region corresponding to the portion of the scan paths extending beyond the respective incision boundary is not incisionable by the pulsed laser treatment beam.

3. The system of claim 1, wherein the one or more treatment scan modifying elements comprises an extension of the scan paths so that at least a portion of turnarounds are gated and extend beyond the incision boundary, the extension of the scan paths being greater than 50% of a turnaround distance.

4. The system of claim 1, wherein the one or more treatment scan modifying elements comprises a reoriented scan axis, and wherein the reoriented axis is reoriented along an axis corresponding to a largest distance between opposing incision boundaries.

5. The system of claim 1, wherein the one or more treatment scan modifying elements comprises a plurality of gated rows of a scan path inserted among active rows of the scan path in a fixed proportion, the fixed proportion being greater than or equal to one and less than or equal to 10.

6. The system of claim 1, wherein the computer control system is further programmed to perform a capsulotomy on the eye with the laser treatment beam.

7. The system of claim 1, wherein the corneal incision is an arcuate corneal incision, a sideport cataract incision, or a primary cataract incision.

8. The system of claim 1, wherein the initial scan pattern includes a set of parameters defining an arcuate corneal incision, a sideport cataract incision, or a primary cataract incision.

9. The system of claim 8, wherein the revised treatment scan pattern further includes a revised value for at least one of the set of parameters.

10. A system for cataract surgery on an eye of a patient, comprising:
   a laser assembly for generating a pulsed laser treatment beam;
   an imaging system configured for imaging an ocular tissue of the patient, the ocular tissue comprising corneal tissue;
   an optical scanning system configured for positioning a focal zone of the treatment beam to targeted locations of the ocular tissue, the targeted locations including a location in the corneal tissue;
   a user interface for receiving input from a user;
   a graphical user interface for providing information to the user; and
   a computer control system operatively coupled to the laser assembly, the imaging system, the optical scanning system, the user interface and the graphical user interface, and programmed to:
   receive a parameter set from a user via a user interface device;
   generate a simulated initial treatment scan pattern of the laser treatment beam for incising the corneal tissue based on the parameter set received via the user interface device;
   calculate an initial exposure level, which is an amount of laser energy per unit area of the laser treatment beam on an iris tissue of the eye caused by the initial treatment scan pattern;
   determine whether the initial exposure level satisfies a predetermined safe exposure condition which is below an exposure that causes a minimal visible lesion in the iris tissue;

receive a revised parameter set from the user via the user interface device, the revised parameter set having at least one different parameter value than the initial parameter set, wherein: (1) the parameter set defines an arcuate corneal incision, and the at least one different parameter value is selected from a group of values consisting of incision type, axis, optical zone, arc length, centering method, penetration type, depth units, uncut anterior, uncut posterior, and side cut angle, or (2) the parameter set defines a primary cataract incision, and the at least one different parameter value is selected from a group of values consisting of axis, limbus offset, width, length, uncut region, depth units, uncut anterior, uncut posterior, uncut central length, plane depth, and side cut angle, or (3) the parameter set defines a sideport cataract incision, and the at least one different parameter value is selected from a group of values consisting of number of incisions, axis, limbus offset, width, uncut type, uncut unit, anterior uncut length, posterior uncut length, and side cut angle;

generate a simulated revised treatment scan pattern of the laser treatment beam for incising the corneal tissue which is different from the initial treatment scan pattern and which is based on the revised parameter set received via the user interface;

calculate a revised exposure level, which is an amount of laser energy per unit area of the laser treatment beam on the iris tissue caused by the revised treatment scan pattern;

determine whether the revised exposure level satisfies the predetermined safe exposure condition; and operate the optical scanning system and laser assembly to direct the laser treatment beam according to the revised treatment scan pattern if the revised exposure level satisfies the predetermined safe exposure condition, thereby performing the corneal incision.

\* \* \* \* \*